United States Patent
Mohamed et al.

(10) Patent No.: US 10,016,194 B2
(45) Date of Patent: *Jul. 10, 2018

(54) DEVICES AND METHODS FOR CONTINUOUS SURGICAL SUTURING

(71) Applicant: iSuturing, LLC, Raleigh, NC (US)

(72) Inventors: Adel W. Mohamed, Raleigh, NC (US); Mansour H. Mohamed, Raleigh, NC (US); Dmitri D. Mungalov, Cary, NC (US)

(73) Assignee: ISUTURING, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,863

(22) Filed: Sep. 15, 2017

(65) Prior Publication Data

US 2018/0000478 A1   Jan. 4, 2018

Related U.S. Application Data

(60) Continuation of application No. 14/605,402, filed on Jan. 26, 2015, now Pat. No. 9,775,602, which is a continuation-in-part of application No. 13/898,103, filed on May 20, 2013, now Pat. No. 9,220,498, which is a division of application No. 13/012,965, filed on Jan. 25, 2011, now Pat. No. 8,465,504.

(51) Int. Cl.
| | |
|---|---|
| *A61B 17/04* | (2006.01) |
| *A61B 17/12* | (2006.01) |
| *A61B 17/06* | (2006.01) |
| A61B 17/00 | (2006.01) |

(52) U.S. Cl.
CPC ...... *A61B 17/0469* (2013.01); *A61B 17/0491* (2013.01); *A61B 17/06* (2013.01); *A61B 2017/0046* (2013.01); *A61B 2017/0498* (2013.01); *A61B 2017/061* (2013.01); *A61B 2017/06076* (2013.01)

(58) Field of Classification Search
CPC ............ A61B 17/0469; A61B 17/0491; A61B 2017/0498; A61B 2017/06076
USPC ........................................................ 606/144
See application file for complete search history.

(56) References Cited

U.S. PATENT DOCUMENTS

| | | |
|---|---|---|
| 67,545 A | 8/1867 | Hodgins |
| 196,226 A | 10/1877 | Havell |
| 242,602 A | 6/1881 | Clough |

(Continued)

*Primary Examiner* — Melanie Tyson
(74) *Attorney, Agent, or Firm* — Neo IP

(57) ABSTRACT

A surgical suture module for a machine constructed and configured for automatic, continuous suturing for reduced or minimized scarring and reduced suturing time. A surgical suture module for continuous, subcuticular suturing. The module includes a generally circular needle with a needle shaft; a supply of thread; a thread guide; a hook with a hook shank, a holding arm mechanism; and a housing. The needle, rotationally movable between a first position and a second position, is configured to introduce the thread into a tissue. The hook is operable for hooking and lifting the thread in coordination with the needle and the holding arm mechanism is operable for pushing and catching the thread in automatic coordination with the hook. The needle, the hook, and the holding arm mechanism are held in position by the housing and the housing operable to attach to a power supply that provides power to the module.

20 Claims, 87 Drawing Sheets

(56) References Cited

U.S. PATENT DOCUMENTS

| | | |
|---|---|---|
| 349,791 A | 9/1886 | Gibbonsy |
| 919,138 A | 4/1909 | Drake et al. |
| 1,583,271 A | 5/1926 | Biro |
| 2,327,353 A | 8/1943 | Karle |
| 2,959,172 A | 11/1960 | Held |
| 3,037,619 A | 6/1962 | Ernest |
| 4,204,541 A | 5/1980 | Kapitanov |
| 4,440,171 A | 4/1984 | Nomoto et al. |
| 4,465,070 A | 8/1984 | Eguchi |
| 4,524,771 A | 6/1985 | McGregor et al. |
| 4,641,652 A | 2/1987 | Hutterer et al. |
| 4,969,892 A | 11/1990 | Burton et al. |
| 5,152,769 A | 10/1992 | Baber |
| 5,356,424 A | 10/1994 | Buzerak et al. |
| 5,499,991 A | 3/1996 | Garman et al. |
| 5,507,743 A | 4/1996 | Edwards et al. |
| 5,520,703 A | 5/1996 | Essig et al. |
| 5,562,685 A | 10/1996 | Mollenauer et al. |
| 5,709,692 A | 1/1998 | Mollenauer et al. |
| 5,810,851 A | 9/1998 | Yoon |
| 5,911,689 A | 6/1999 | Smith et al. |
| 5,935,138 A | 8/1999 | William et al. |
| 5,947,983 A | 9/1999 | Solar et al. |
| 6,113,610 A | 9/2000 | Poncet |
| 6,520,973 B1 | 2/2003 | McGarry |
| 6,537,248 B2 | 3/2003 | Mulier et al. |
| 6,562,052 B2 | 5/2003 | Nobles et al. |
| 6,613,058 B1 | 9/2003 | Goldin |
| 6,626,917 B1 | 9/2003 | Craig |
| 6,663,633 B1 | 12/2003 | Pierson |
| 6,723,107 B1 | 4/2004 | Skiba et al. |
| 6,911,003 B2 | 6/2005 | Anderson et al. |
| 6,911,019 B2 | 6/2005 | Mulier et al. |
| 6,911,037 B2 | 6/2005 | Gainor et al. |
| 6,923,807 B2 | 8/2005 | Ryan et al. |
| 6,986,776 B2 | 1/2006 | Craig |
| 7,070,556 B2 | 7/2006 | Anderson et al. |
| 7,144,401 B2 | 12/2006 | Yamamoto et al. |
| D543,626 S | 5/2007 | Watschke et al. |
| 7,235,087 B2 | 6/2007 | Modesitt et al. |
| 7,269,324 B2 | 9/2007 | Crownover |
| 7,288,105 B2 | 10/2007 | Oman et al. |
| 7,290,494 B2 | 11/2007 | Phillips et al. |
| 7,309,325 B2 | 12/2007 | Mulier et al. |
| 7,323,004 B2 | 1/2008 | Parihar |
| 7,335,221 B2 | 2/2008 | Collier et al. |
| 7,347,812 B2 | 3/2008 | Mellier |
| 7,351,197 B2 | 4/2008 | Montpetit et al. |
| 7,357,773 B2 | 4/2008 | Watschke |
| 7,371,224 B2 | 5/2008 | Haischmann et al. |
| 7,377,936 B2 | 5/2008 | Gainor et al. |
| 7,479,115 B2 | 1/2009 | Savic |
| 7,500,945 B2 | 3/2009 | Cox et al. |
| 7,582,103 B2 | 9/2009 | Young et al. |
| 7,588,583 B2 | 9/2009 | Hamilton et al. |
| 7,637,918 B2 | 12/2009 | Dant |
| 7,686,821 B2 | 3/2010 | Hathaway et al. |
| 7,699,805 B2 | 4/2010 | Mulier et al. |
| 7,699,857 B2 | 4/2010 | Kim |
| 7,699,892 B2 | 4/2010 | Rafiee et al. |
| 7,776,059 B2 | 8/2010 | Craig |
| 7,780,700 B2 | 8/2010 | Frazier et al. |
| 7,794,471 B1 | 9/2010 | Bender et al. |
| 9,775,602 B2 * | 10/2017 | Mohamed ......... A61B 17/0469 |
| 2003/0074023 A1 | 4/2003 | Kaplan et al. |
| 2003/0225420 A1 | 12/2003 | Wardle |
| 2006/0036265 A1 | 2/2006 | Dant |
| 2009/0142275 A1 | 6/2009 | Phillips et al. |
| 2011/0029000 A1 | 2/2011 | Lavi et al. |

* cited by examiner

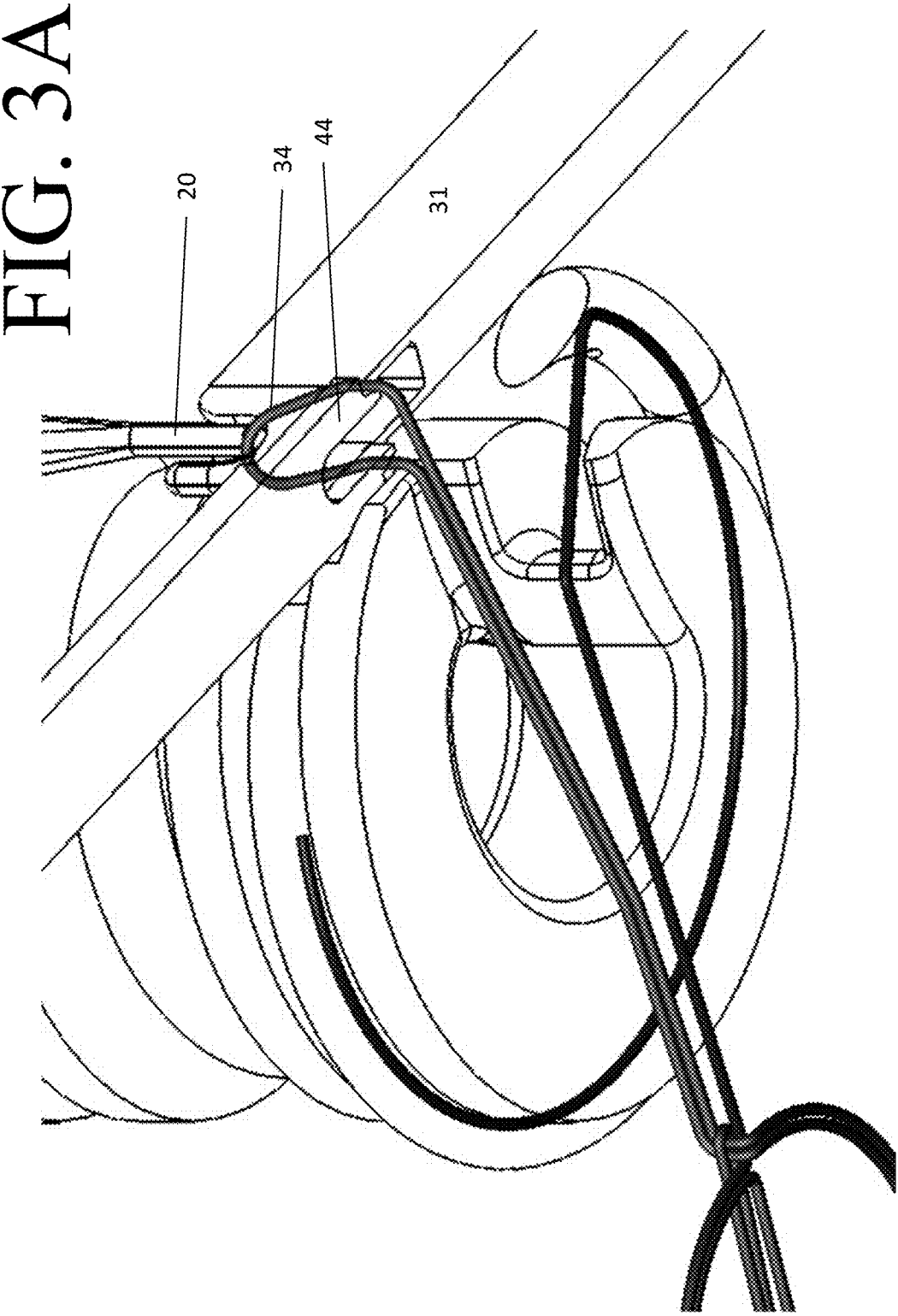

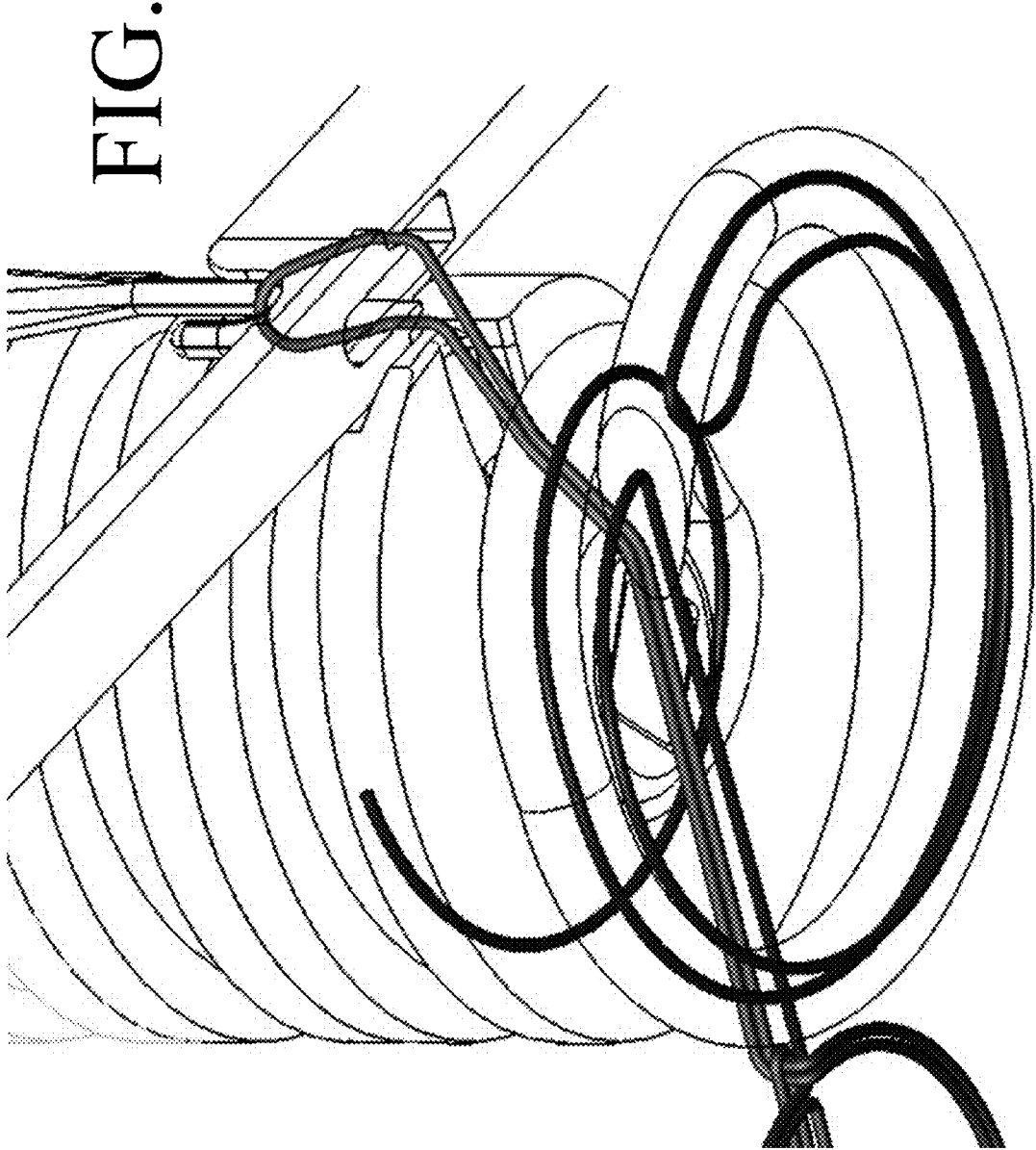

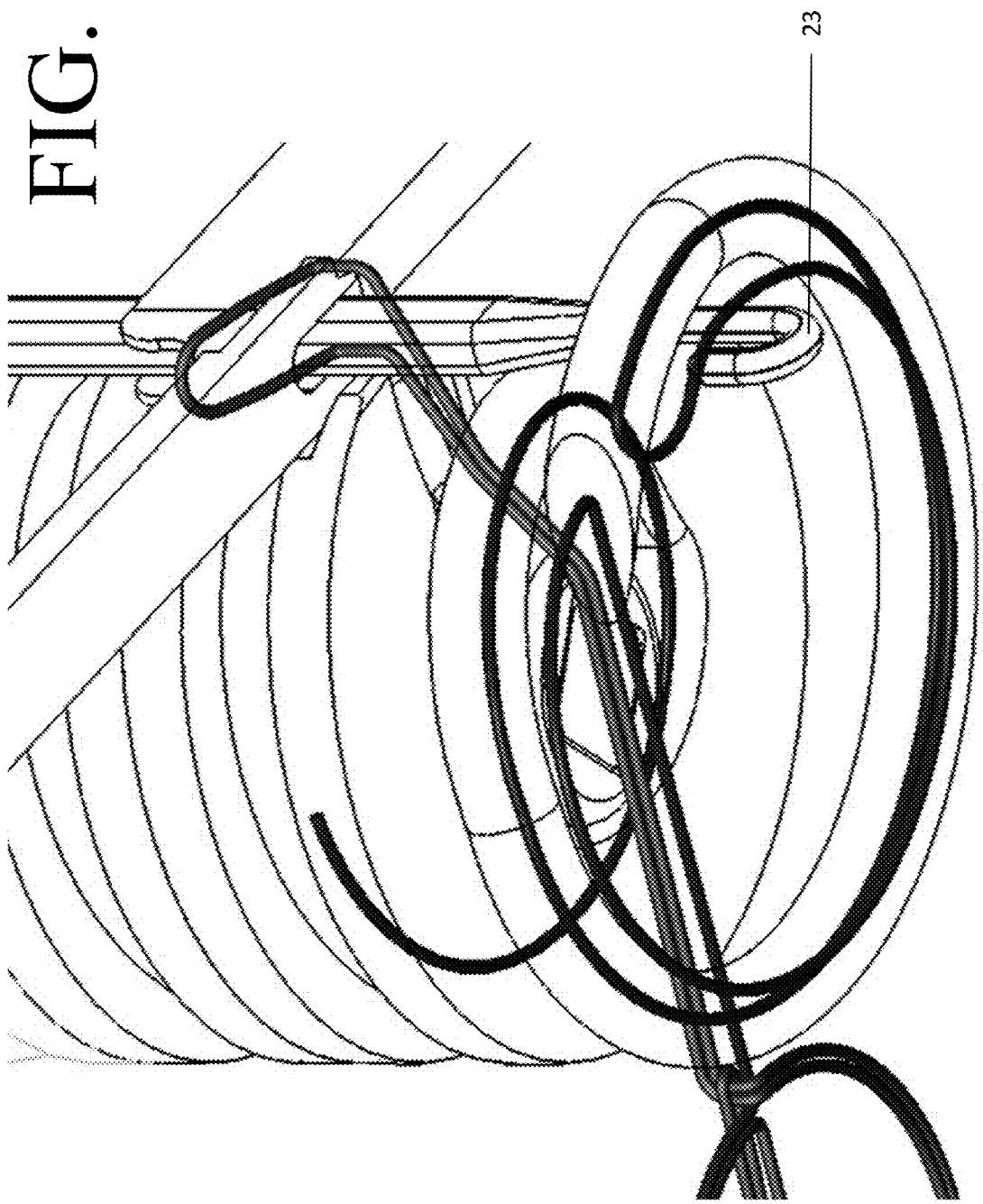

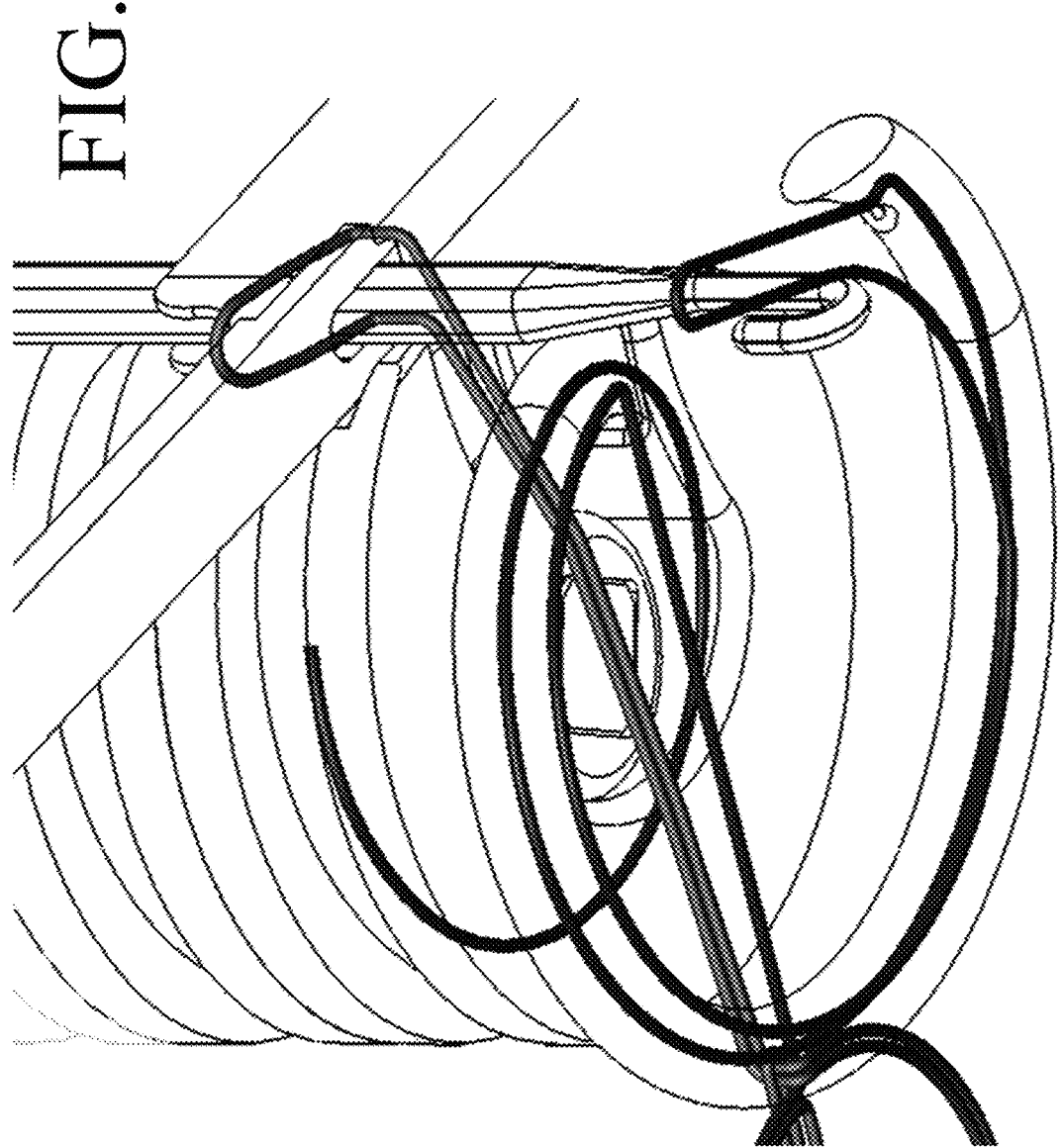

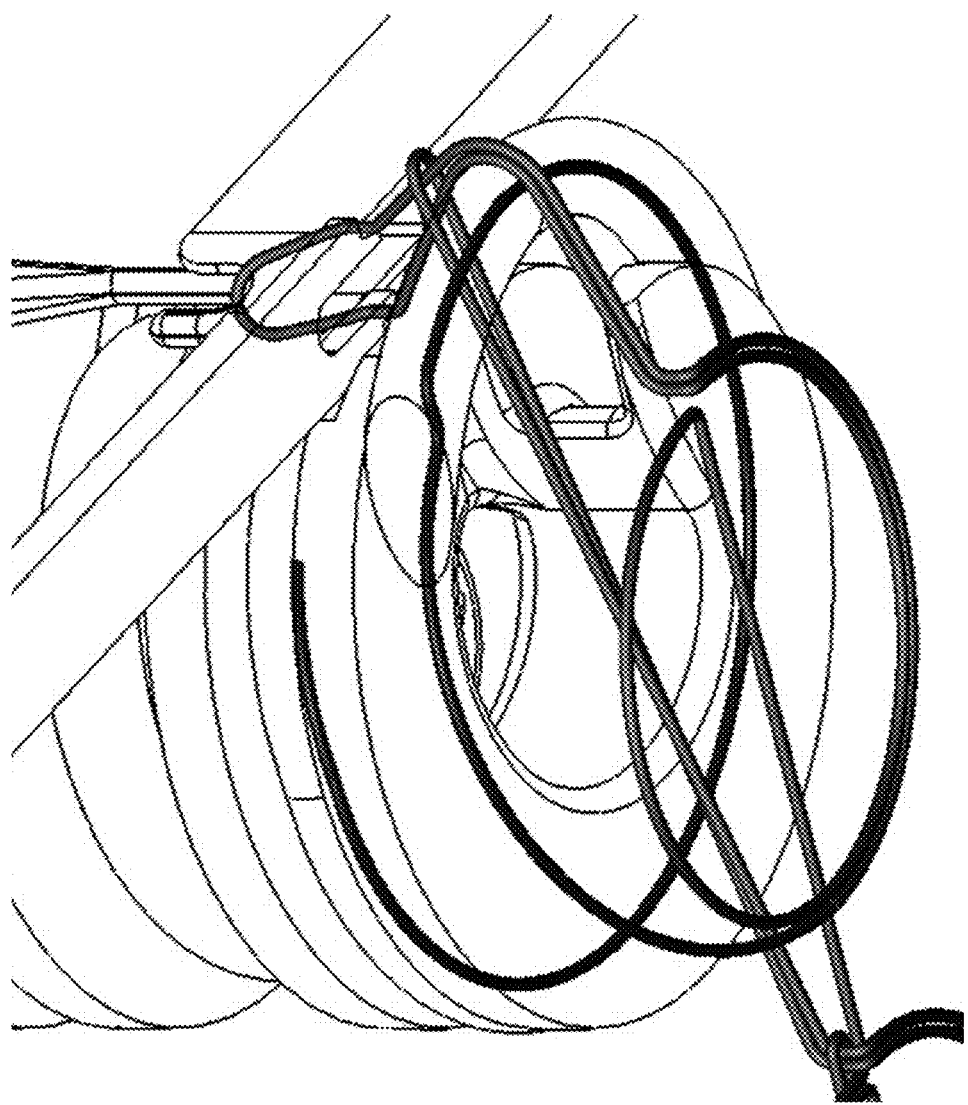

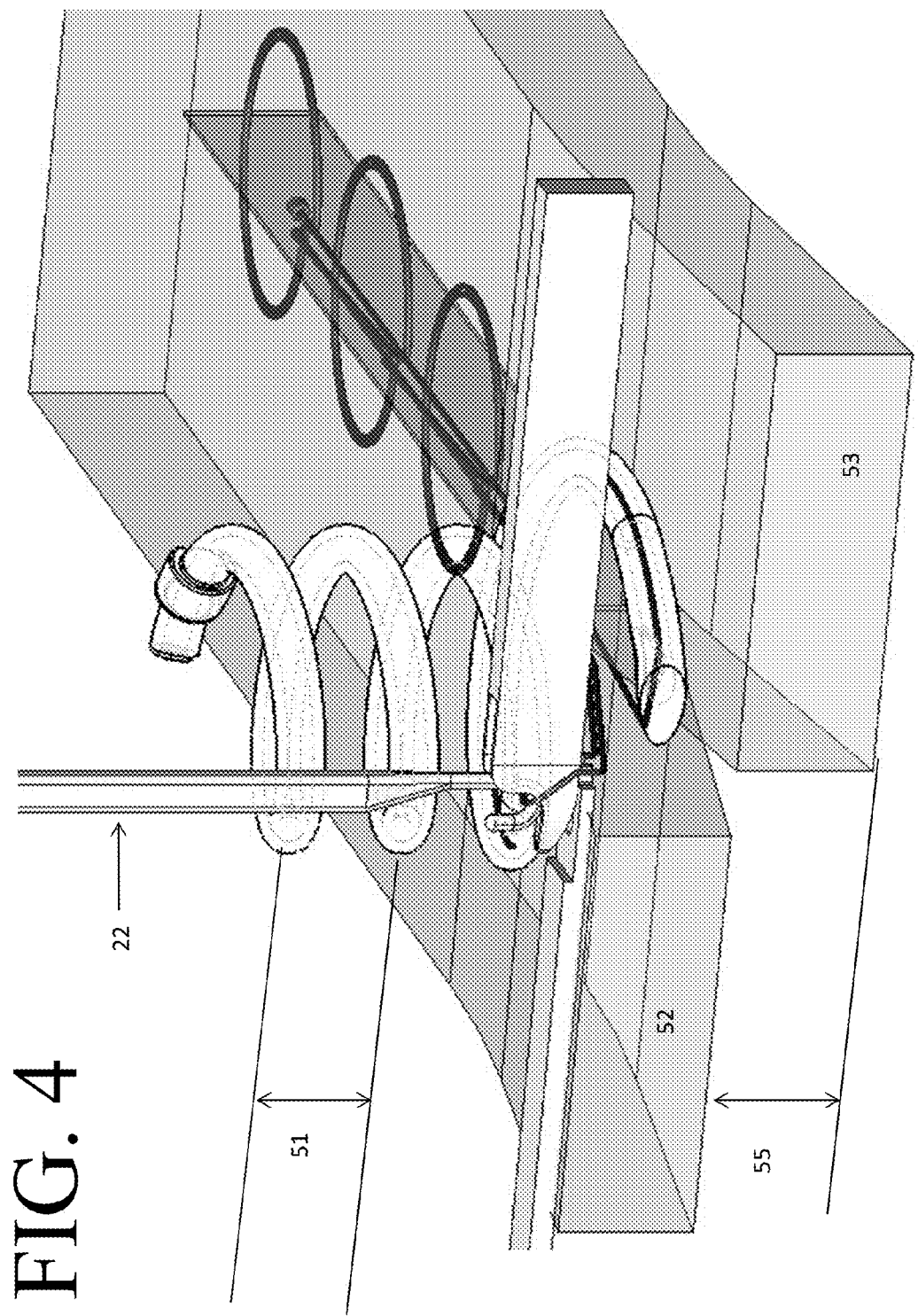

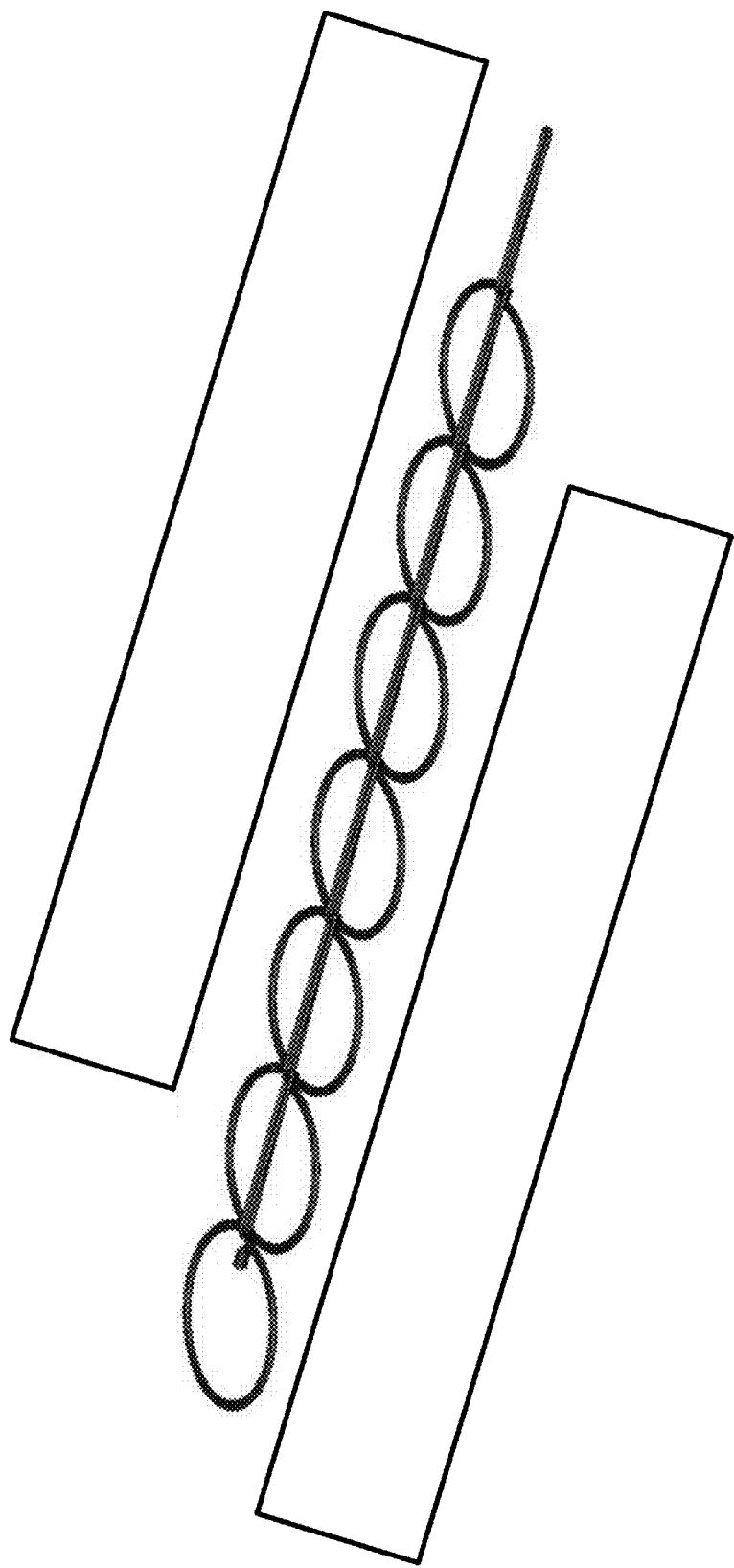

FIG. 11

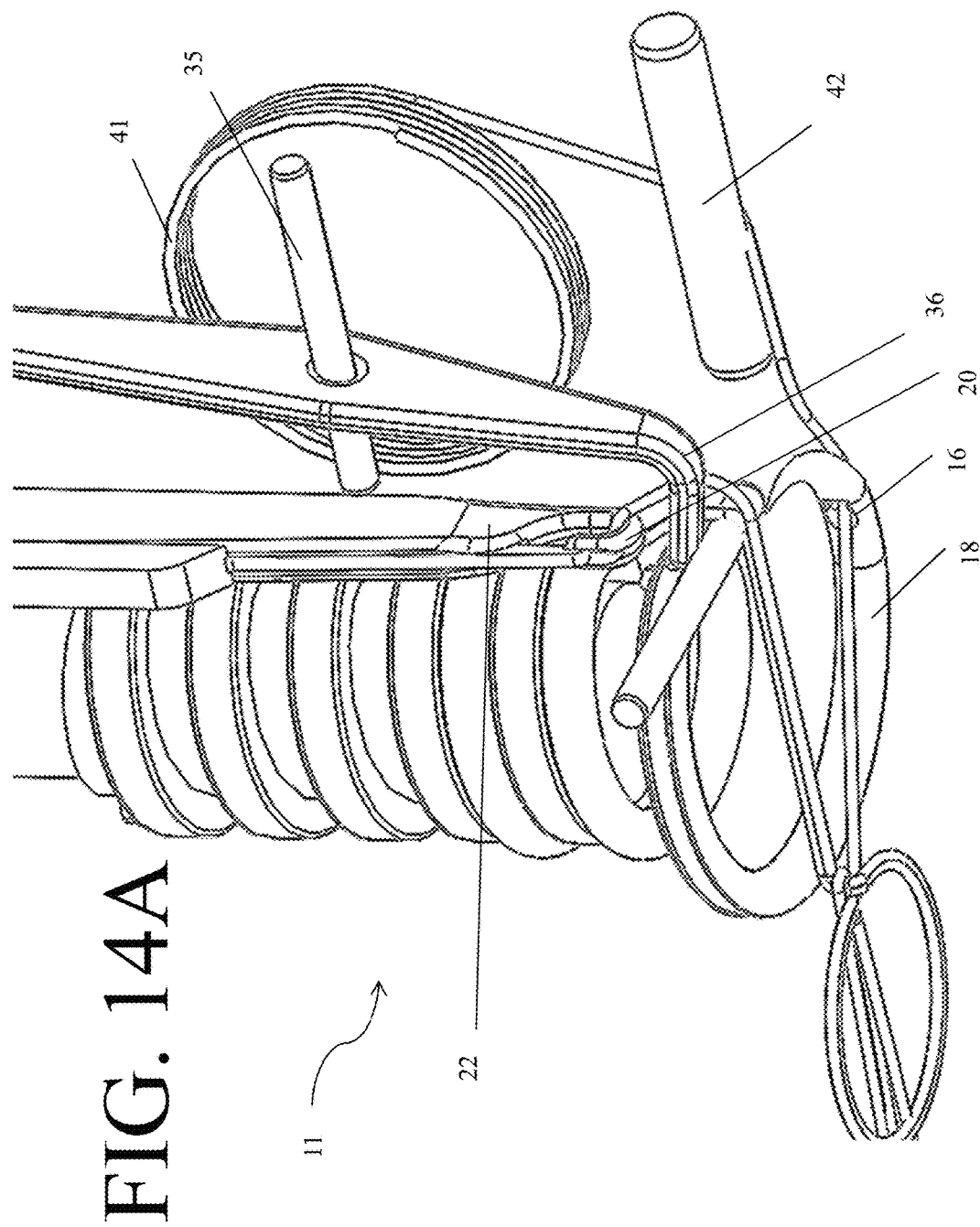

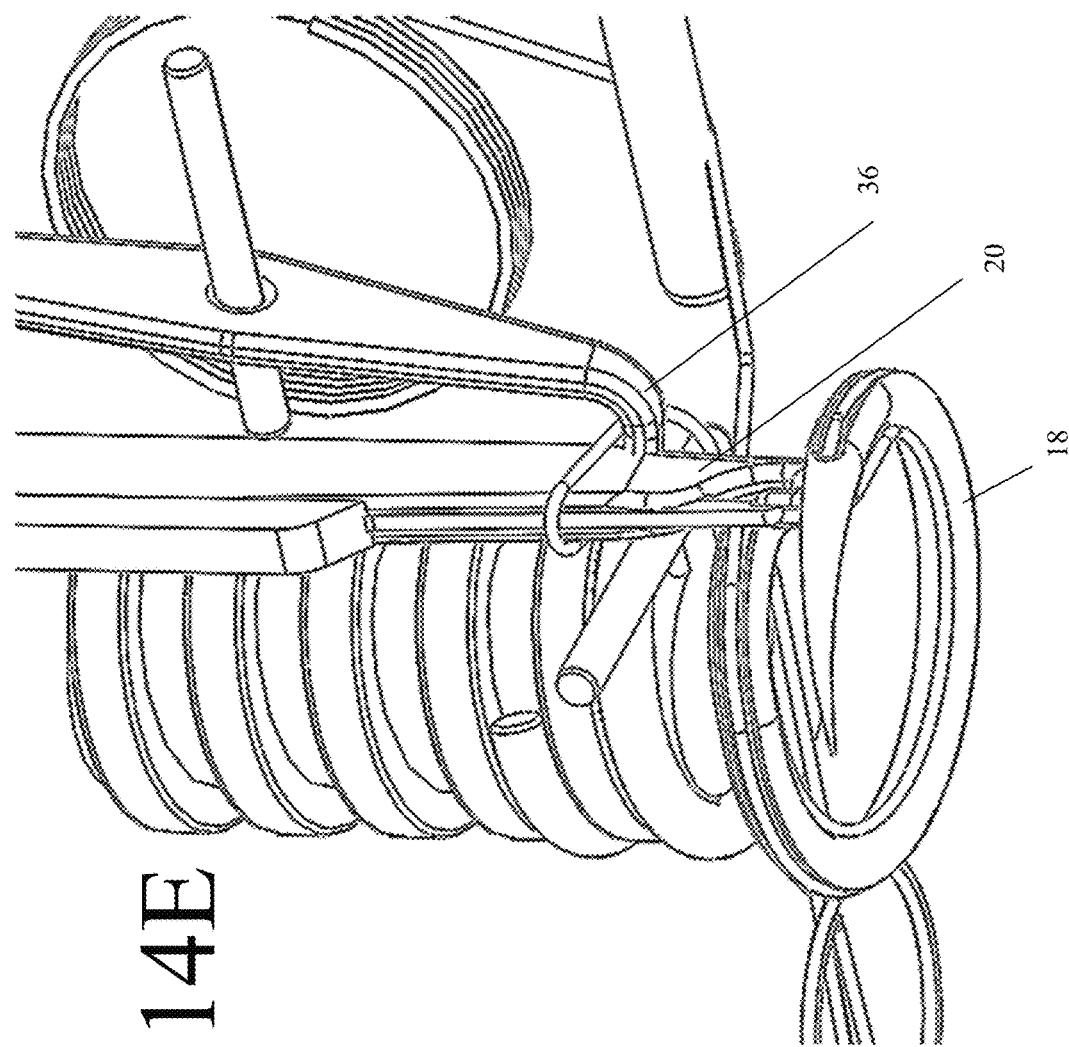

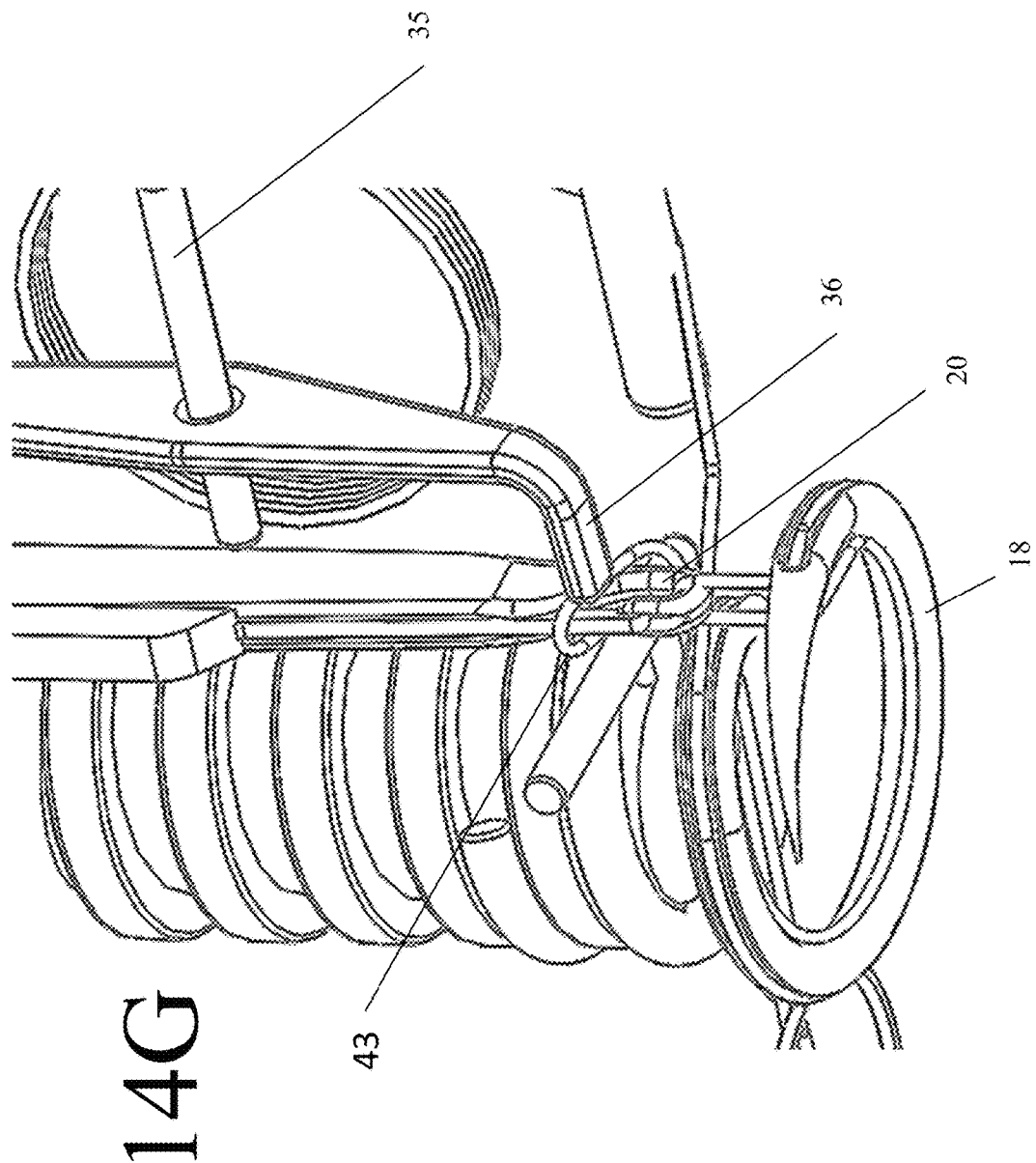

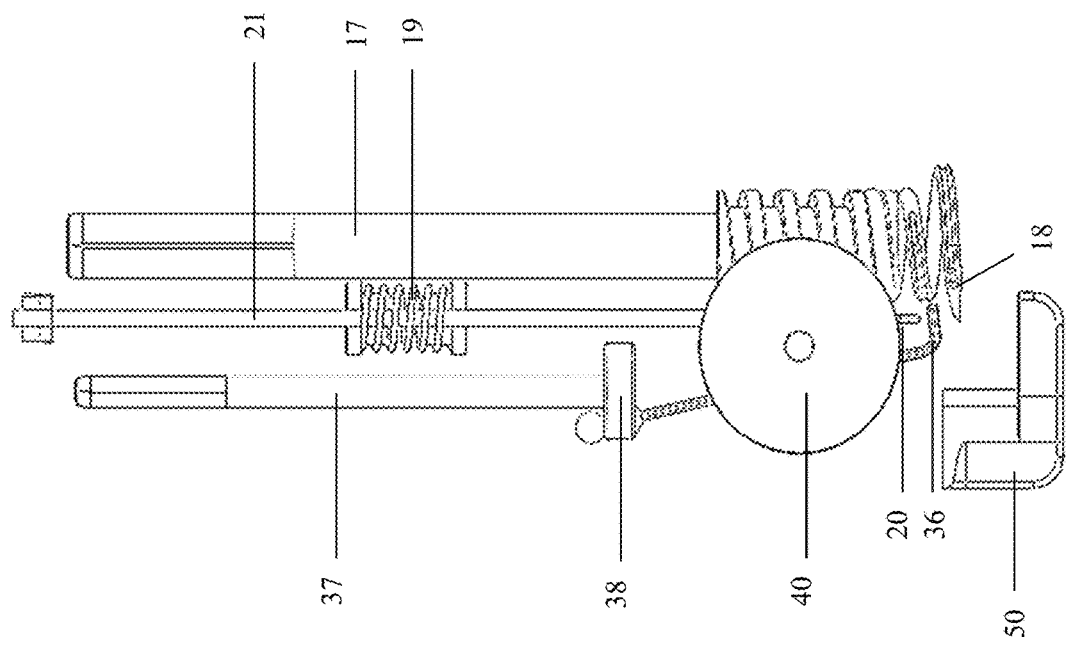

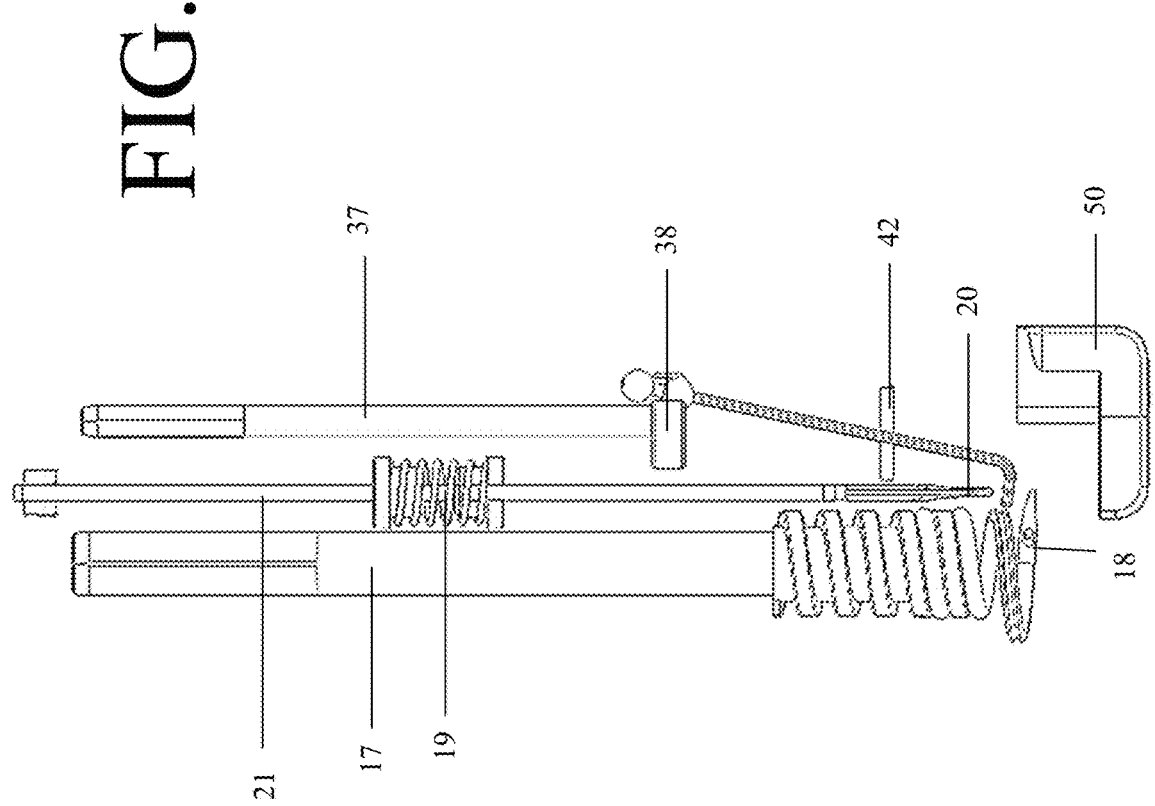

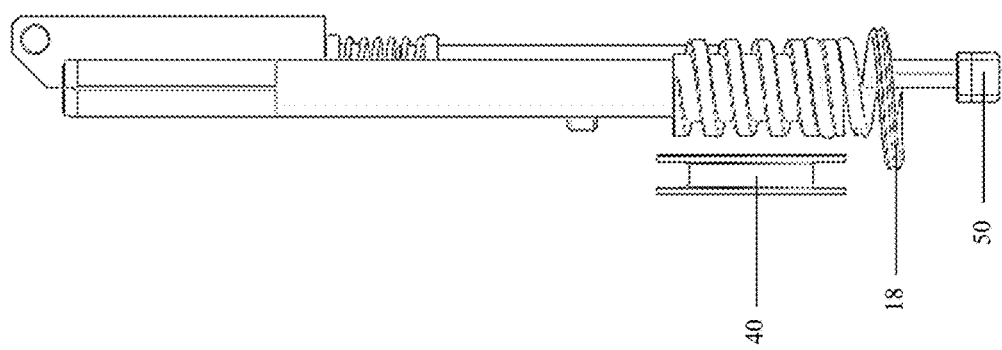

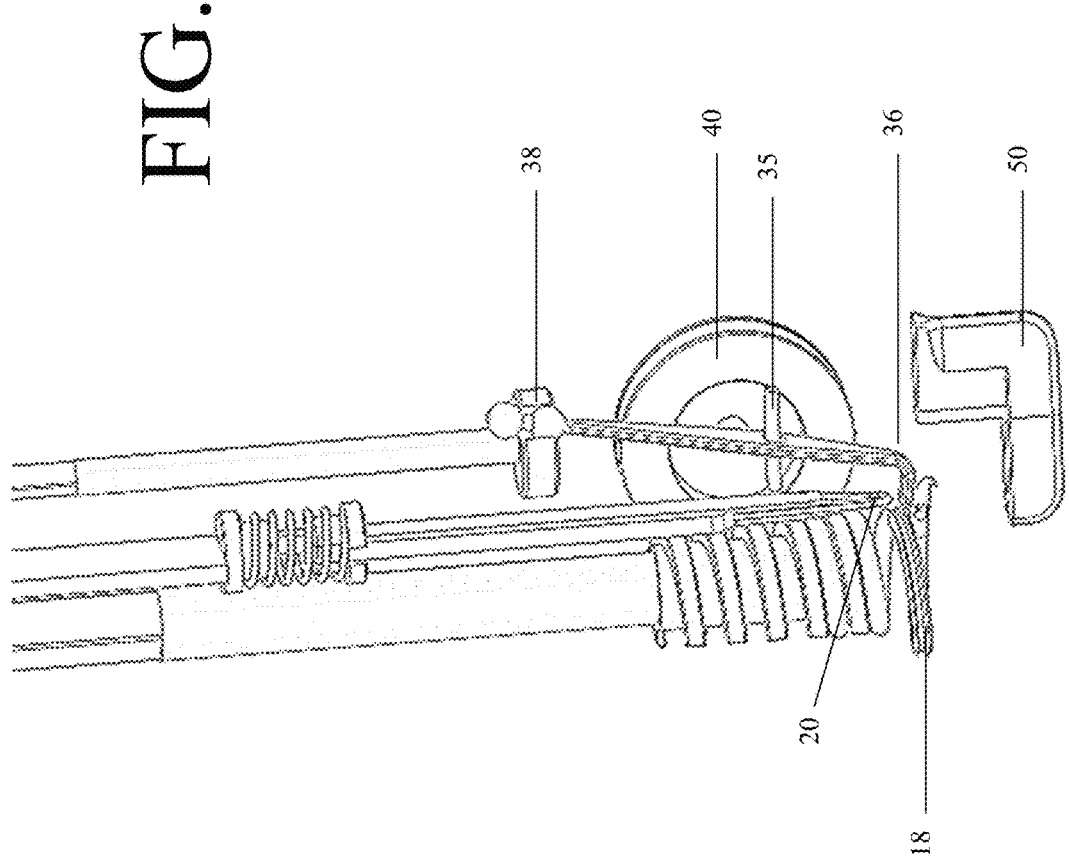

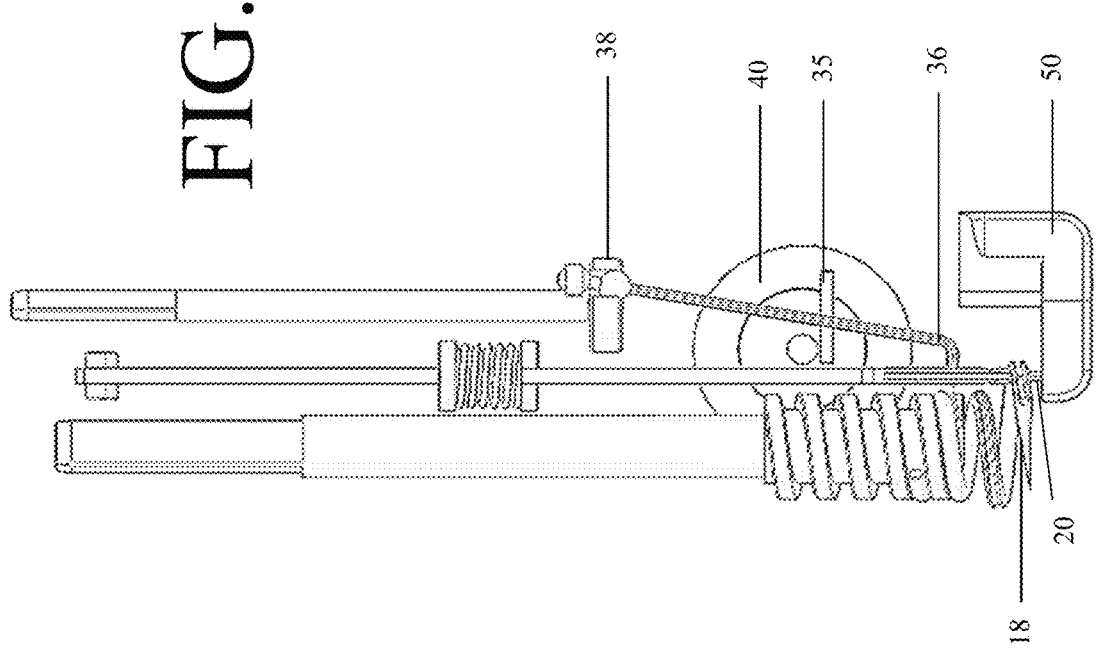

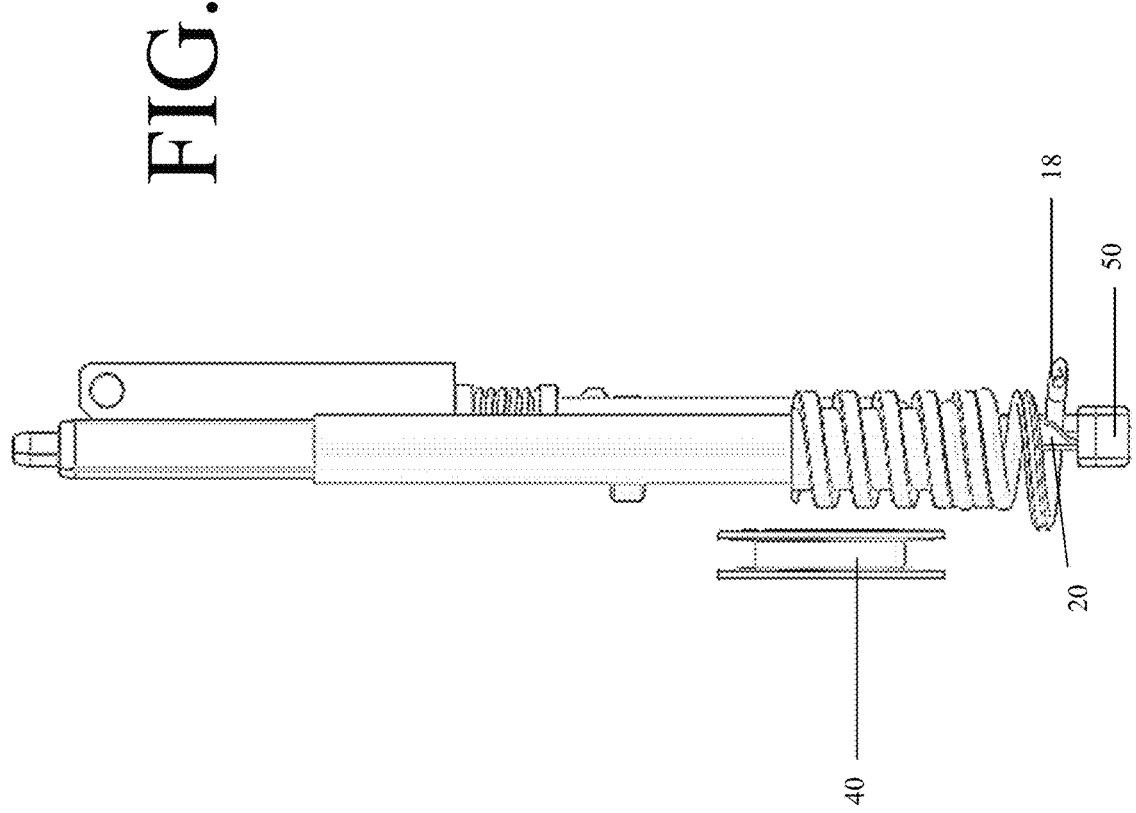

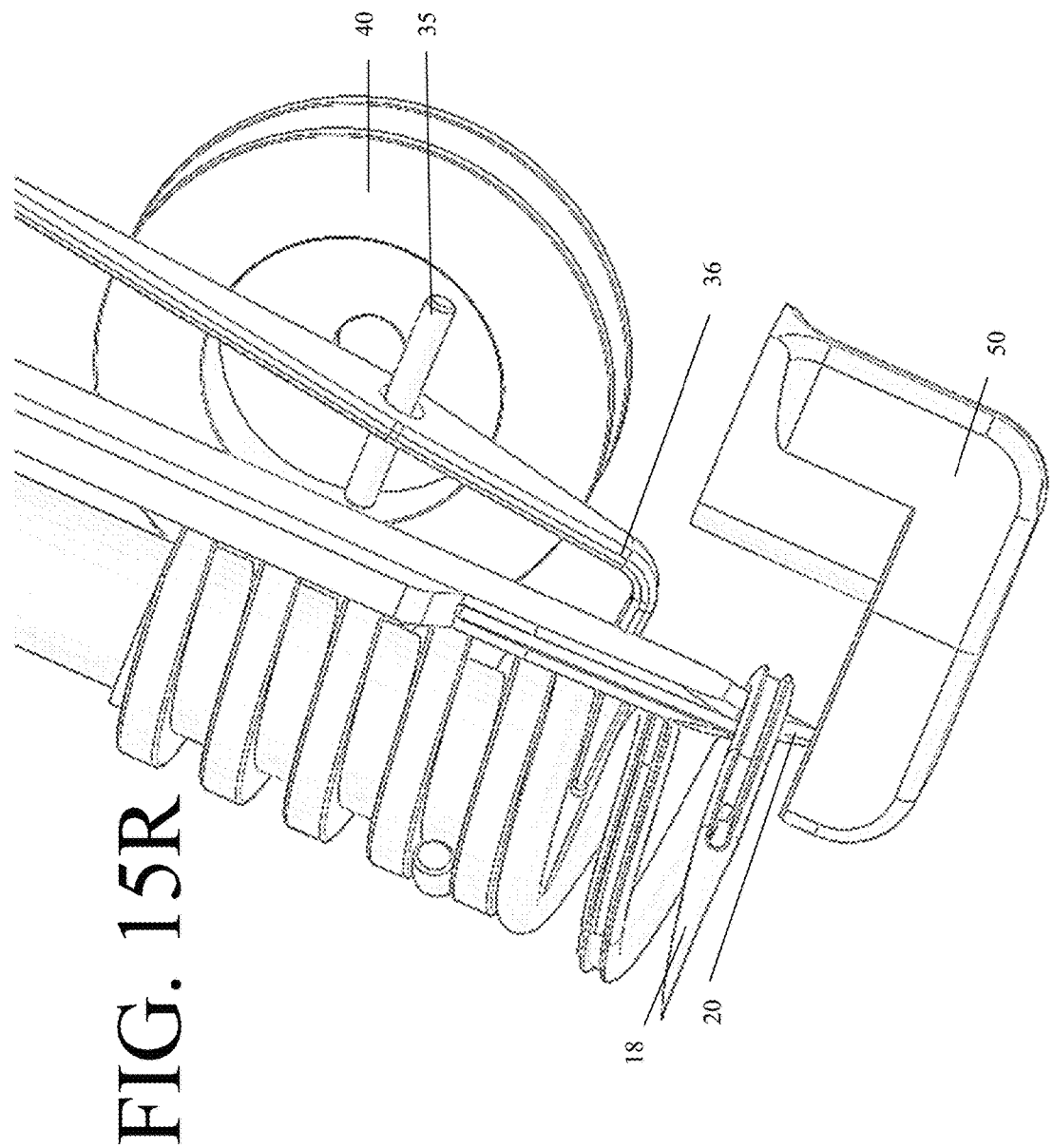

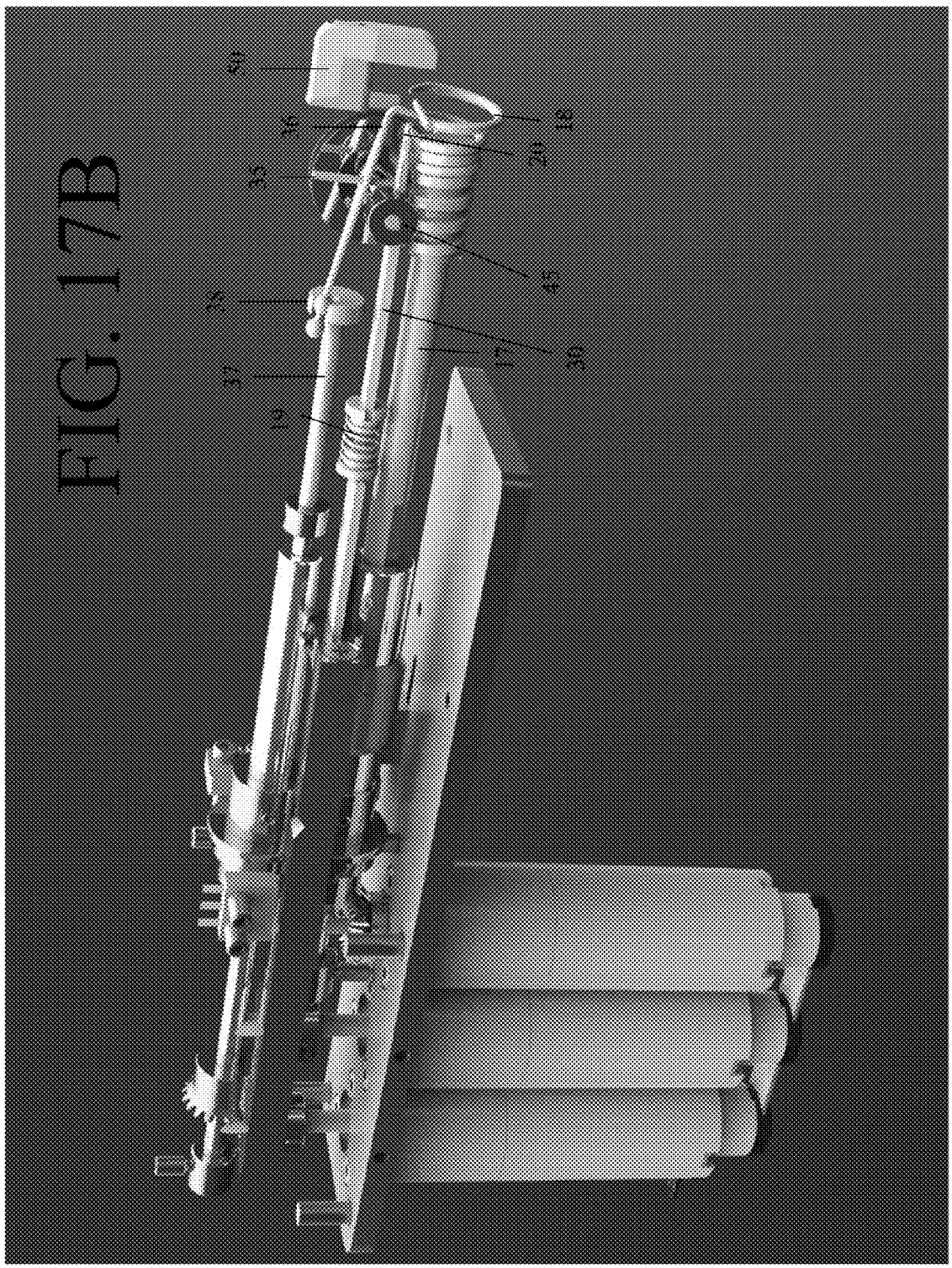

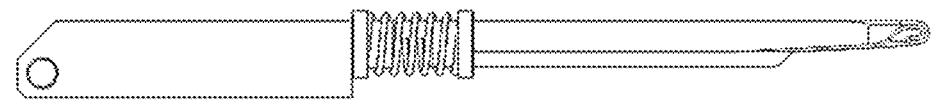
FIG. 20B Compound Needle Closed Position

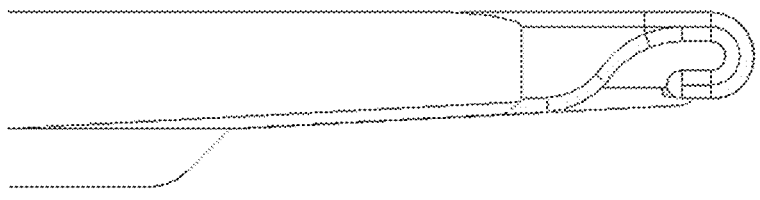
FIG. 20C — Compound Needle Closed Position-Detailed

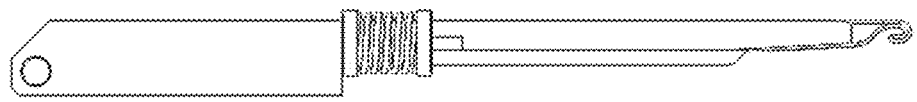
FIG. 20D — Compound Needle Open Position

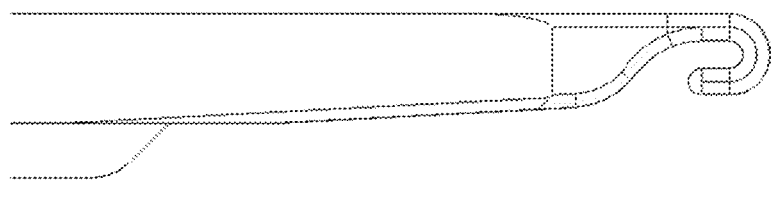
FIG. 20E  Compound Needle Open Position-Detailed

Head 90deg foot

DEVICES AND METHODS FOR CONTINUOUS SURGICAL SUTURING

CROSS REFERENCE TO RELATED APPLICATIONS

This application is a continuation of U.S. application Ser. No. 14/605,402, filed Jan. 26, 2015, now U.S. Pat. No. 9,775,602, which is a continuation-in-part of U.S. patent application Ser. No. 13/898,103, filed May 20, 2013, now U.S. Pat. No. 9,220,498, which is a divisional of U.S. patent application Ser. No. 13/012,965, filed Jan. 25, 2011, now U.S. Pat. No. 8,465,504, each of which is hereby incorporated by reference in its entirety.

BACKGROUND OF THE INVENTION

1. Field of the Invention

The present invention relates to surgical suturing methods and devices, and particularly to devices, machines, methods, needles, and stitch designs for cosmetic-grade suturing for reduced or minimized scarring and/or for organ or tissue internal suturing.

2. Description of the Prior Art

It is generally known in the prior art to provide specialized needles and devices for suturing and for use with suture materials. Prior art patent documents include the following: U.S. Pat. No. 67,545 issued Aug. 6, 1867 for a spiral fissure needle; U.S. Pat. No. 196,226 issued Oct. 16, 1877 for a corkscrew; U.S. Pat. No. 242,602 issued Jun. 7, 1881 for a corkscrew; U.S. Pat. No. 349,791 issued Sep. 28, 1886 for a suture instrument; U.S. Pat. No. 919,138 issued Apr. 20, 1909 for a surgical needle; U.S. Pat. No. 1,583,271 issued May 4, 1926 for a surgical instrument; U.S. Pat. No. 2,327,353 issued Aug. 24, 1943 for an instrument for suturing; U.S. Pat. No. 2,959,172 issued Nov. 8, 1960 for a self-threading suture instrument; U.S. Pat. No. 3,037,619 issued Jun. 5, 1962 for suture devices.

Also, it is known in the prior art to include a tubular needle configuration, such as in U.S. Pat. No. 4,204,541 issued May 27, 1980 for a surgical instrument for stitching up soft tissues with lengths of spiked suture material describes a surgical instrument for stitching up soft tissues with lengths of spiked suture material that include a hollow body which houses a tubular needle having a through bore adapted to accommodate said length of suture material to be introduced into the tissue being sutured along with the needle, and a stop stationary with respect to the body and accommodated inside the through bore of the needle. Both the needle and the stop are shaped as coils having the same diameter and lead, and the needle is mounted slidably along the stop so as to retain the length of suture material in the tissue being sutured while extracting the needle therefrom.

It is also provided in the prior art to provide suturing instruments, such as the following:

U.S. Pat. No. 4,440,171 issued Apr. 3, 1984 for a suturing instrument and a method of holding a shuttle describes a surgical suturing instrument that crosses and knots a suturing thread combining a shuttle and the other suturing thread passing through an eye of a curved needle in a lock stitching practice, for accomplishing smooth passage of passing the shuttle through a loop of the needle thread and exact combination of the shuttle thread and the needle thread without getting out the shuttle from a shuttle holder during the suturing operation so as to form sound suturing stitchings every time. The shuttle is accommodated between a shuttle holder and a shuttle claw. The shuttle is formed with a front end portion movable between a guide groove in the shuttle claw and a guide groove in the shuttle holder. The shuttle is further formed with a sharp end for catching a thread loop in the suturing operation.

U.S. Pat. No. 4,465,070 issued Aug. 14, 1984 for a stitching formation by a suturing instrument describes a suturing instrument used to form stitchings including stitching formation made by causing a shuttle thread to move in reciprocation on cut edges of a human part, between knottings and next knottings in a lock stitching, via an outer side of a needle thread at a needle-out-hole from a needle-in-hole of a needle, thereby to make conglutination of the cut part stable and sound.

U.S. Pat. No. 4,524,771 issued Jun. 25, 1985 for a multiple curved surgical needle describes a needle which includes a plurality of curves which provide for improved control while suturing.

U.S. Pat. No. 4,641,652 issued Feb. 10, 1987 for a applicator for tying sewing threads describes an applicator for utilization in combination with an endoscope tube includes a coil connected to a longitudinal passage through a shaft and comprising hollow turns connected to the shaft passage for reception of a sewing thread, whose proximal extremity is passed through a loop projecting from a radial opening at the distal extremity of the shaft, is then drawn through the shaft passage and fastened to the proximal shaft extremity. Tying the single stitch after piercing the tissues is performed by passing the needle axially through the coil and then around the thread and twisting the coil out of the loop formed thereby to form the first half of a knot which is then complemented by the second half of the knot tied in the same way, the knot being tied by subsequently pulling together the two said halves.

U.S. Pat. No. 4,969,892 issued Nov. 13, 1990 for a suturing anchoring device for use in a female suspension procedure describes an anchoring means for anchoring a suture in tissue includes a housing, a substantially cylindrical means within said housing for receiving a suture, and an adjusting means. Another anchoring means includes a housing, a rotating spool within said housing, a driving gear, and an adjusting means.

U.S. Pat. No. 5,152,769 issued Oct. 6, 1992 for an apparatus for laparoscopic suturing with improved suture needle describes a novel suturing assembly defined by a new and improved suturing needle, having a bore therethrough for forming an arc of thread to be grasped. The assembly would comprise a first and second barrel portion, the portions working to allow a rod member to secure the arc of thread formed, and hold it in place, while the needle forms a second suture, and secures the loop as part of the suture.

U.S. Pat. No. 5,356,424 issued Oct. 18, 1994 for a laparoscopic suturing device describes a laparoscopic suturing device that includes a suturing needle and a driver for manipulating the needle.

U.S. Pat. No. 5,499,991 issued Mar. 19, 1996 for an endoscopic needle with suture retriever describes a suture retriever and method for manipulating suture during endoscopic surgical procedures.

U.S. Pat. No. 5,507,743 issued Apr. 16, 1996 for a coiled RF electrode treatment apparatus describes an RF treatment apparatus provides multi-modality treatment for tumors and other desired tissue masses, and includes an RF indifferent electrode and an active electrode.

U.S. Pat. No. 5,520,703 issued May 28, 1996 for a laparoscopic deschamp and associated suturing technique describes a laparoscopic suturing device with an elongate shaft having a distal end and a proximal end and an arcuate tissue piercing element permanently fixed to the shaft at the distal end, the arcuate tissue piercing element lying in a plane disposed substantially transversely to the shaft. The tissue piercing element is provided at a free end, spaced from the shaft, with an eyelet, and the device has a suture thread extending through the eyelet.

U.S. Pat. No. 5,562,685 issued Oct. 8, 1996 for a surgical instrument for placing suture or fasteners and U.S. Pat. No. 5,709,692 issued Jan. 20, 1998 for a surgical instrument for placing suture or fasteners at a remote location such as a laparoscopic surgery. The instrument is an elongated handle having a coiled projection at its distal end. The coiled projection is employed in penetrating and positioning a length of suture or fastener in tissue, for example, as in tissue proximation.

U.S. Pat. No. 5,810,851 issued Sep. 22, 1998 for a suture spring device describes a guide used to position a suture spring device in anatomical tissue in an elastically deformed, expanded state and is subsequently removed to permit the suture spring device to move from the elastically deformed, expanded state toward a relaxed, contracted state to apply a predetermined compression to the tissue engaged by the device.

U.S. Pat. No. 5,911,689 issued Jun. 15, 1999 for a subcutaneous radiation reflection probe describes a subcutaneous radiation reflection probe for measuring oxygen saturation in living tissue includes an elongate drive shaft on one end of which is detachably coupled a mounting cup.

U.S. Pat. No. 5,935,138 issued Aug. 10, 1999 for a spiral needle for endoscopic surgery describes a needle for endoscopic surgery is curved into an arc of more than 180.degree. And twisted, so that it forms a part of a spiral, with a lateral offset between the needle point and barrel.

U.S. Pat. No. 5,947,983 issued Sep. 7, 1999 for a tissue cutting and stitching device and method describes a device for cutting tissue, the device comprising a first tube having a side window; a second tube positioned within the first tube, the second tube having a side window and being movable within the first tube; a third tube positioned within the second tube, the third tube having a side window and being movable within the second tube; and a needle insertable within the second tube, the needle housing a suture.

U.S. Pat. No. 6,113,610 issued Sep. 5, 2000 for a device and method for suturing wound describes a needle assembly in which the needle is constructed of a spring-like material and initially housed within a sheath in a deformed condition. The needle can be easily exposed by sliding an actuator so as to release the constraining means and allow the needle to assume its undeformed condition.

U.S. Pat. No. 6,520,973 issued Feb. 18, 2003 for an anastomosis device having an improved needle driver describes an anastomosis device for attaching a first hollow vessel to a second hollow vessel. The device includes a handle for holding the device, and a head assembly, attached to the handle, for holding the first and second hollow vessels adjacent to each other. The head assembly having a distal end, a proximal end and a longitudinal axis there between. The device further includes a needle guide disposed longitudinally along the head assembly adjacent to the vessels, and a helical needle, having a suture attached to a proximal end thereof, disposed within the head assembly at its proximal end. The device has an actuator on the handle for actuating a needle driver. The needle driver is coupled to the head and includes a flexible rotatable member operated by the actuator, for rotating and driving the needle distally along the needle guides and through the first and second hollow vessels.

U.S. Pat. No. 6,537,248 issued Mar. 25, 2003 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid. The surgical apparatus includes an elongated device forming a helical needle.

U.S. Pat. No. 6,562,052 issued May 13, 2003 for a suturing device and method that allows a physician to remotely suture biological tissue.

U.S. Pat. No. 6,613,058 issued Sep. 2, 2003 for an anastomosis device having needle receiver for capturing the needle after it has passed through the needle guide.

U.S. Pat. No. 6,626,917 issued Sep. 30, 2003 for a helical suture instrument which either pushes or pulls a suture along a helical needle tract.

U.S. Pat. No. 6,663,633 issued Dec. 16, 2003 for a helical orthopedic fixation and reduction device, insertion system, and associated methods describes a system for fixation of a soft tissue tear includes a flexible, generally helical fixation element biased to a predetermined pitch and a hollow, generally helical insertion element dimensioned to admit at least a distal portion of the fixation element into a lumen thereof.

U.S. Pat. No. 6,723,107 issued Apr. 20, 2004 for a method and apparatus for suturing describes devices and techniques for suturing that are particularly useful in laparoscopic, arthroscopic, and/or open surgical procedures. A method of delivering a suture includes providing a suture device, releasably coupling a suture to a distal end of a suture device by threading the suture through a first region of a bounded opening of the suture device and moving the suture to a second region of the bounded opening having a dimension smaller than a diameter of the suture to trap the suture in the second region, penetrating a substrate with the distal end of the suture device such that the a portion of the suture passes through the substrate, and releasing the suture from the distal end of the suture device.

U.S. Pat. No. 6,911,003 issued Jun. 28, 2005 for transobturator surgical articles and methods describe surgical articles, implants and components suitable for a transobturator surgical procedure.

U.S. Pat. No. 6,911,019 issued Jun. 28, 2005 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 6,911,037 issued Jun. 28, 2005 for a retrievable septal defect closure device describes a septal defect closure device having a first occluding disk having a first flexible membrane attached to a first frame and a second occluding disk having a second flexible membrane attached to a separate second frame. The first frame has at least two outwardly extending loops joined to one another by flexible joints. These loops are attached to the first membrane to define taut fabric petals when the first disk is in a deployed configuration.

U.S. Pat. No. 6,923,807 issued Aug. 2, 2005 for a helical device and method for aiding the ablation and assessment of tissue describes a helical needle attached to a surgical probe to aid in the insertion of the probe into a tissue mass.

U.S. Pat. No. 6,986,776 issued Jan. 17, 2006 for a suturing apparatus, method and system describes an apparatus used with a helical suture device has a first end and a second end.

The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

U.S. Pat. No. 7,070,556 issued Jul. 4, 2006 for transobturator surgical articles and methods describe a surgical instrument and method for treating female urinary stress incontinence. The instrument includes a first curved needle-like element defining in part a curved shaft having a distal end and a proximal, a mesh for implanting into the lower abdomen of a female to provide support to the urethra; a second curved needle element having a proximal end and a distal end, and a coupler for simultaneous attachment to the distal end of the first needle and the distal end of the second needle.

U.S. Pat. No. D543,626 issued May 29, 2007 for a handle for a surgical instrument describes an ornamental design for a handle for a surgical instrument U.S. Pat. No. 7,235,087 issued Jun. 26, 2007 for an articulating suturing device and method describes devices, systems, and methods for suturing of body lumens allow the suturing of vascular puncture sites located at the distal end of a percutaneous tissue tract.

U.S. Pat. No. 7,269,324 issued Sep. 11, 2007 for a helical fiber optic mode scrambler describes methods and apparatus of the present invention provide advantages for remote laser delivery systems that conduct high levels of light energy through a fiber optic cable to a selectable target surface.

U.S. Pat. No. 7,288,105 issued Oct. 30, 2007 for a tissue opening occluder describes a tissue opening occluder including first and second occluder portions, each occluder portion including a frame structure and an attachment structure to attach one portion to the other portion. The frames may be utilized to constrain the tissue between the two portions enough to restrict the significant passage of blood therethrough.

U.S. Pat. No. 7,290,494 issued Nov. 6, 2007 for a method for manufacturing stent-grafts describes a sewing machine which is capable of sewing reinforcing wire to tubular grafts in order to form stent grafts. A bobbin (which may be seated in a shuttle) carries a bottom thread through the bore of the tubular graft and forms a stitch in combination with a top thread carried on a needle which pierces the graft wall.

U.S. Pat. No. 7,309,325 issued Dec. 18, 2007 for a helical needle apparatus for creating a virtual electrode used for the ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 7,323,004 issued Jan. 29, 2008 for a device for providing automatic stitching of an incision describes an automatic suturing device including: a body for insertion into an opening in tissue; a plurality of hooks movably disposed in the body between retracted and extended positions; a suture holder having sutures disposed therein, the suture holder having a mechanism for engaging a portion of the hooks when in the retracted position and for attaching the sutures to a portion of the plurality of hooks; and an actuator for actuating the plurality of hooks from the retracted position to the extended position and for embedding the exposed plurality of hooks with the attached sutures into the tissue surrounding the opening.

U.S. Pat. No. 7,335,221 issued Feb. 26, 2008 for a suture anchoring and tensioning device and method for using same describes a suture anchoring device made from a coiled member having a helical configuration with a multiplicity of turns. When used in connection with a surgical procedure, the device is positioned adjacent to a wound site and a suture is attached to at least two of the turns so as to anchor the suture to the coiled member.

U.S. Pat. No. 7,347,812 issued Mar. 25, 2008 for prolapse repair instruments.

U.S. Pat. No. 7,351,197 issued Apr. 1, 2008 for a method and apparatus for cystocele repair describes comprising the steps of: establishing four pathways in tissue around a bladder of a patient, introducing a strap into each of said pathways, and positioning beneath said bladder of said patient a support member having each said strap connected thereto such that said bladder of said patient is supported by said support member and a bulge of said bladder into a vagina of said patient is reduced.

U.S. Pat. No. 7,357,773 issued Apr. 15, 2008 for a handle and surgical article describes handles for needles suitable for pelvic floor surgical procedures.

U.S. Pat. No. 7,371,244 issued May 13, 2008 for a deployment apparatus for suture anchoring device describes a deployment device for anchoring a suture to a suture anchoring device, which is made from a helically coiled member, includes a winding tube for winding a suture around the coiled member in a helical path such that the suture is attached to at least one turn of the coiled member.

U.S. Pat. No. 7,377,936 issued May 27, 2008 for a retrievable septal defect closure device describes a septal defect closure device having a first occluding disk having a first flexible membrane attached to a first frame and a second occluding disk having a second flexible membrane attached to a separate second frame. The first frame has at least two outwardly extending loops joined to one another by flexible joints. These loops are attached to the first membrane to define taut fabric petals when the first disk is in a deployed configuration.

U.S. Pat. No. 7,479,155 issued Jan. 20, 2009 for a defect occluder release assembly and method describes a release assembly is provided to aid the reversible and repositionable deployment of a defect occluder. The release assembly includes an occluder tether having a distal portion comprising at least one suture loop, and a snare structure having a distal portion comprising a snare element. The at least one suture loop is receivable through at least a portion of the defect occluder, and reversibly looped over an anchor element so as to permit reversible collapse the defect occluder for selective ingress and egress from a delivery catheter. The snare element is reversibly engageable with the anchor element so as to reversibly retain the at least one suture loop upon the anchor element, and thereby hold the defect occluder in a posture for reversible free-floating tethered deployment in a defect while being observable in a final position prior to release.

U.S. Pat. No. 7,500,945 issued Mar. 10, 2009 for a method and apparatus for treating pelvic organ prolapse describes the steps of establishing a first pathway between the external perirectal region of the patient to the region of the ischial spine in tissue on one side of the prolapsed organ, followed by establishing a second pathway in tissue on the contralateral side of the prolapsed organ. A support member, which includes a central support portion and two end portions, is positioned in a position to reposition said prolapsed organ in said organ's anatomically correct location. The end portions of the support member are introduced through the respective tissue pathways, followed by adjustment of the end portions so that the support member is located in a therapeutic relationship to the prolapsed organ that is to be supported.

U.S. Pat. No. 7,582,103 issued Sep. 1, 2009 for a tissue opening occluder describes a tissue opening occluder comprising first and second occluder portions, each occluder portion including a frame structure and an attachment structure to attach one portion to the other portion. The frames may be utilized to constrain the tissue between the two portions enough to restrict the significant passage of blood therethrough.

U.S. Pat. No. 7,588,583 issued Sep. 15, 2009 for a suturing device, system and method describes improved medical suturing devices, systems, and methods to hold a suture needle at a fixed location relative to a handle of the device, allowing the surgeon to grasp and manipulate the handle of the suturing device to insert the needle through tissues in a manner analogous to use of a standard needle gripper.

U.S. Pat. No. 7,637,918 issued Dec. 29, 2009 for a helical suturing device describes an apparatus for repairing a tear in an annulus fibrosus of a spinal disc includes a hollow, helically-shaped suturing needle and a retriever.

U.S. Pat. No. 7,686,821 issued Mar. 30, 2010 for an apparatus and method for positive closure of an internal tissue membrane opening describes a device having two components: a needle advancing apparatus slidable longitudinally along a catheter to advance needles into a tissue membrane, such as a blood vessel wall, around an opening in the membrane; and, a suture retrieval assembly insertable through the catheter beyond a distal side of the tissue membrane.

U.S. Pat. No. 7,699,805 issued Apr. 20, 2010 for a helical coil apparatus for ablation of tissue describes a surgical apparatus for delivering a conductive fluid to a target site for subsequent formation of a virtual electrode to ablate bodily tissue at the target site by applying a current to the delivered conductive fluid.

U.S. Pat. No. 7,699,857 issued Apr. 20, 2010 for a hydrodynamic suture passer describes a hydrodynamic suturing instrument, comprises an elongated cannulated suturing needle having a distal end configured to carry a suture through tissue and a proximal end adapted to connect to a syringe barrel and a lumen extending from said proximal end to an opening at the distal end for having a size for the passage of a suture, and the opening at the distal end configured to receive a suture extending from the lumen along an outer surface of the needle wherein a sharp point extends forward of the suture. A companion instrument includes forceps having a distal end with jaws and a proximal end with a lumen extending from the proximal end to the distal end for passage of the needle, and the jaws having an opening enabling passage of the needle through tissue grasped in the jaws.

U.S. Pat. No. 7,699,892 issued Apr. 20, 2010 for a minimally invasive procedure for implanting an annuloplasty device describes a method for modifying a heart valve annulus includes placing a purse string suture at a puncture site adjacent a heart valve, inserting at least one delivery member through the puncture site, positioning a distal end of the at least one delivery member adjacent a portion of a valve annulus, deploying an annuloplasty device carried within the at least one delivery member and implanting the annuloplasty device into the valve annulus. The method also includes reshaping the heart valve annulus after implantation of the at least one annuloplasty device.

U.S. Pat. No. 7,776,059 issued Aug. 17, 2010 for a suturing method describes an apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

U.S. Pat. No. 7,780,700 issued Aug. 24, 2010 for a patent foramen ovale closure system describes a patent foramen ovale closure device, method of delivering and a delivery system are provided. The device may include a closure device releasably connectable to an actuator. The device may include a proximal segment, an intermediate segment and a distal segment. When delivered, the proximal segment and intermediate segment form a first clip-shaped portion sized and configured to be positioned over a septum secundum of the patent foramen ovale, and the intermediate segment and distal segment form a second clip-shaped portion sized and configured to be positioned over a septum primum of the patent foramen ovale.

U.S. Pat. No. 7,794,471 issued Sep. 14, 2010 for a compliant anastomosis system describes an integrated anastomosis tool may include an effector that both makes an opening in the wall of a target vessel and connects a graft vessel to the target vessel. The connection between the graft vessel and the target vessel may be compliant, and may be achieved by deploying a plurality of connectors such as staples into tissue.

SUMMARY OF THE INVENTION

The present invention relates to suturing devices, including modules for automatically creating a stitch that is especially useful for cosmetic-grade suturing applications and reducing suturing time.

It is an object of this invention to provide a module constructed and configured for quick attachment to a handle to provide automatic suturing for reduced or substantially minimized scarring and reducing suturing time.

It is another object of this invention to provide a module constructed and configured for quick attachment to a handle to automatically provide subcutaneous stitches.

These and other aspects of the present invention will become apparent to those skilled in the art after a reading of the following description of the preferred embodiment when considered with the drawings, as they support the claimed invention.

FIG. 3A is a perspective view diagram of the portion of the automated machine in a position of operation for completing a stitch automated by the machine of the present invention.

Figure 3:
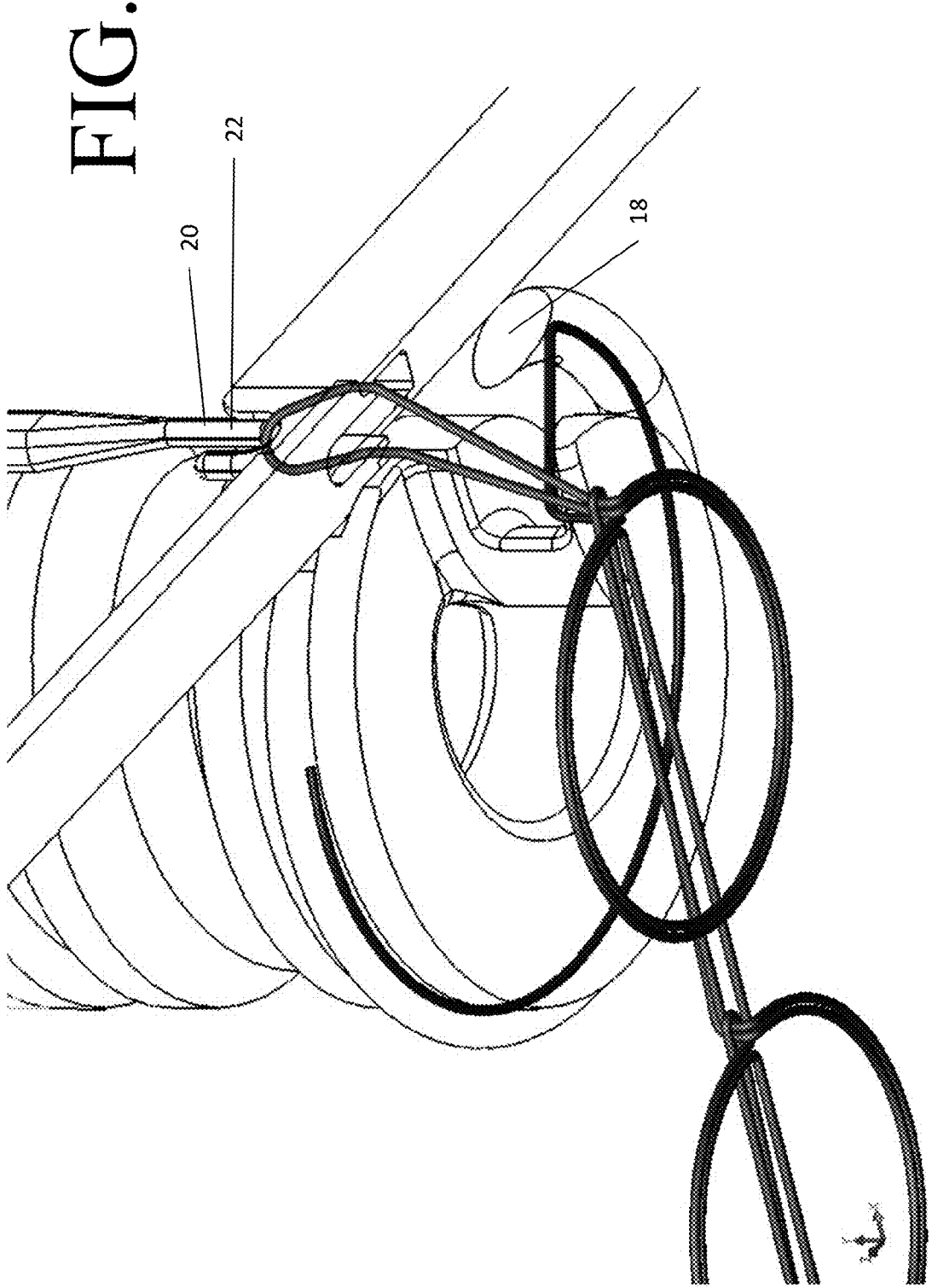
FIG. 3 shows a perspective view diagram illustrating a portion of an automated machine for suturing from FIG. 1 focused on the hook and suture needle interaction for forming continuous suture stitches according to one embodiment of the invention.
Figure 3B:
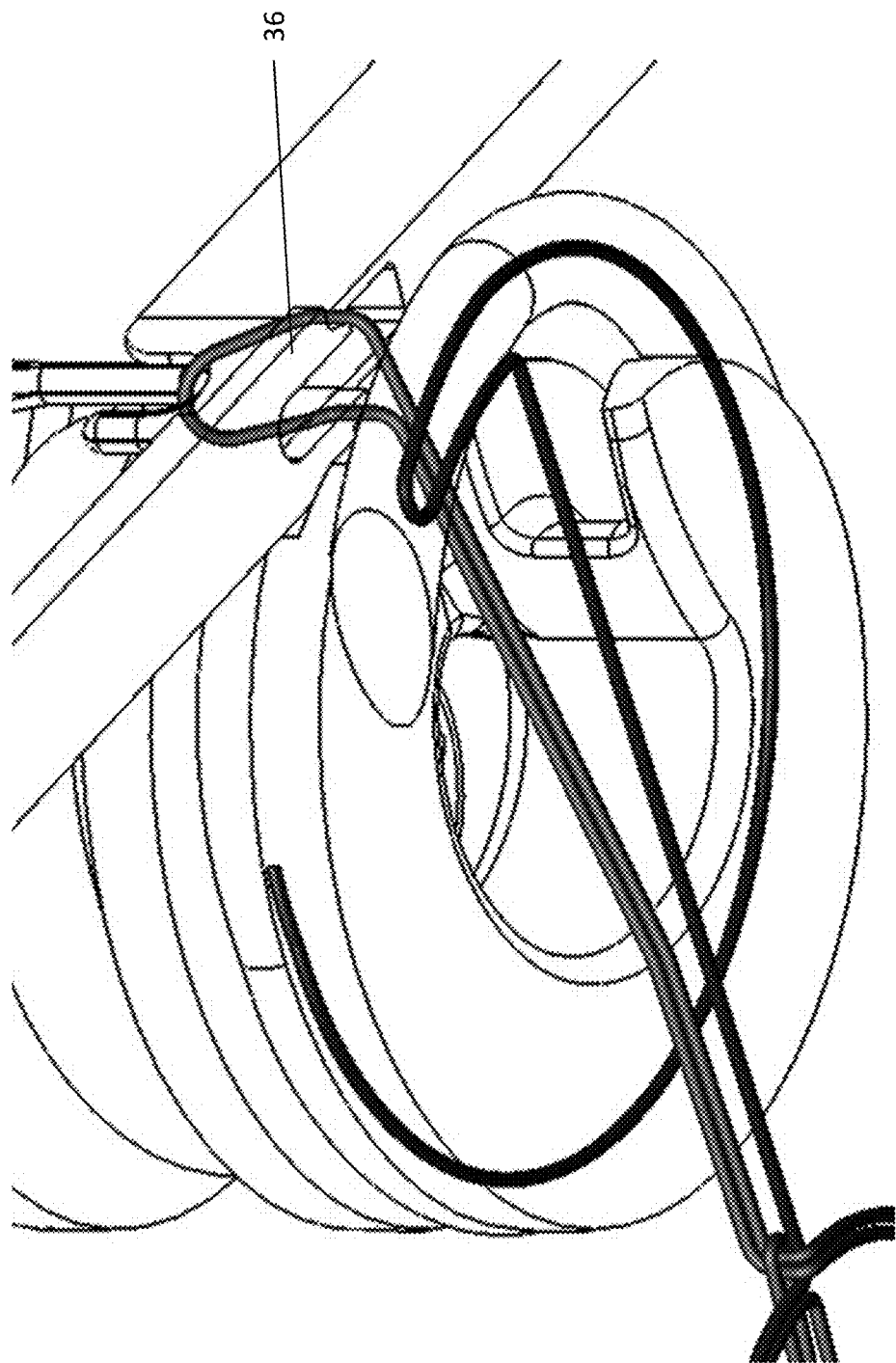

FIG. 3B is a perspective view diagram of the portion of the automated machine in a position of operation for completing a stitch automated by the machine of the present invention.

FIG. 3C is a perspective view diagram of the portion of the automated machine in a position of operation for completing a stitch automated by the machine of the present invention.

FIG. 3D is a perspective view diagram of the portion of the automated machine in a position of operation for completing a stitch automated by the machine of the present invention.

FIG. 3E is a perspective view diagram of the portion of the automated machine in a position of operation for completing a stitch automated by the machine of the present invention.

Figure 3F:
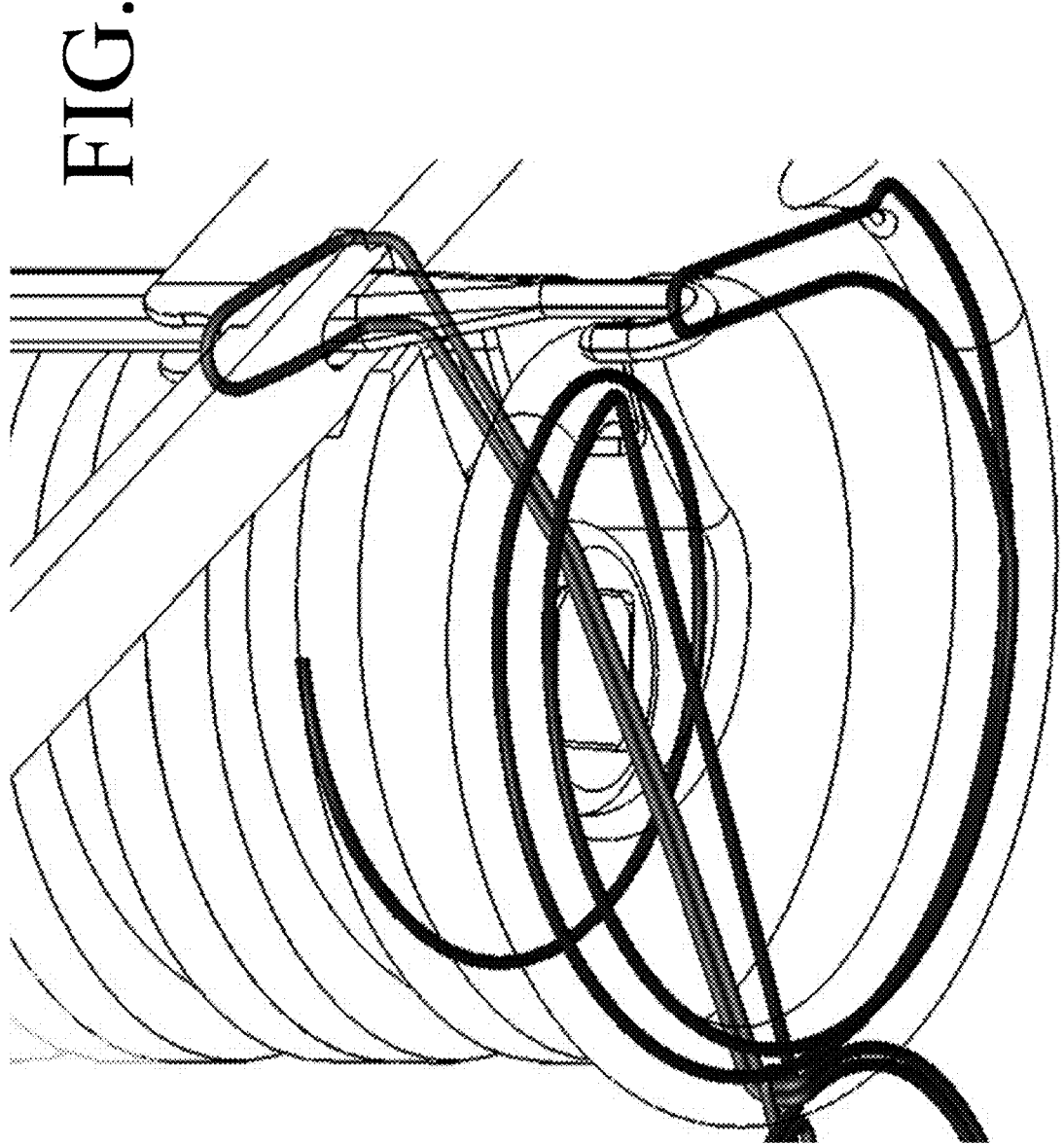

FIG. 3F is a perspective view diagram of the portion of the automated machine in a position of operation for completing a stitch automated by the machine of the present invention.

Figure 3G:
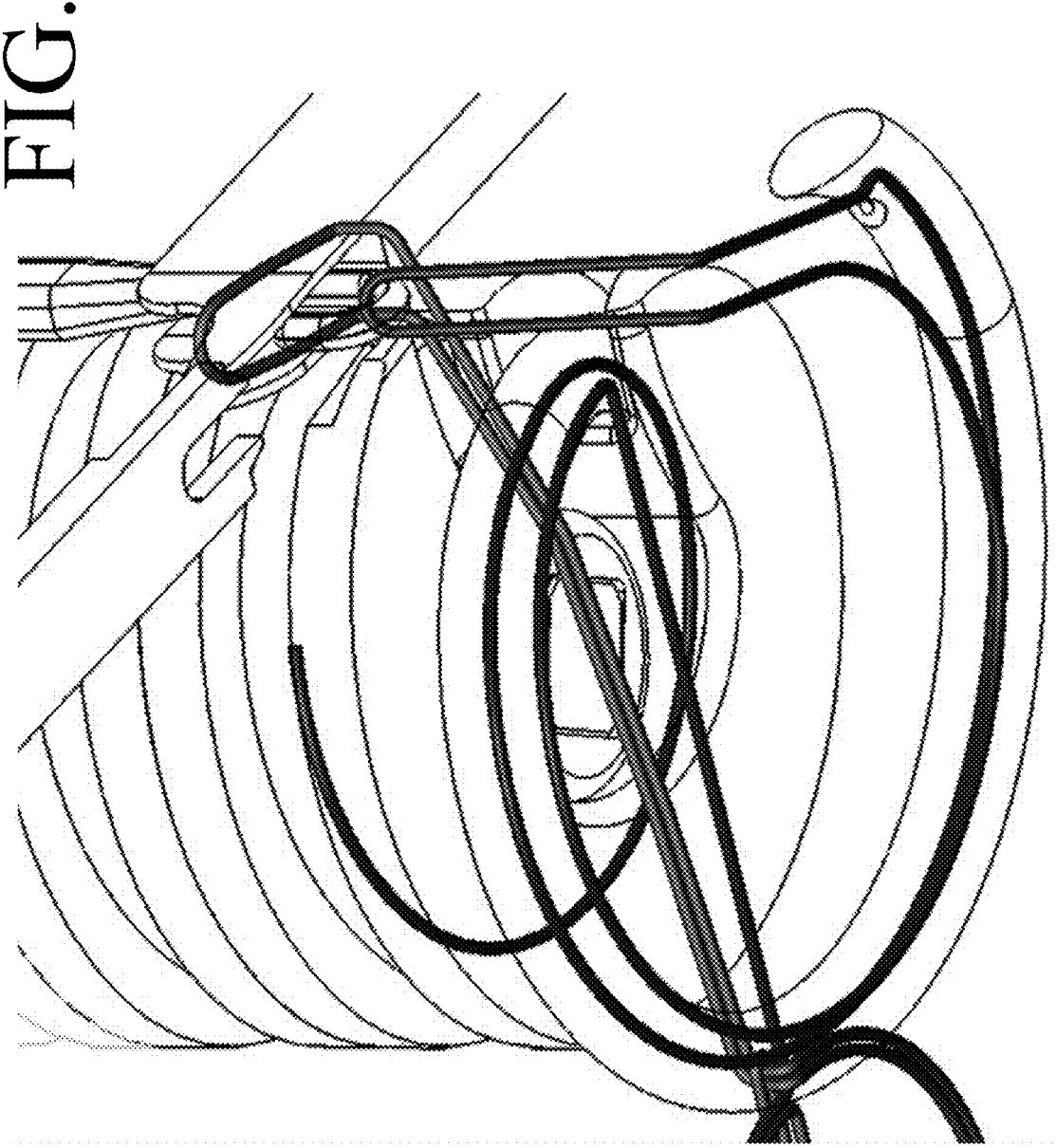

FIG. 3G is a perspective view diagram of the portion of the automated machine in a position of operation for completing a stitch automated by the machine of the present invention.

Figure 3H:
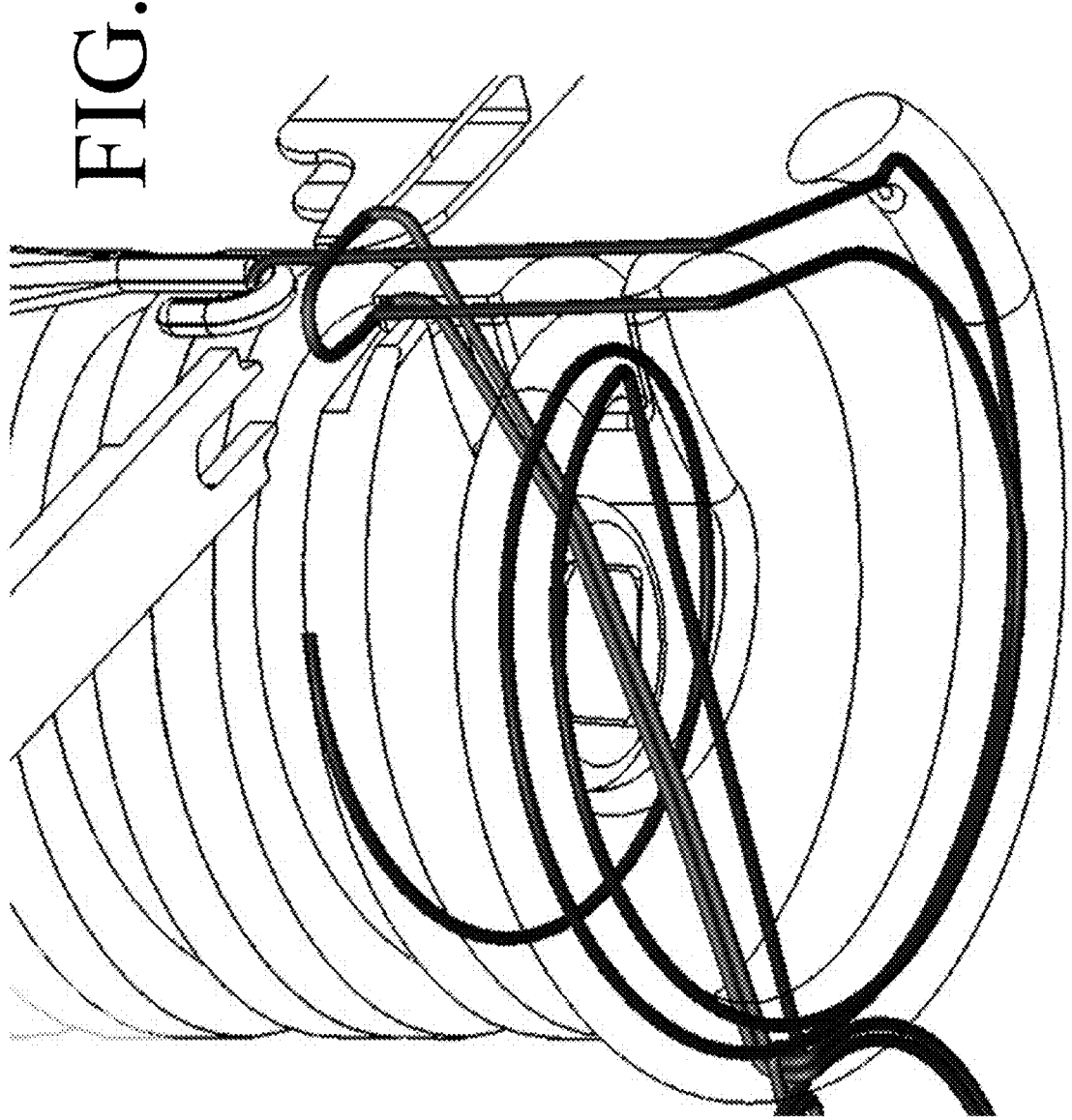

FIG. 3H is a perspective view diagram of the portion of the automated machine in a position of operation for completing a stitch automated by the machine of the present invention.

Figure 3I:
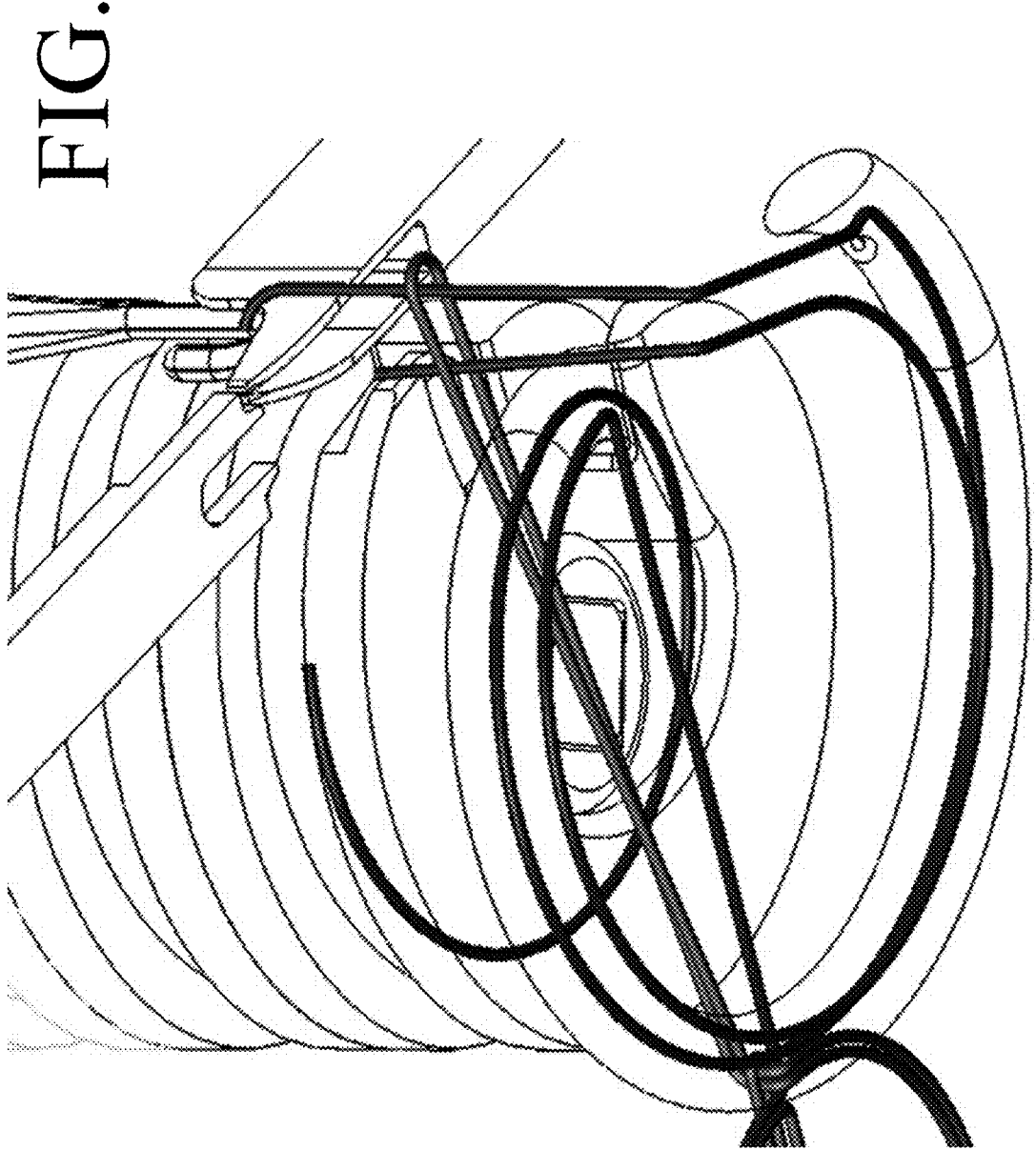

FIG. 3I is a perspective view diagram of the portion of the automated machine in a position of operation for completing a stitch automated by the machine of the present invention.

FIG. 3J is a perspective view diagram of the portion of the automated machine in a position of operation for completing a stitch automated by the machine of the present invention.

Figure 1:
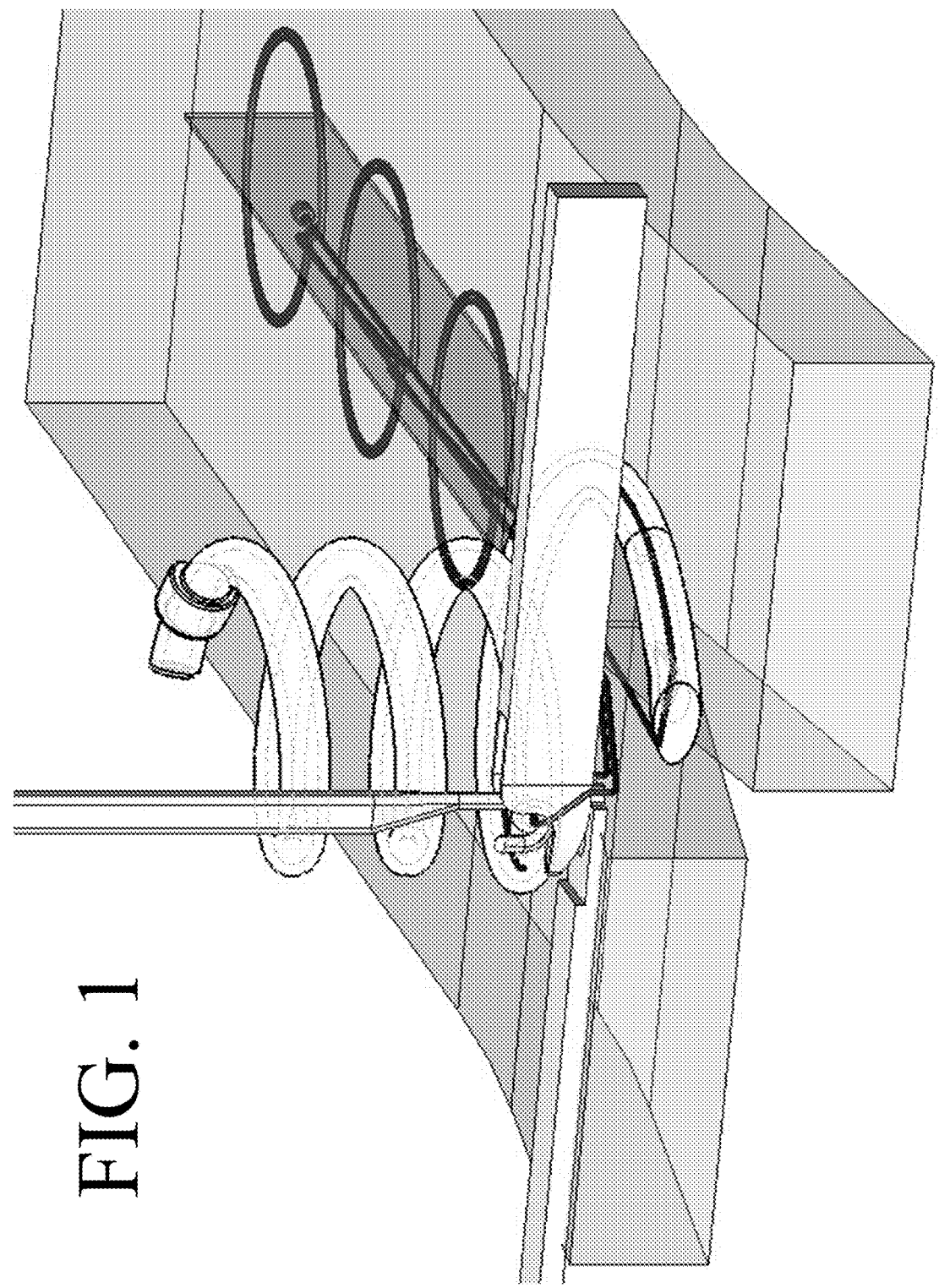
FIG. 1 is a perspective view diagram of the main components of the head of a device for suturing showing skin subcuticular suturing embodiment of the invention.

FIG. 4 shows the offset subcuticular skin suturing mechanism of FIG. 1. with the tip of the helico-spiral suture needle in the home position (outside the skin).

Figure 5:
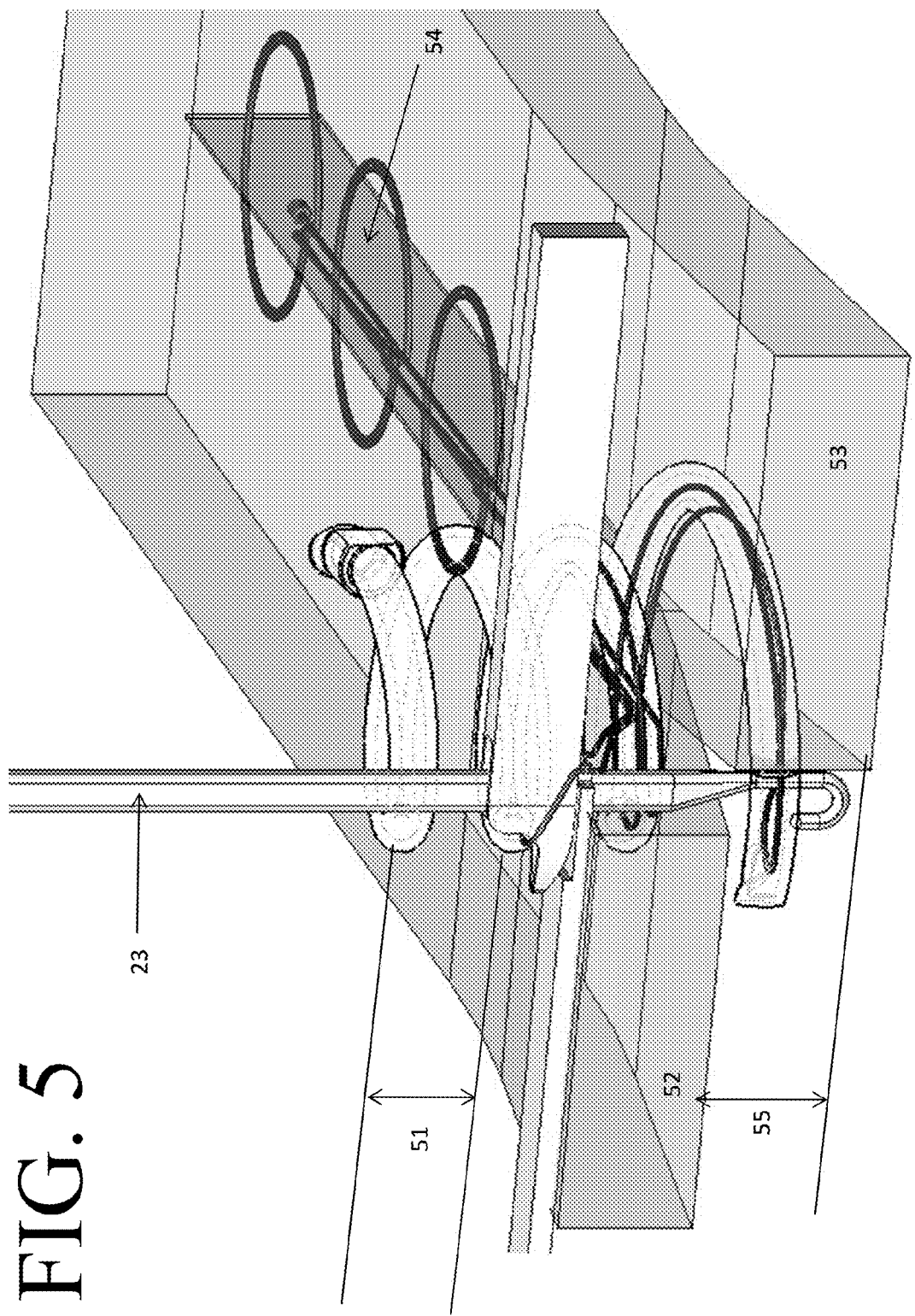

FIG. 5 shows the offset subcuticular skin suturing mechanism of FIG. 1. with the tip of the helico-spiral suture needle in its final position after completing one skin bite.

Figure 6:
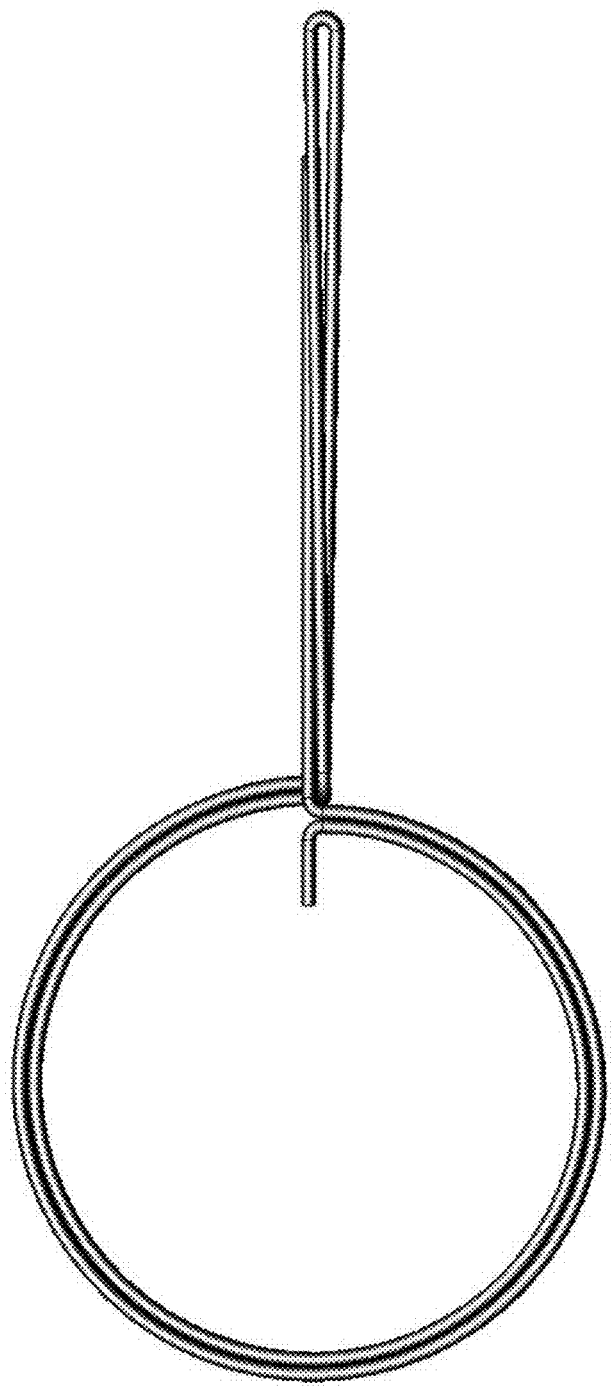

FIG. 6 shows a top view diagram illustrating a stitching pattern for a single unit cycle for making continuous suturing made by an automated machine for suturing according to one embodiment of the invention.

Figure 7A:
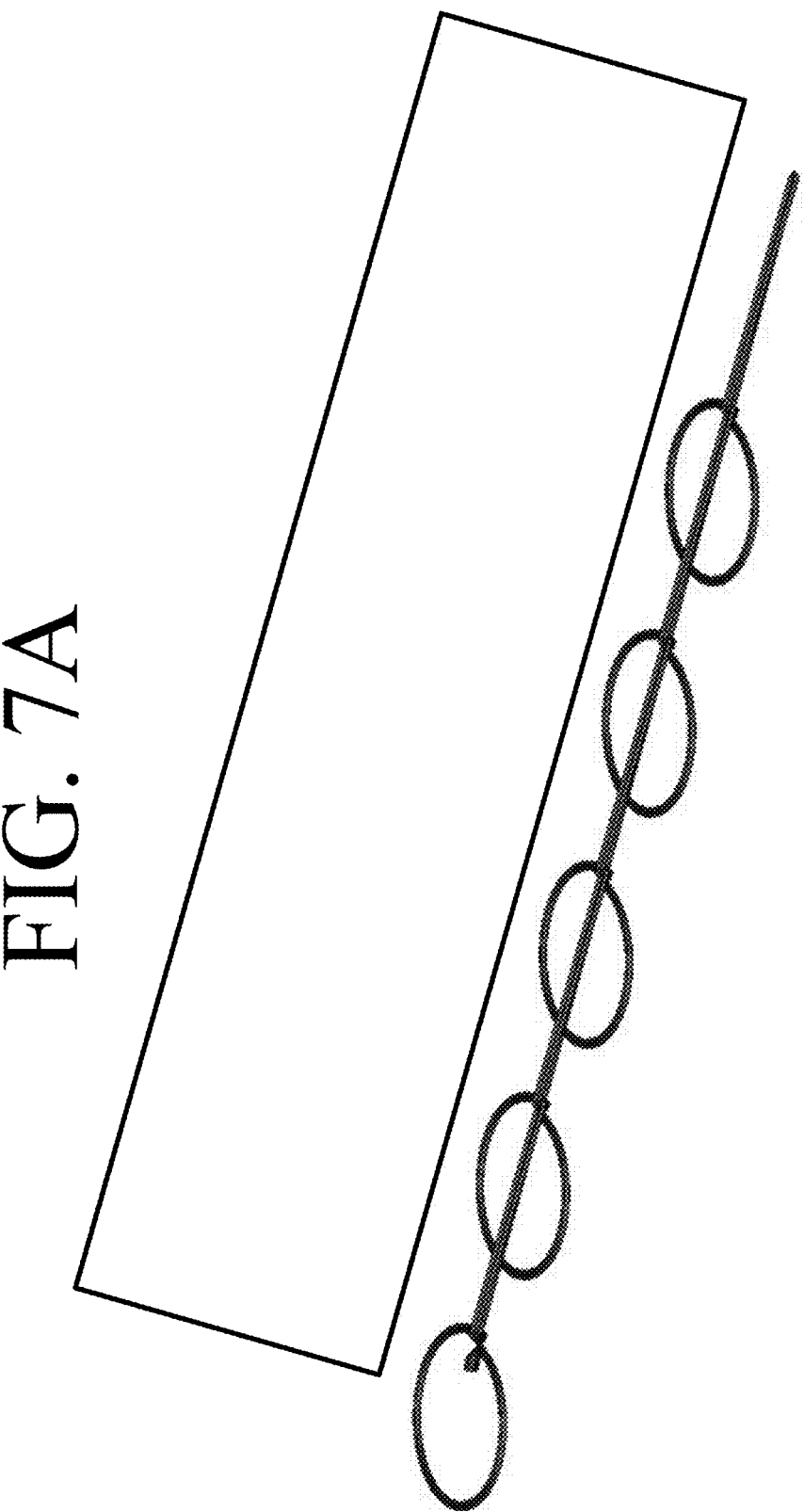

FIG. 7A illustrates a perspective view for continuous suture stitching forming chains of single unit cycles illustrated from FIG. 6.

FIG. 7B illustrates a perspective view for continuous suture stitching forming chains of single unit cycles illustrated from FIG. 6.

Figure 7C:
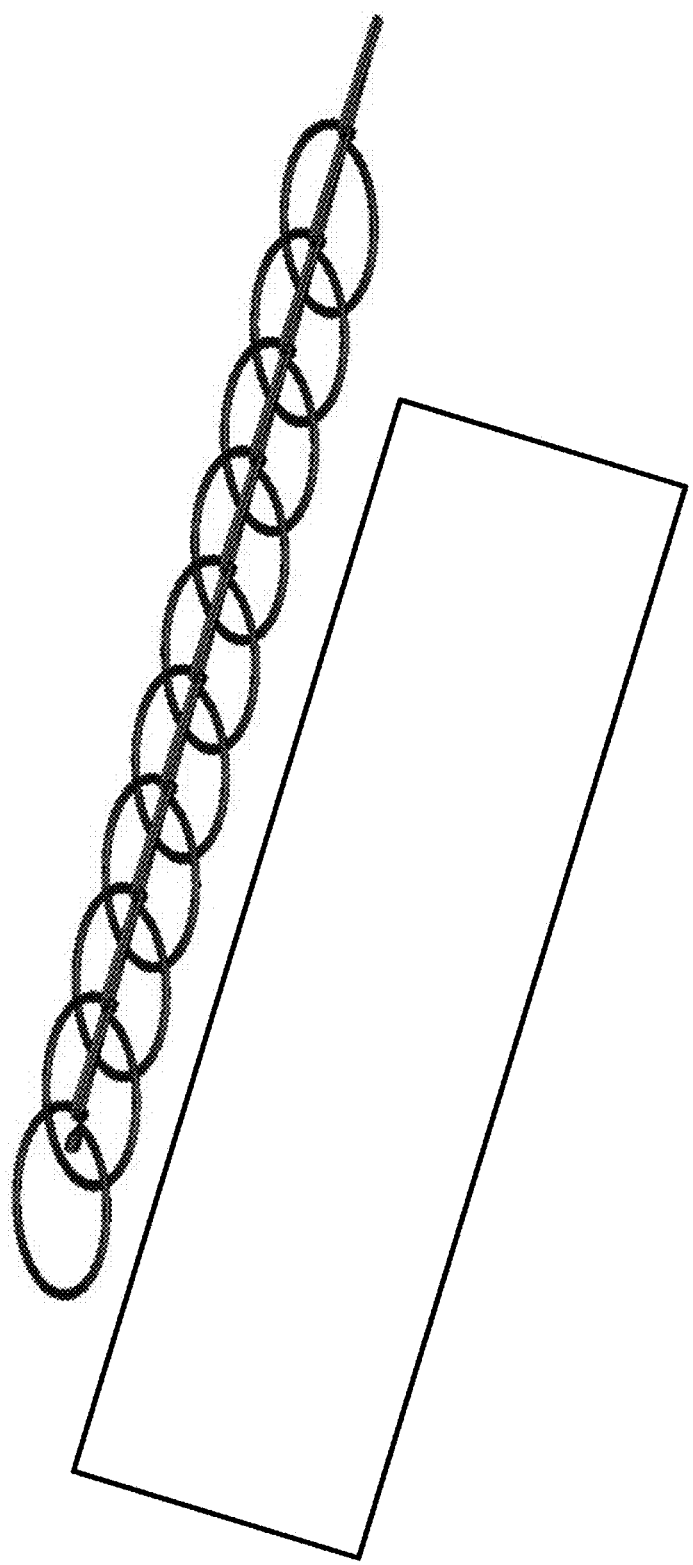

FIG. 7C illustrates a perspective view for continuous suture stitching forming chains of single unit cycles illustrated from FIG. 6.

Figure 8A:
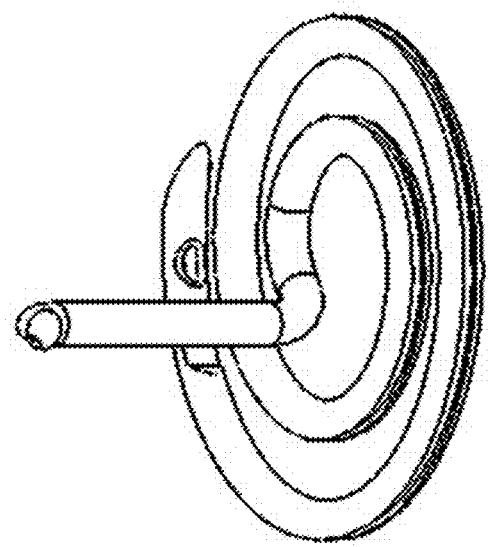

FIG. 8A shows a perspective view illustrating a solid suture needle in alternative embodiments for use in suturing according to the present invention.

Figure 8B:
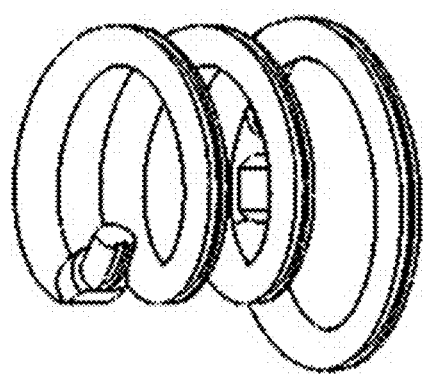

FIG. 8B shows a perspective view illustrating a solid suture needle in alternative embodiments for use in suturing according to the present invention.

Figure 8C:
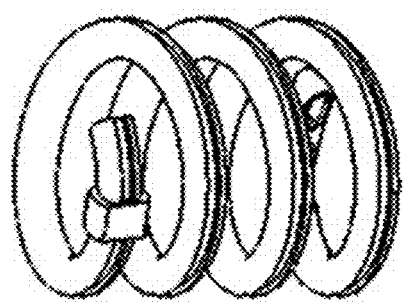

FIG. 8C shows a perspective view illustrating a solid suture needle in alternative embodiments for use in suturing according to the present invention.

Figure 9A:
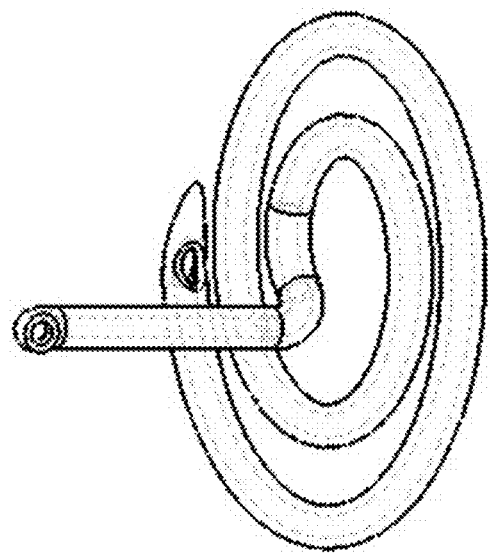

FIG. 9A shows a perspective view illustrating a hollow suture needle in alternative embodiments for use in suturing according to the present invention.

Figure 9B:
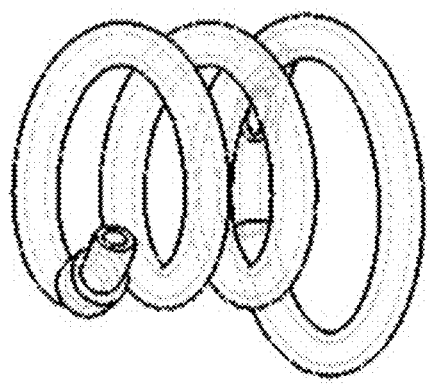

FIG. 9B shows a perspective view illustrating a hollow suture needle in alternative embodiments for use in suturing according to the present invention.

Figure 9C:
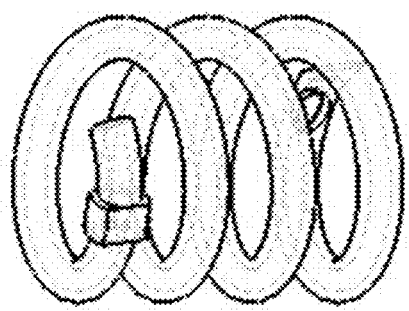

FIG. 9C shows a perspective view illustrating a hollow suture needle in alternative embodiments for use in suturing according to the present invention.

Figure 10A:
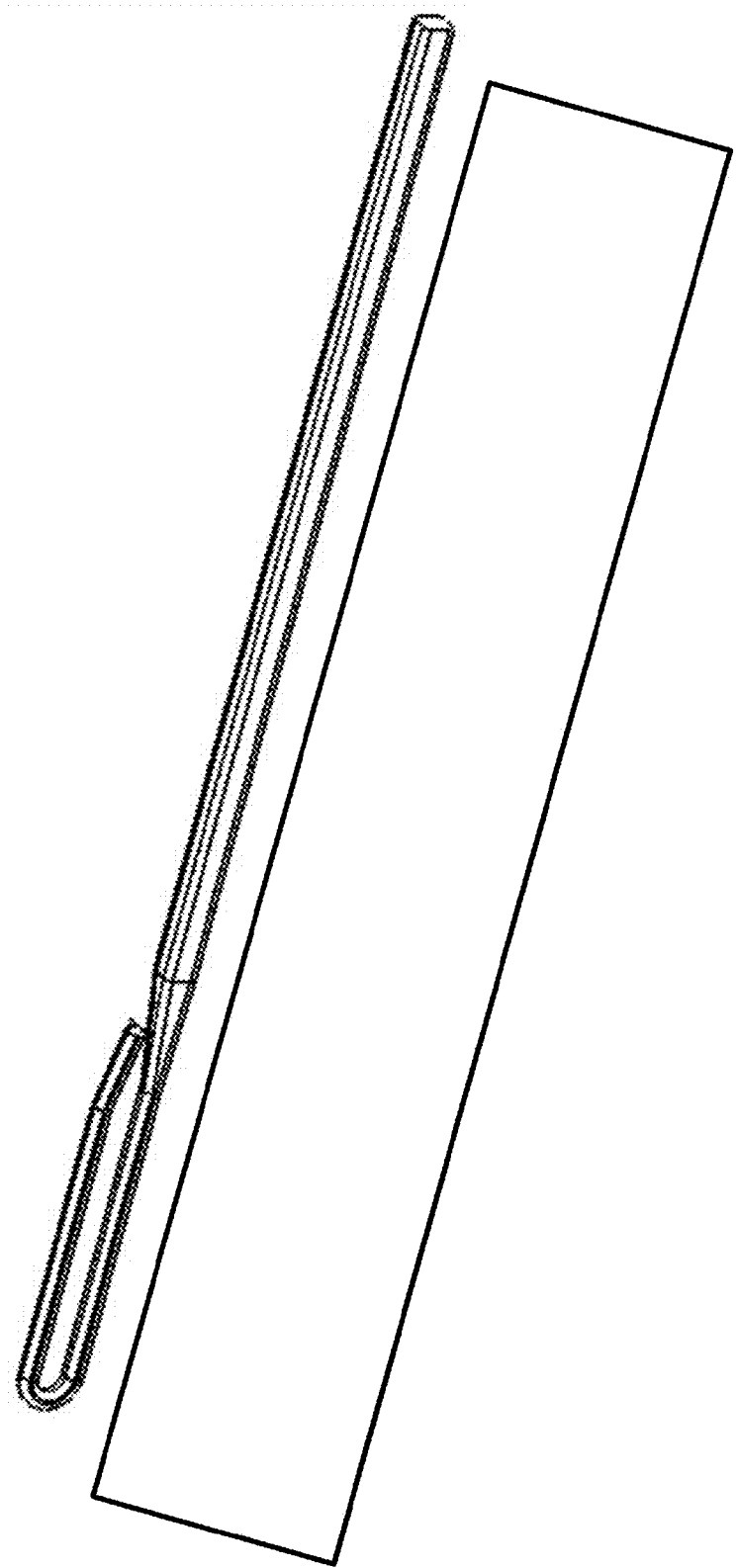

FIG. 10A shows a perspective view illustrating a hook in alternative embodiments for use with an automated machine for suturing of the present invention.

Figure 10B:
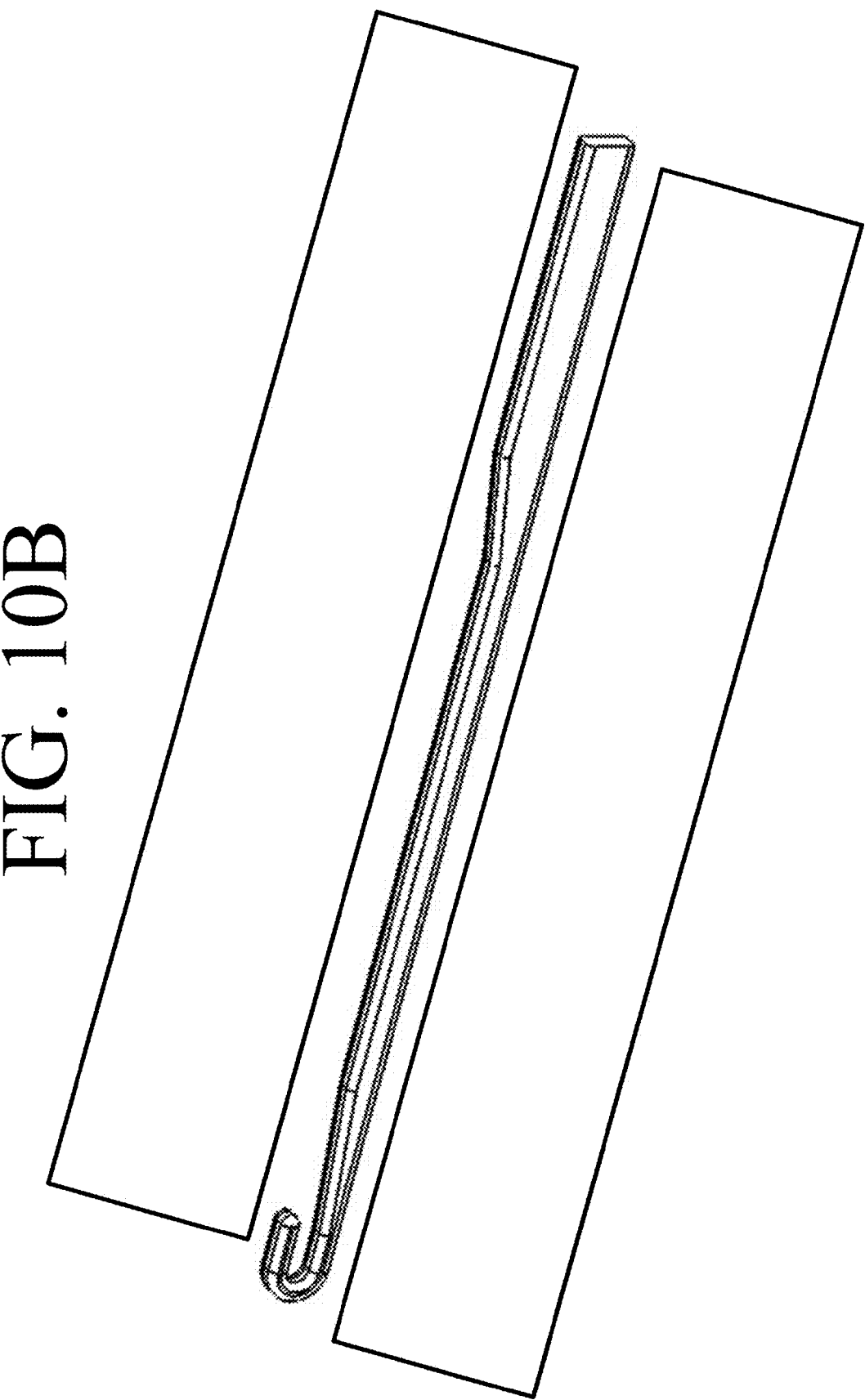

FIG. 10B shows a perspective view illustrating a hook in alternative embodiments for use with an automated machine for suturing of the present invention.

Figure 10C:
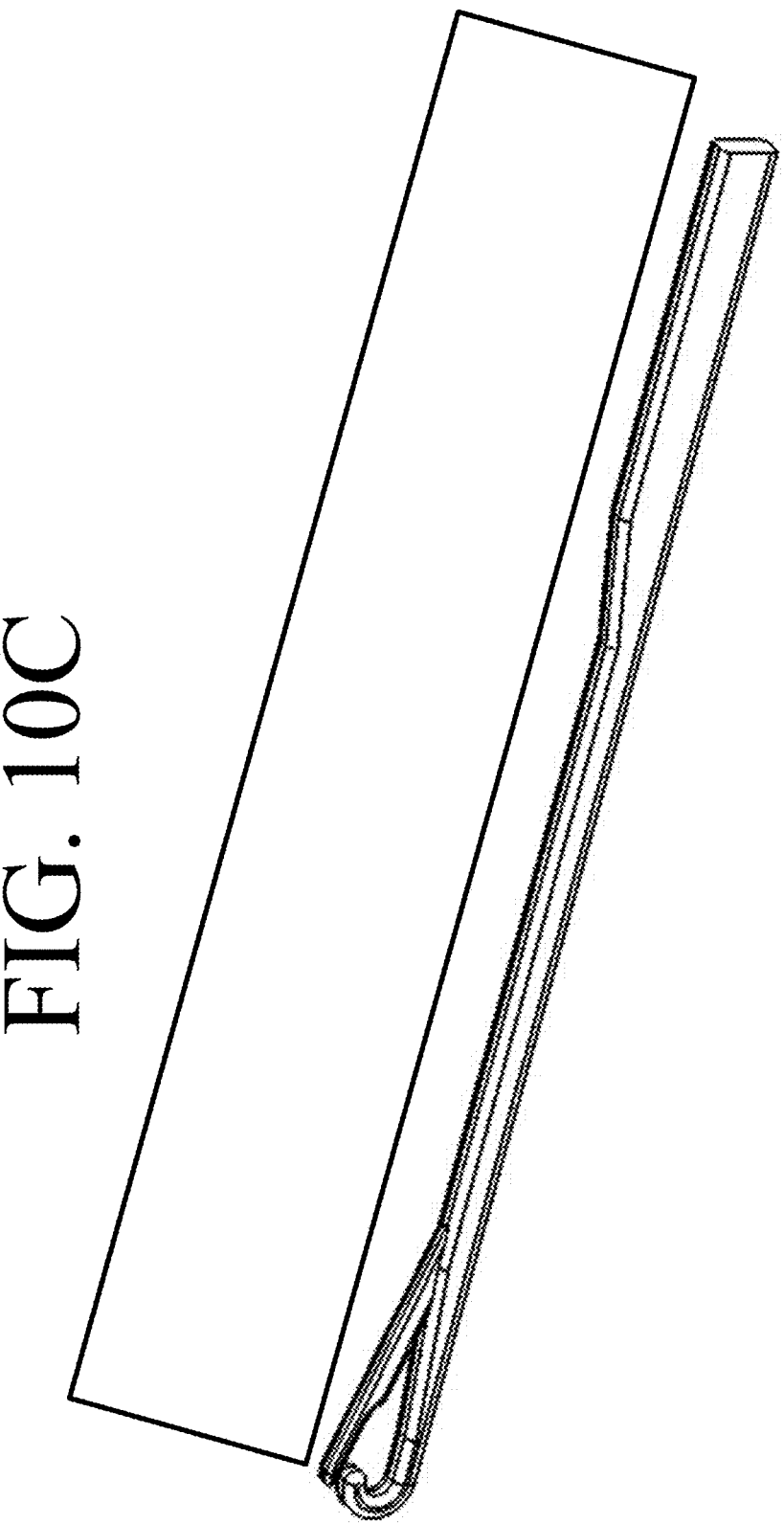

FIG. 10C shows a perspective view illustrating a hook in alternative embodiments for use with an automated machine for suturing of the present invention.

Figure 11:
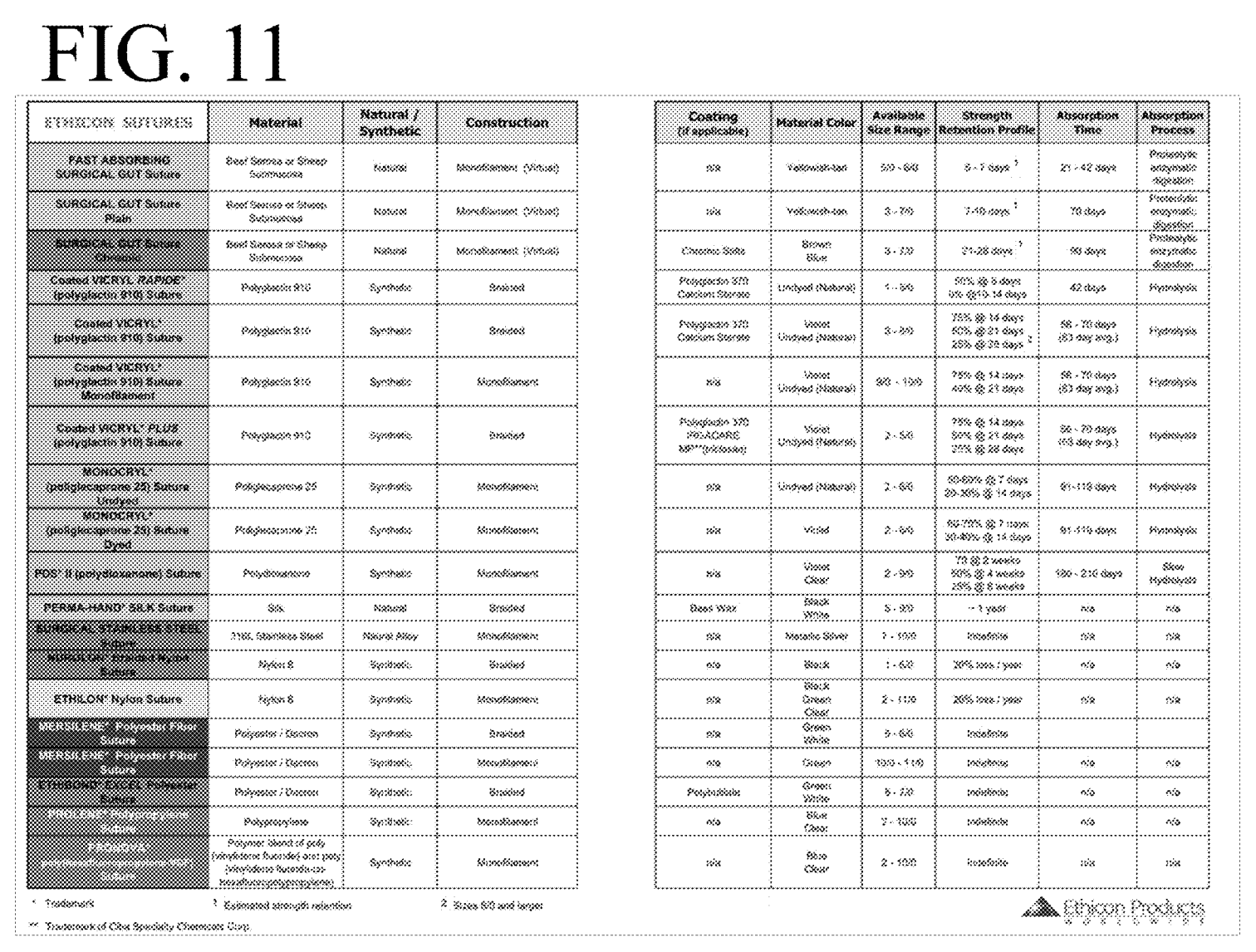

FIG. 11 is a table of commercial suture materials and prior art suture needle references.

Figure 12:
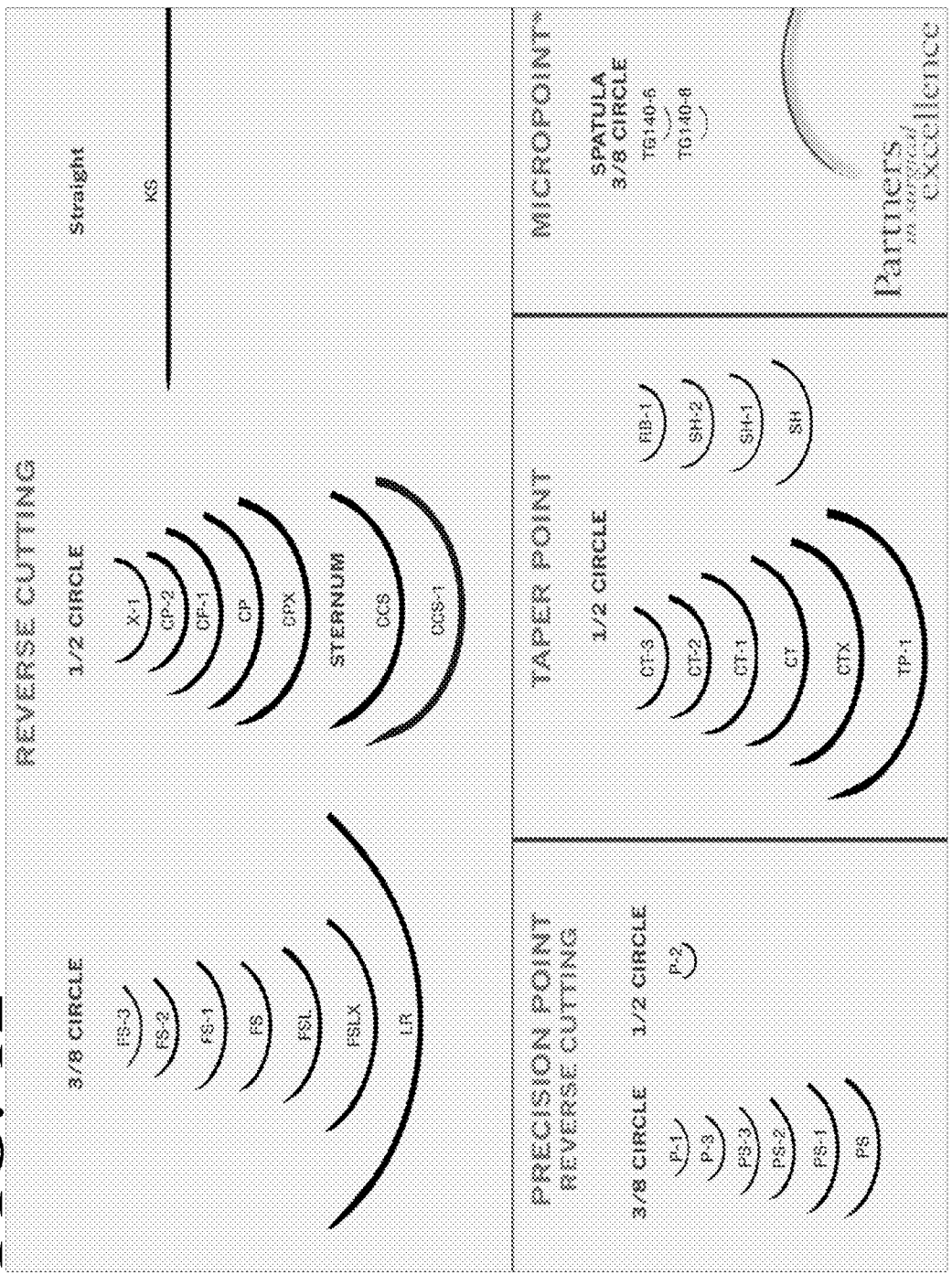

FIG. 12 is a table from Johnson & Johnson that shows commercial suture needle information references.

FIG. 13A is a perspective view diagram of the complete head portion of the automated machine in a position of operation for completing a stitch automated by the machine of the present invention.

FIG. 13B is a perspective view diagram of the complete head portion of the automated machine in a position of operation for completing a stitch automated by the machine of the present invention.

Figure 13:
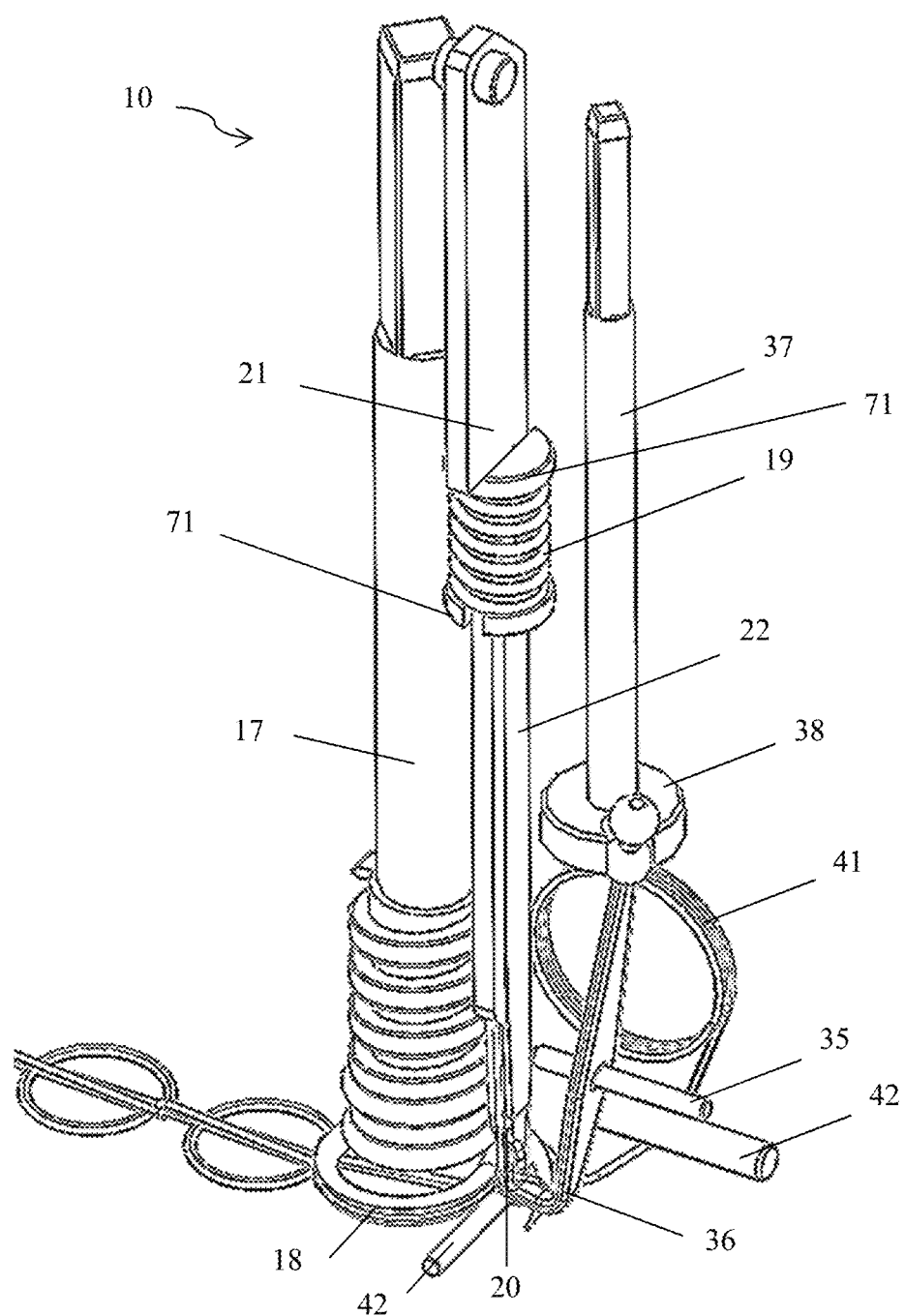
Figure 13:
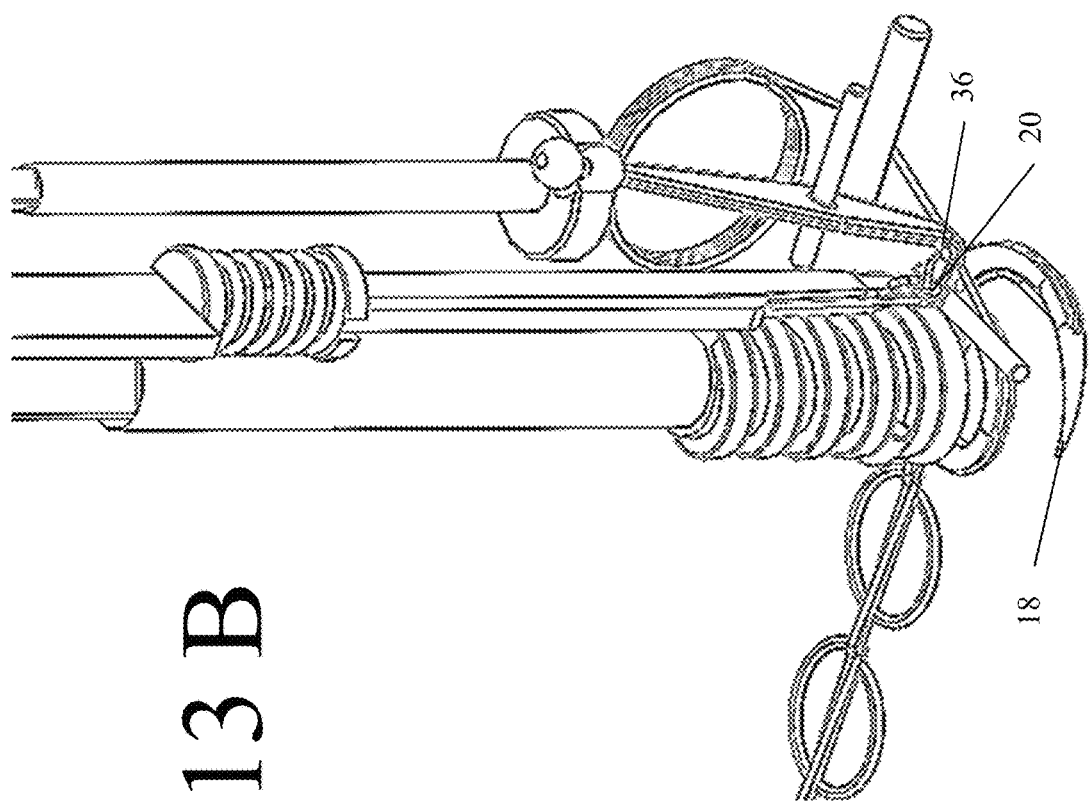
Figure 13C:
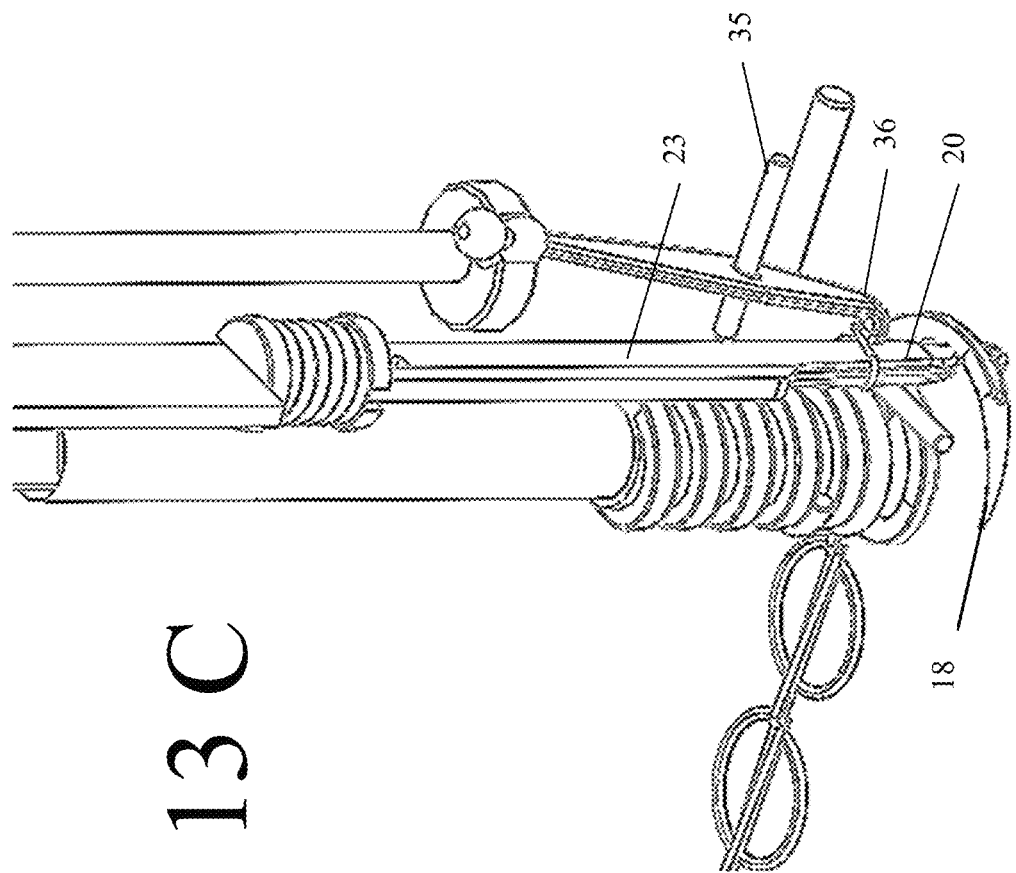
Figure 13:
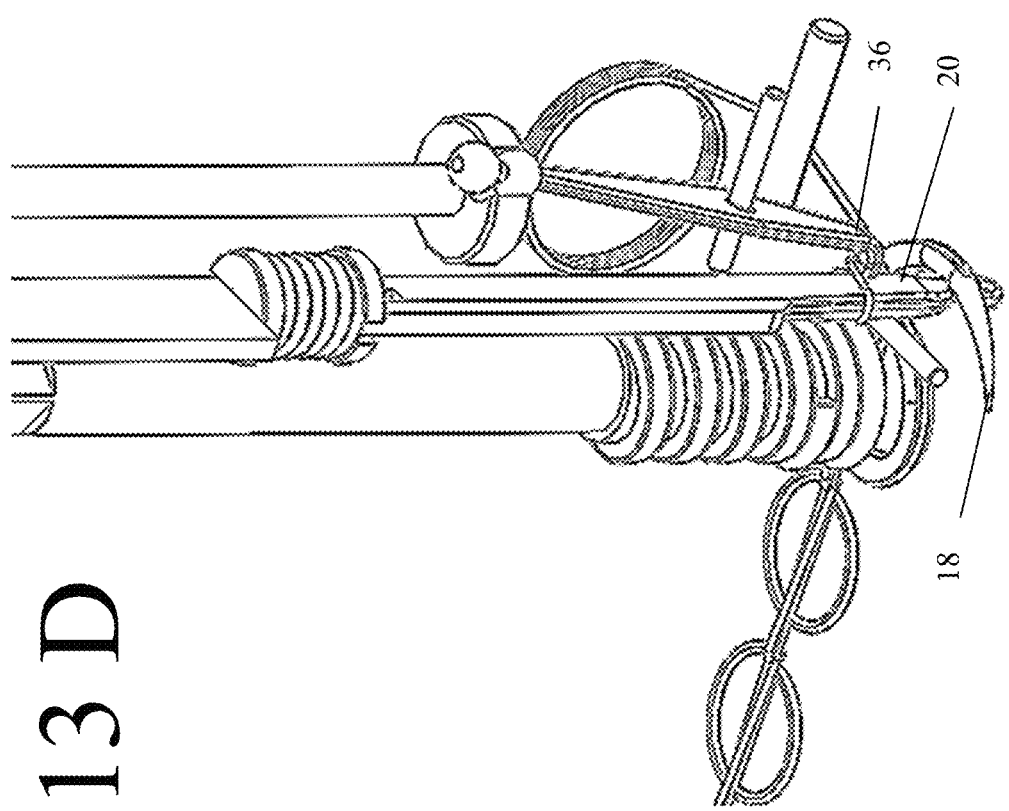
Figure 13:
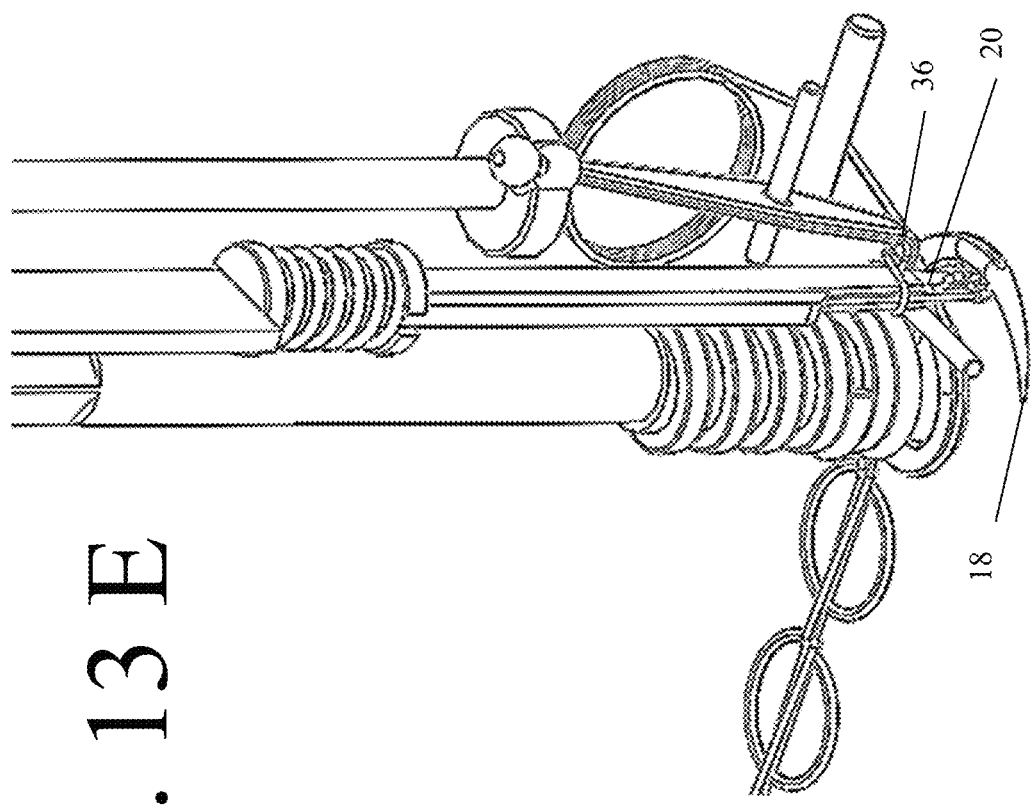
Figure 13:
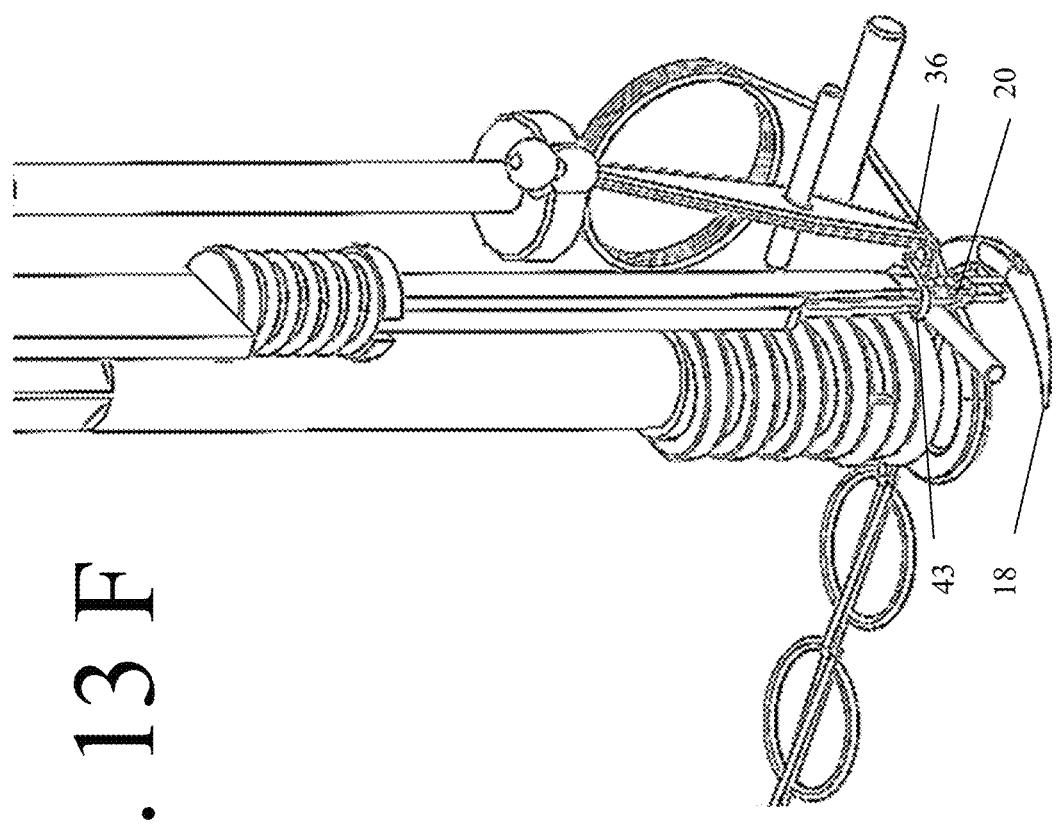
Figure 13:
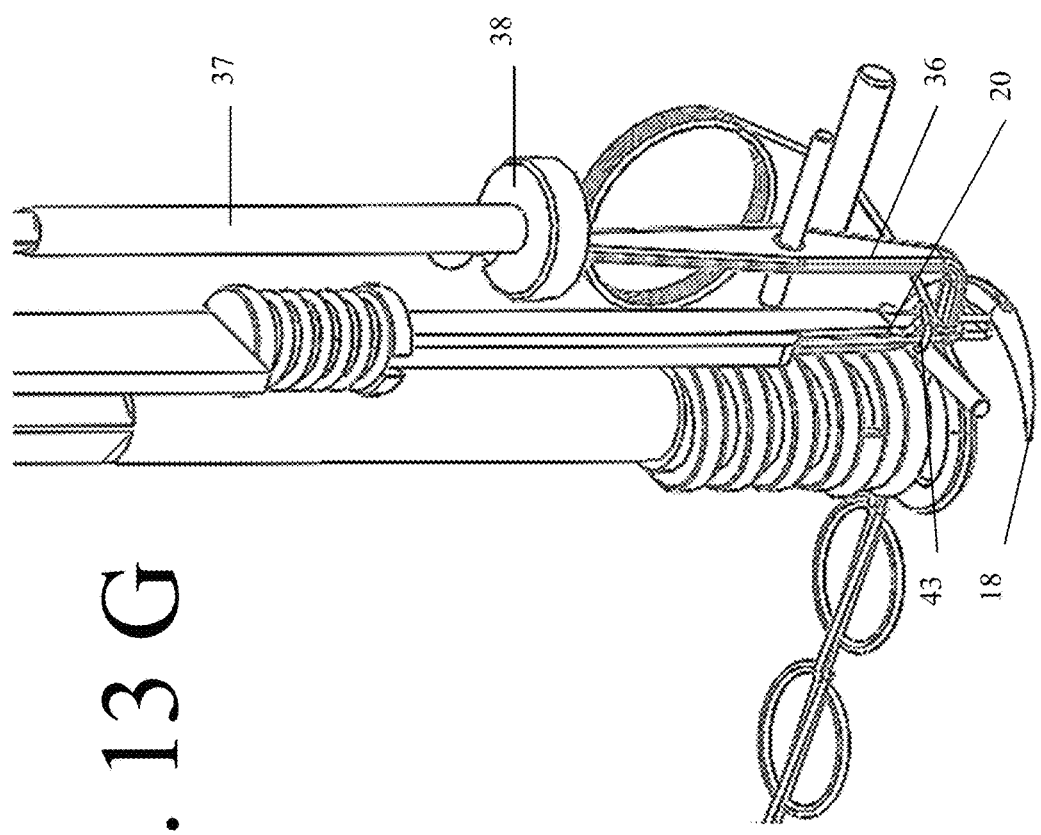
Figure 13:
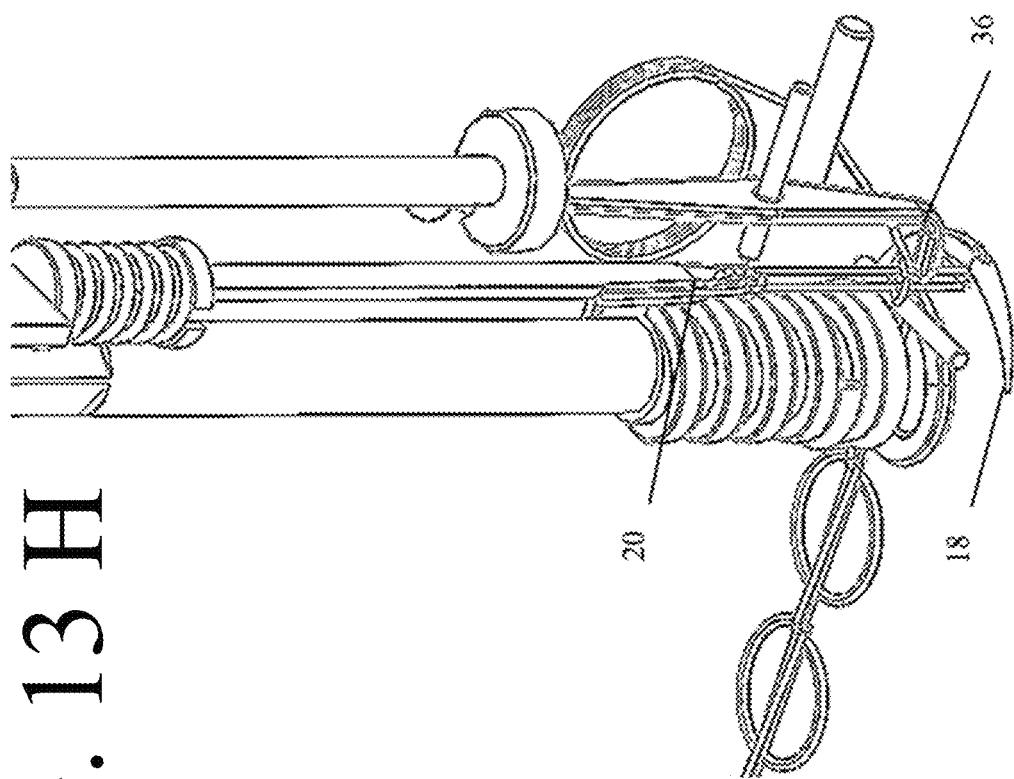
Figure 13:
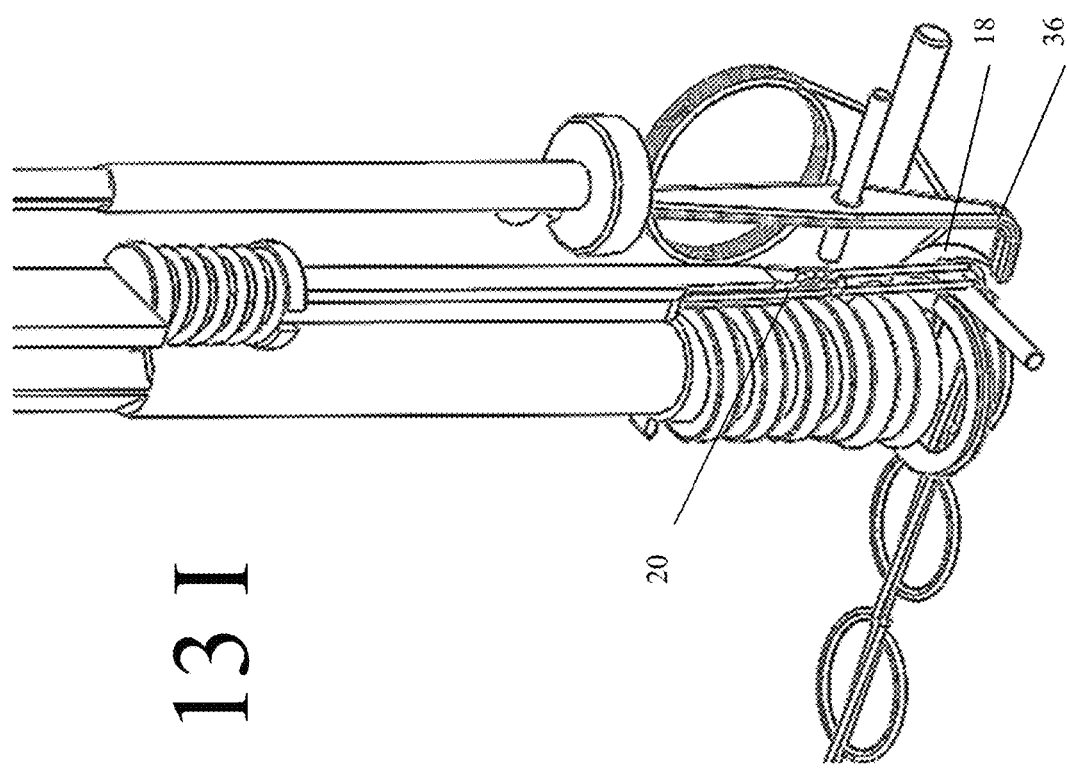
Figure 13:
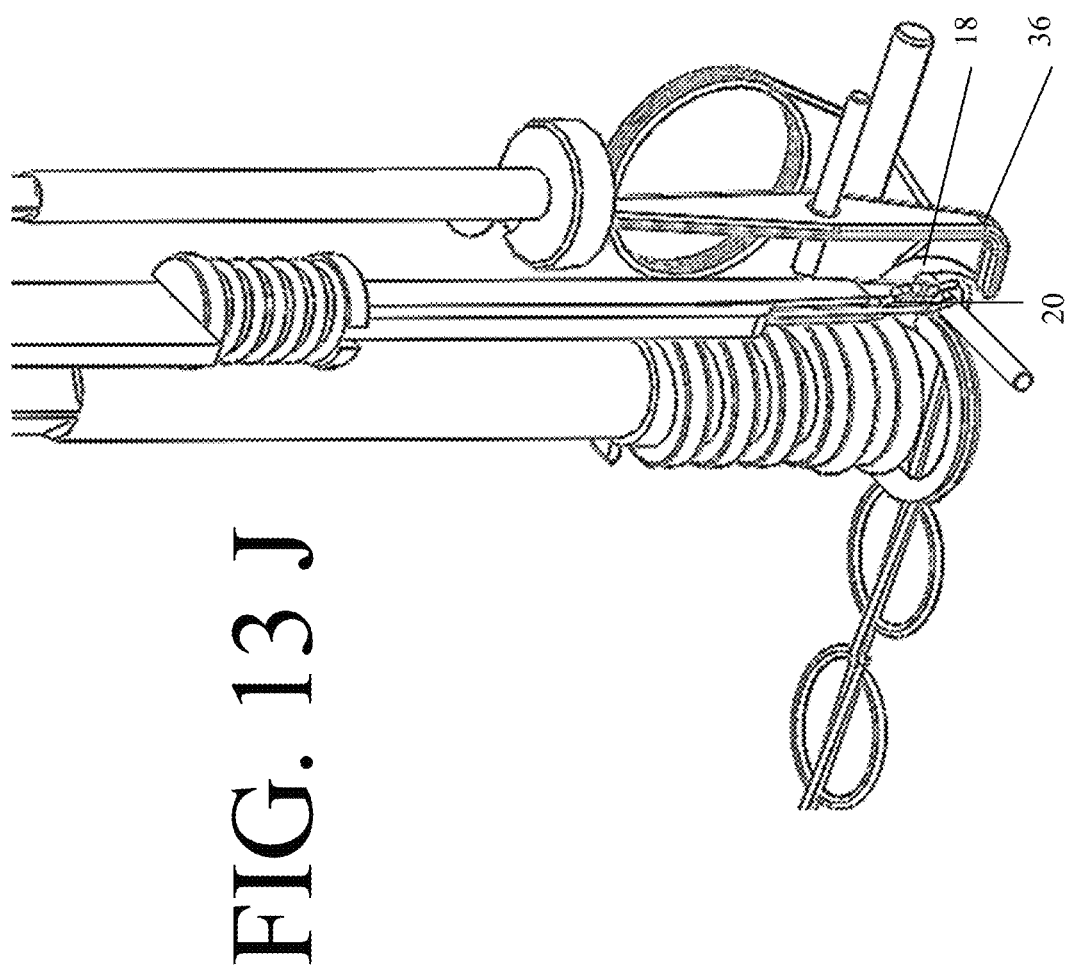
Figure 13:
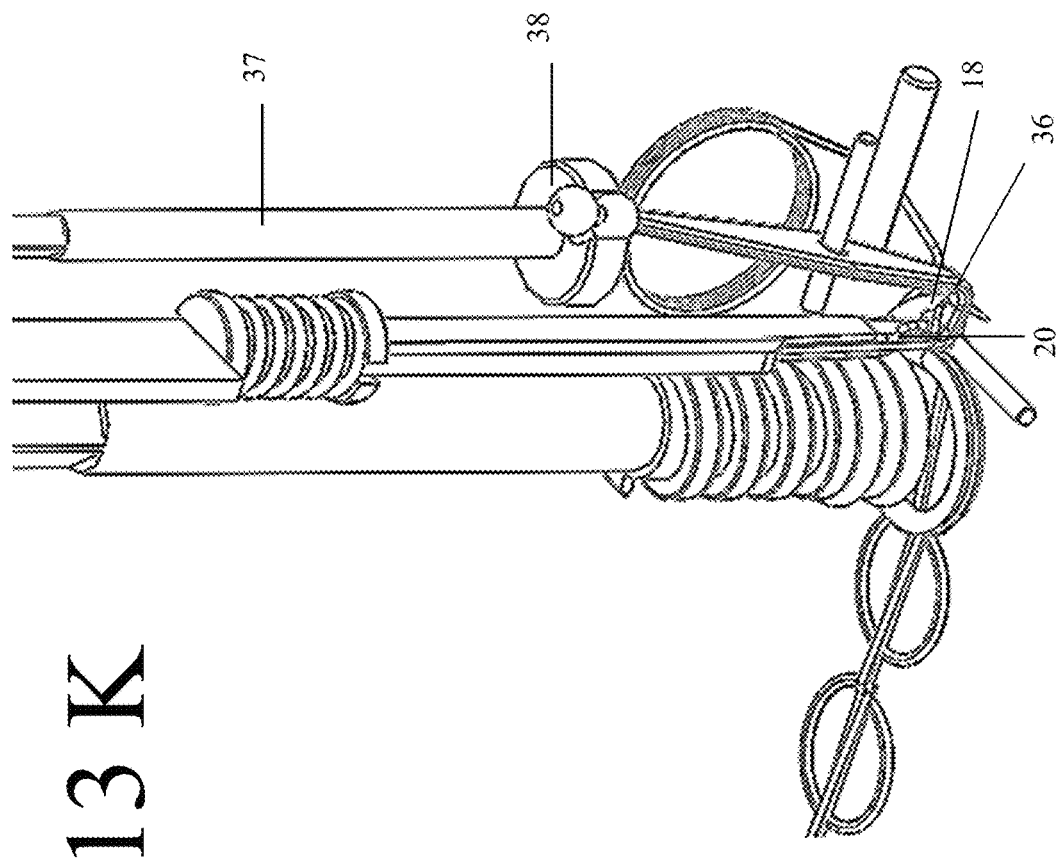

FIG. 13C is a perspective view diagram of the complete head portion of the automated machine in a position of operation for completing a stitch automated by the machine of the present invention.

FIG. 13D is a perspective view diagram of the complete head portion of the automated machine in a position of operation for completing a stitch automated by the machine of the present invention.

FIG. 13E is a perspective view diagram of the complete head portion of the automated machine in a position of operation for completing a stitch automated by the machine of the present invention.

FIG. 13F is a perspective view diagram of the complete head portion of the automated machine in a position of operation for completing a stitch automated by the machine of the present invention.

FIG. 13G is a perspective view diagram of the complete head portion of the automated machine in a position of operation for completing a stitch automated by the machine of the present invention.

FIG. 13H is a perspective view diagram of the complete head portion of the automated machine in a position of operation for completing a stitch automated by the machine of the present invention.

FIG. 13I is a perspective view diagram of the complete head portion of the automated machine in a position of operation for completing a stitch automated by the machine of the present invention.

FIG. 13J is a perspective view diagram of the complete head portion of the automated machine in a position of operation for completing a stitch automated by the machine of the present invention.

FIG. 13K is a perspective view diagram of the complete head portion of the automated machine in a position of operation for completing a stitch automated by the machine of the present invention.

FIG. 14A shows a perspective view diagram of the inferior angle of the head portion of the automated machine in a position of operation for completing a stitch in suturing automated by the machine of the present invention.

Figure 14B:
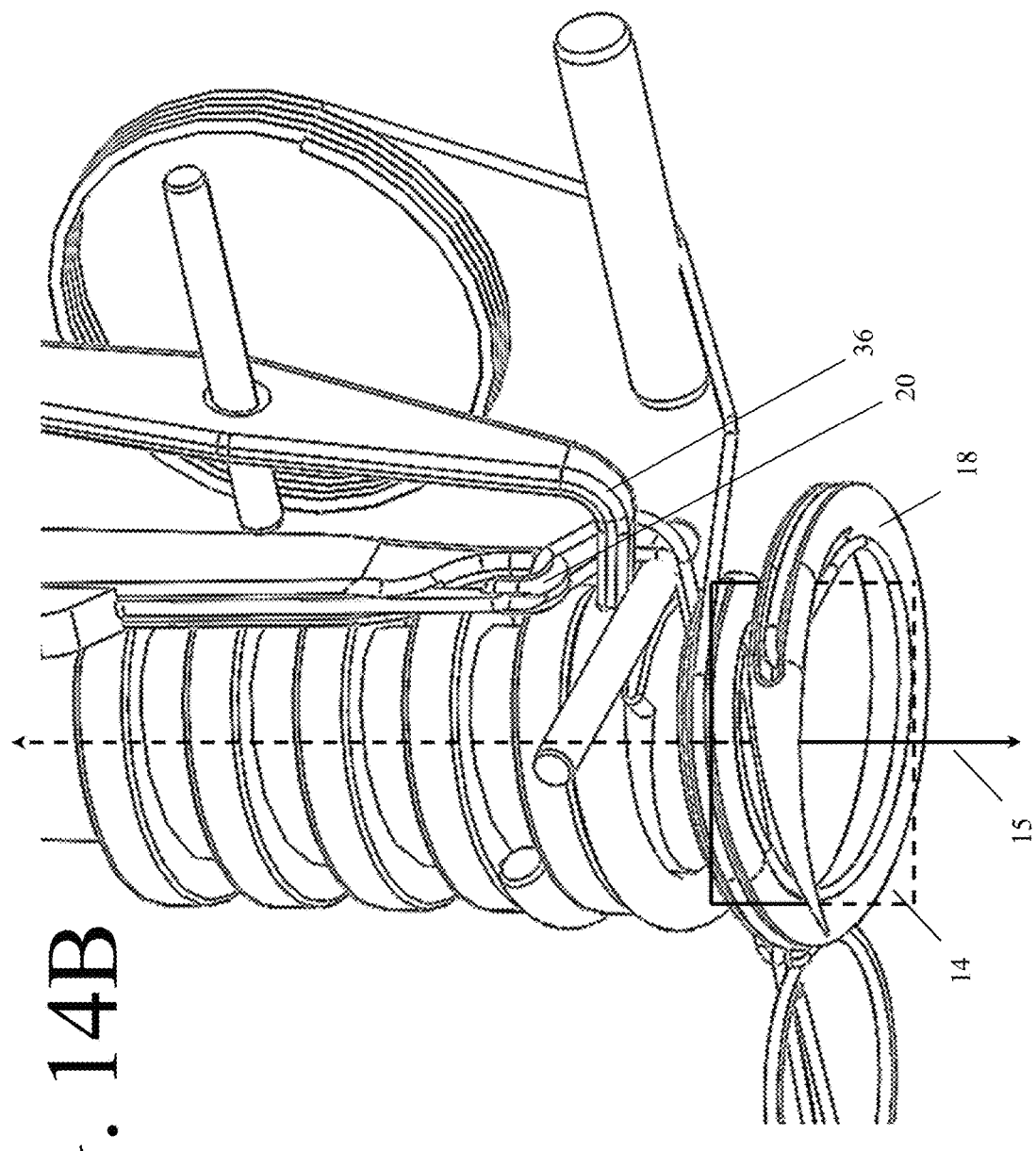

FIG. 14B shows a perspective view diagram of the inferior angle of the head portion of the automated machine in a position of operation for completing a stitch in suturing automated by the machine of the present invention.

Figure 14C:
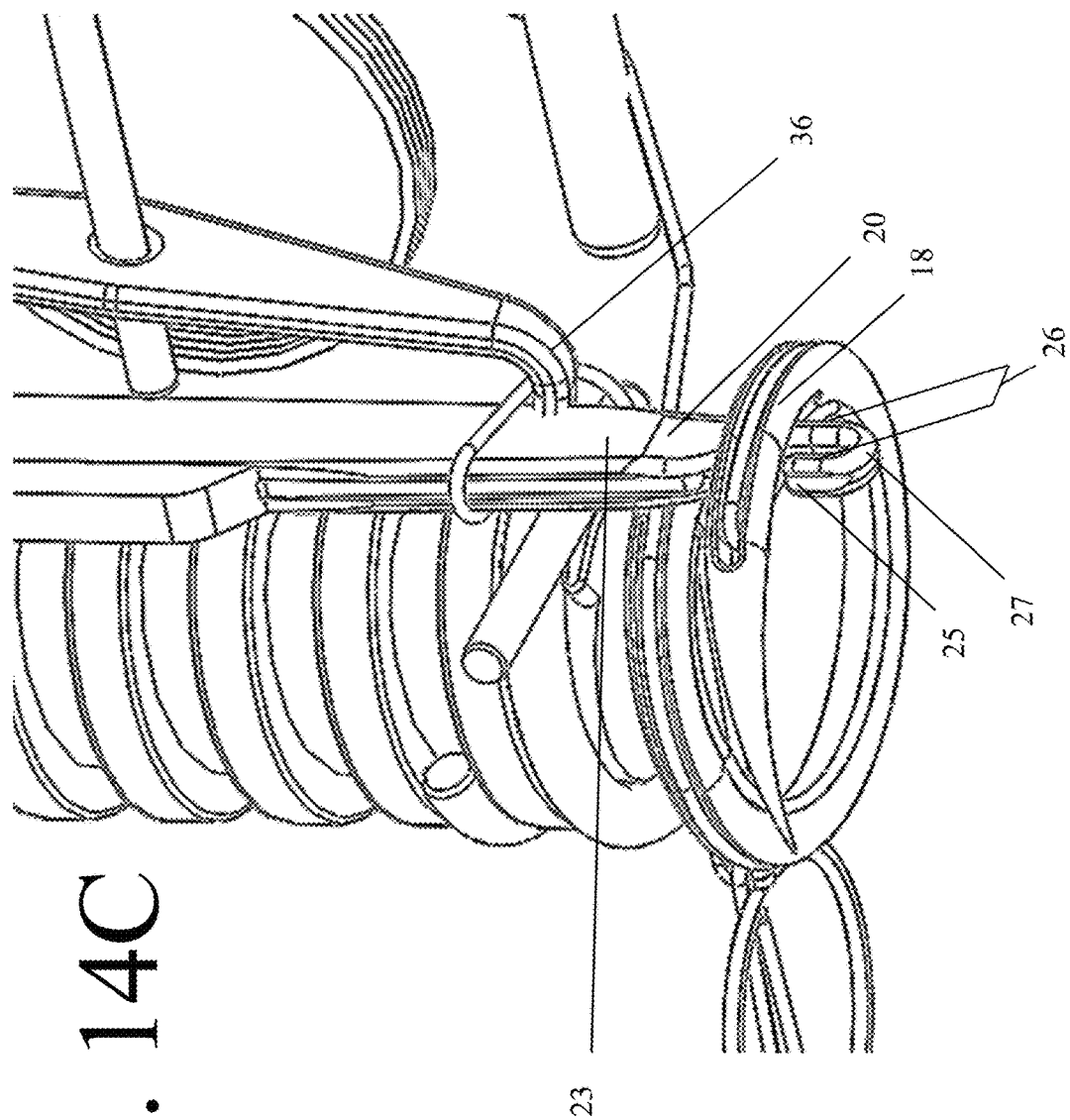

FIG. 14C shows a perspective view diagram of the inferior angle of the head portion of the automated machine in a position of operation for completing a stitch in suturing automated by the machine of the present invention.

Figure 14D:
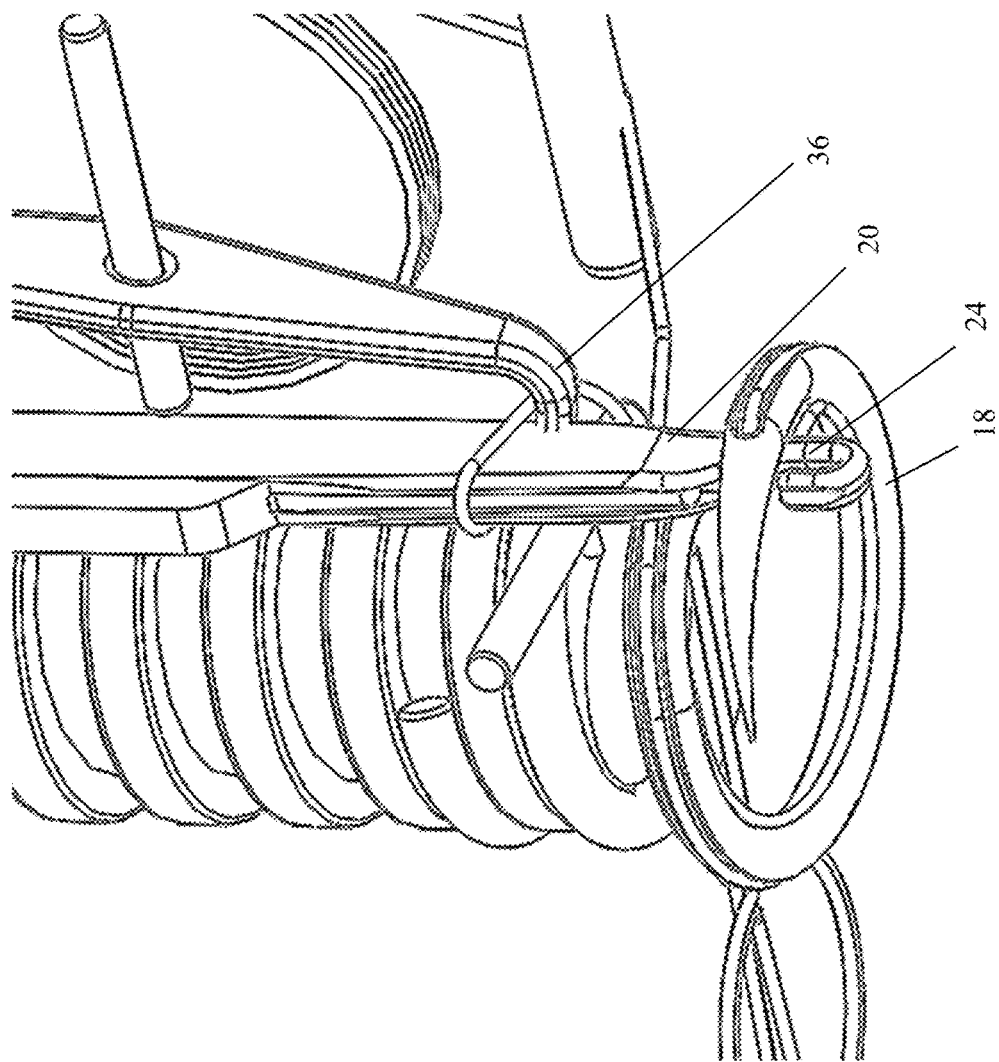

FIG. 14D shows a perspective view diagram of the inferior angle of the head portion of the automated machine in a position of operation for completing a stitch in suturing automated by the machine of the present invention.

FIG. 14E shows a perspective view diagram of the inferior angle of the head portion of the automated machine in a position of operation for completing a stitch in suturing automated by the machine of the present invention.

Figure 14F:
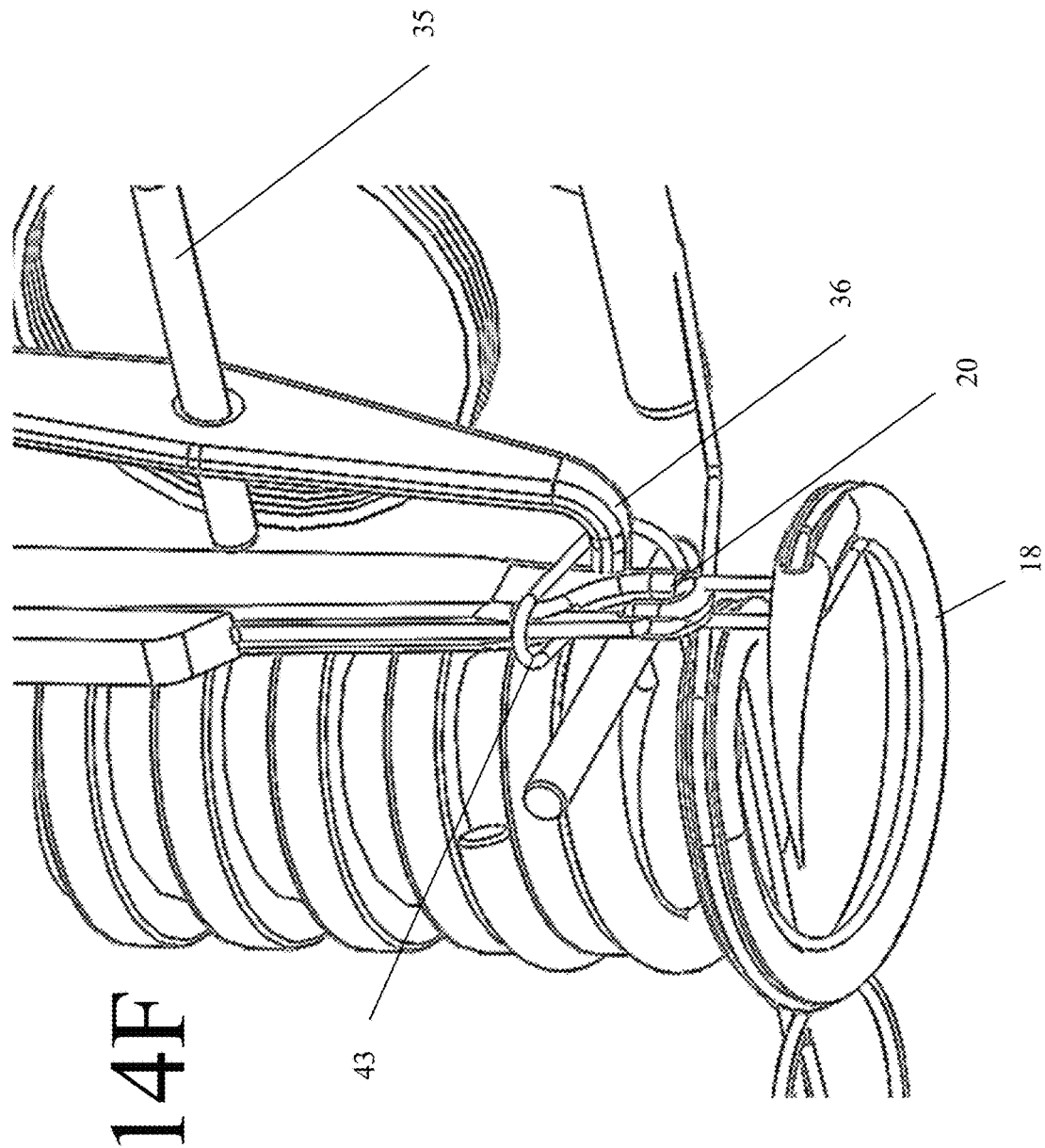

FIG. 14F shows a perspective view diagram of the inferior angle of the head portion of the automated machine in a position of operation for completing a stitch in suturing automated by the machine of the present invention.

FIG. 14G shows a perspective view diagram of the inferior angle of the head portion of the automated machine in a position of operation for completing a stitch in suturing automated by the machine of the present invention.

Figure 14H:
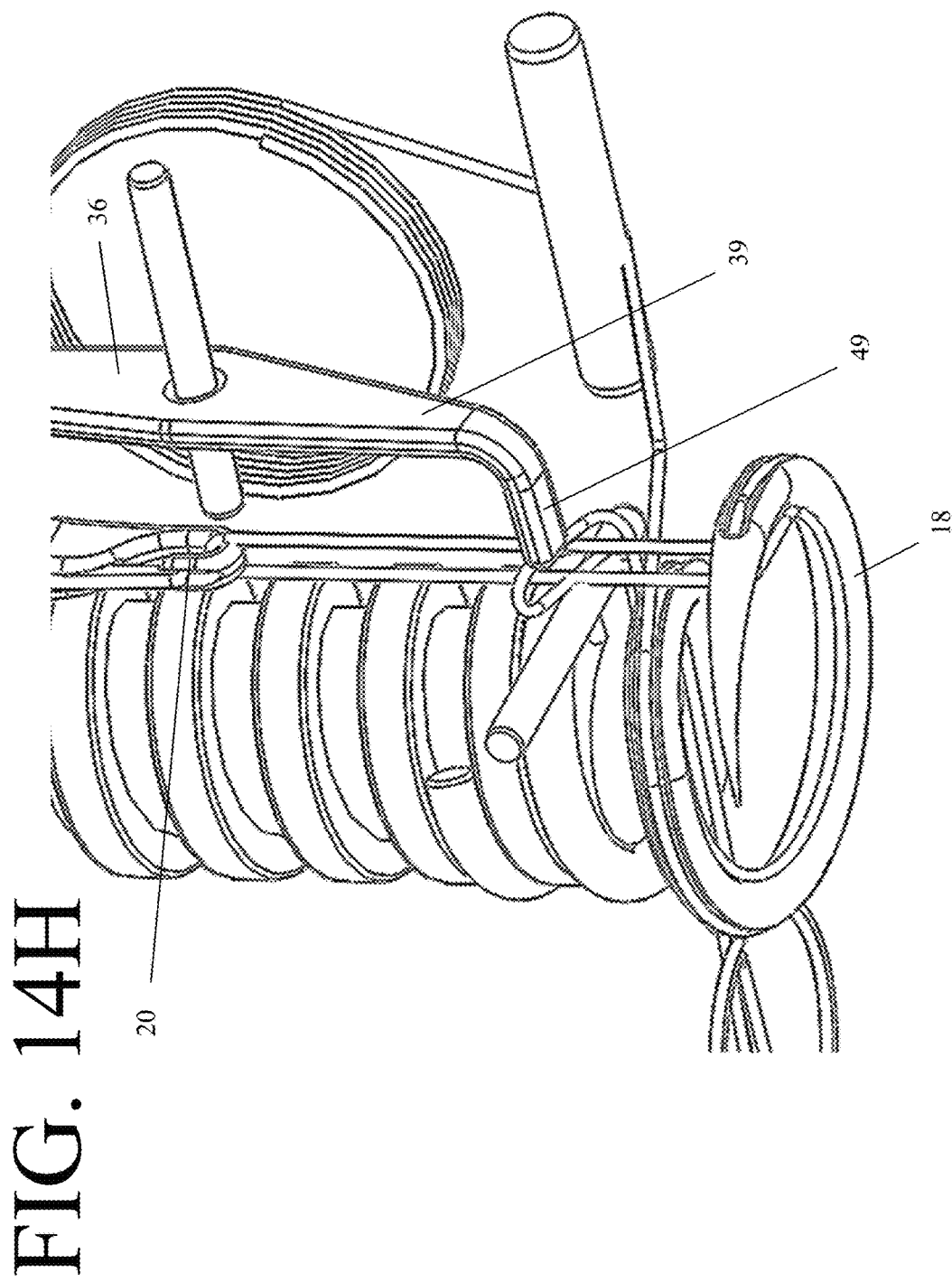

FIG. 14H shows a perspective view diagram of the inferior angle of the head portion of the automated machine in a position of operation for completing a stitch in suturing automated by the machine of the present invention.

Figure 14I:
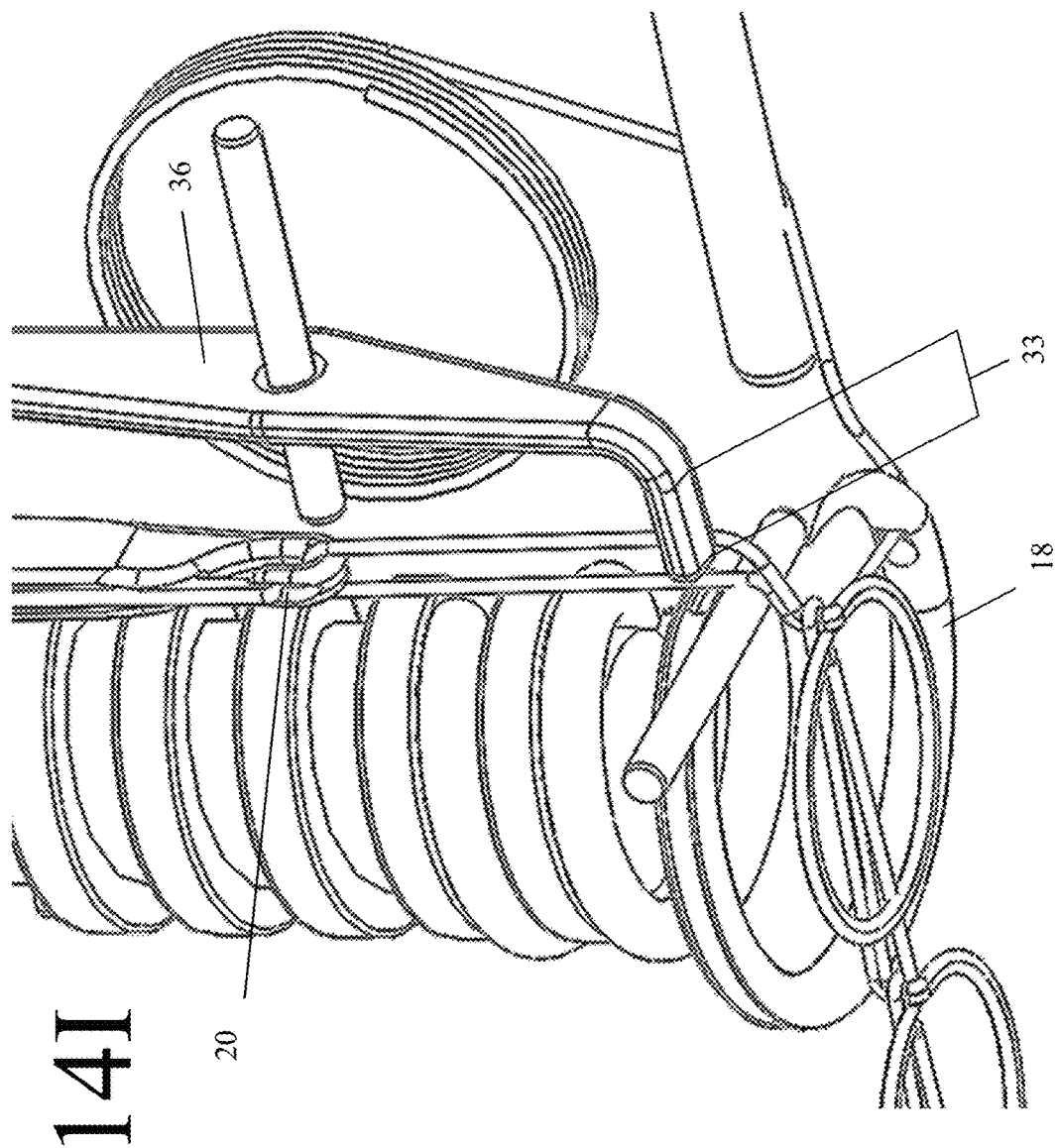

FIG. 14I shows a perspective view diagram of the inferior angle of the head portion of the automated machine in a position of operation for completing a stitch in suturing automated by the machine of the present invention.

Figure 14J:
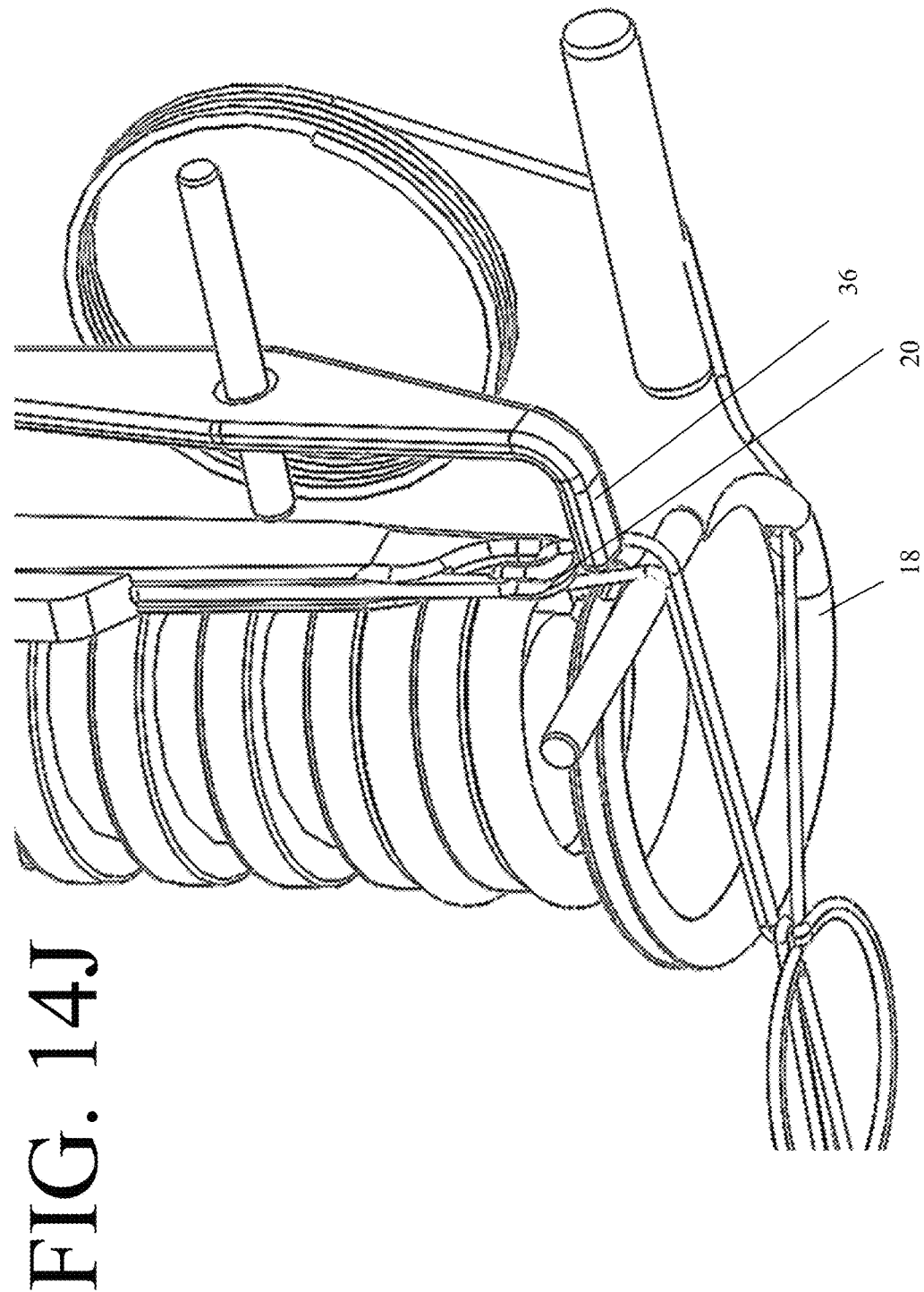

FIG. 14J shows a perspective view diagram of the inferior angle of the head portion of the automated machine in a position of operation for completing a stitch in suturing automated by the machine of the present invention.

Figure 14K:
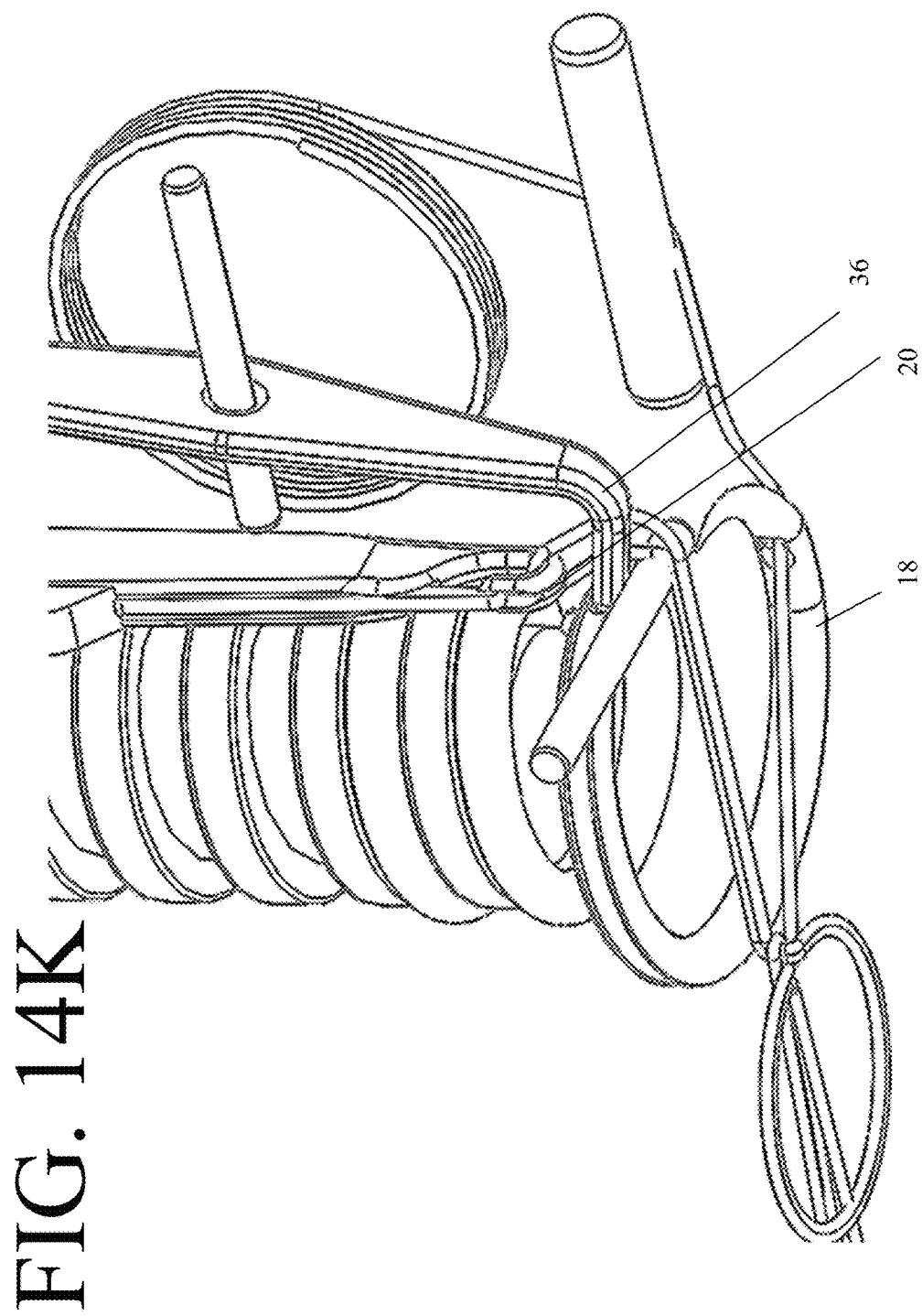

FIG. 14K shows a perspective view diagram of the inferior angle of the head portion of the automated machine in a position of operation for completing a stitch in suturing automated by the machine of the present invention.

FIG. 15A shows a perspective view diagram of the complete head portion in a position of operation for completing a stitch in suturing by the machine of the present invention.

Figure 15B:
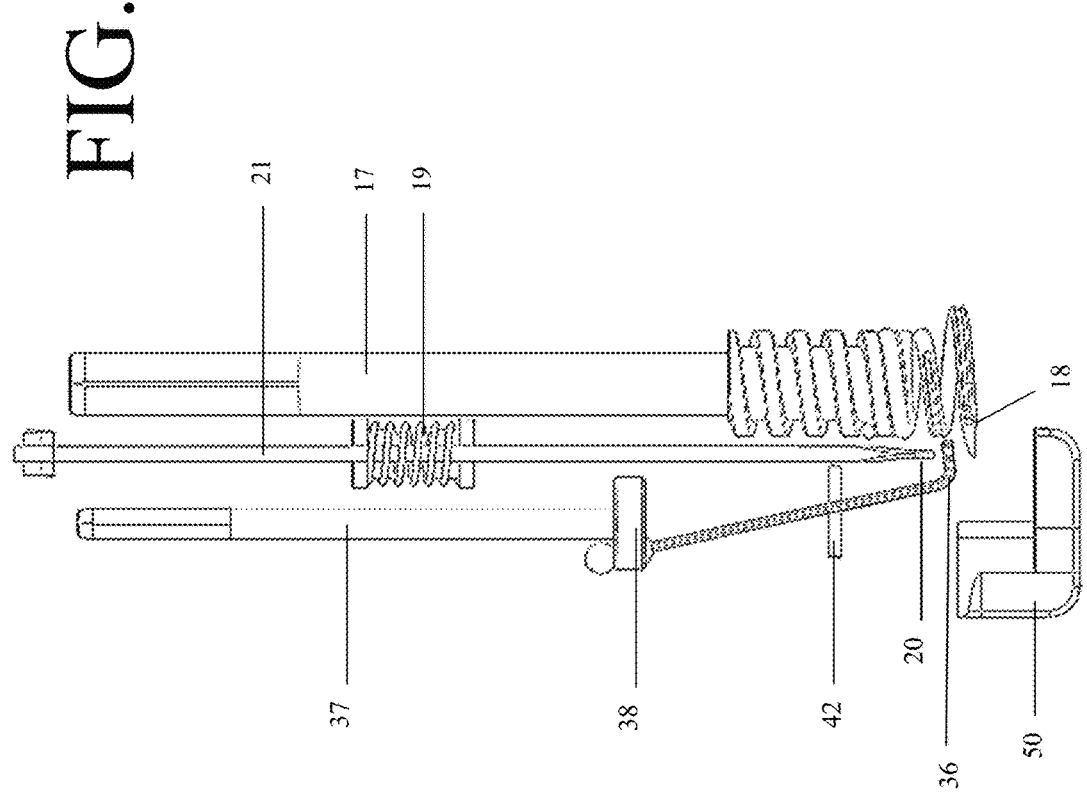

FIG. 15B shows a perspective view diagram of the complete head portion in a position of operation for completing a stitch in suturing by the machine of the present invention.

FIG. 15C shows a perspective view diagram of the complete head portion in a position of operation for completing a stitch in suturing by the machine of the present invention.

Figure 15D:
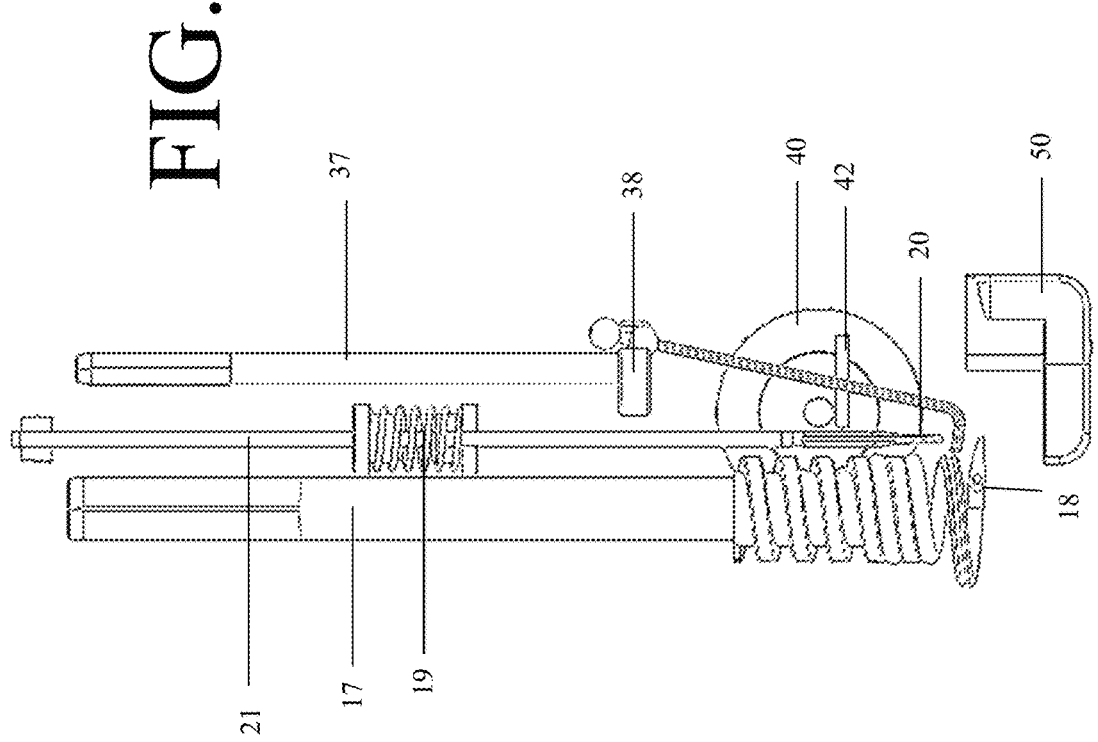

FIG. 15D shows a perspective view diagram of the complete head portion in a position of operation for completing a stitch in suturing by the machine of the present invention.

Figure 15E:
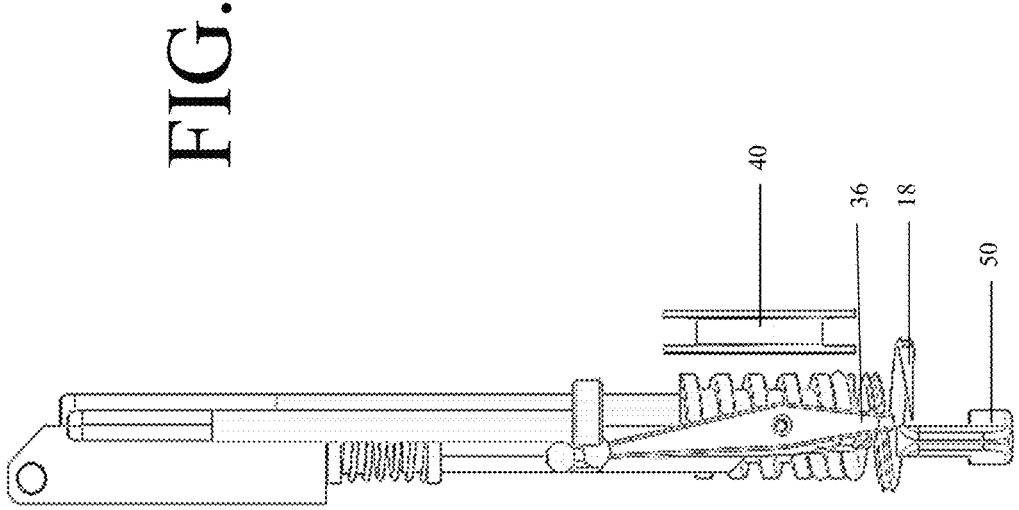

FIG. 15E shows a perspective view diagram of the complete head portion in a position of operation for completing a stitch in suturing by the machine of the present invention.

FIG. 15F shows a perspective view diagram of the complete head portion in a position of operation for completing a stitch in suturing by the machine of the present invention.

Figure 15G:
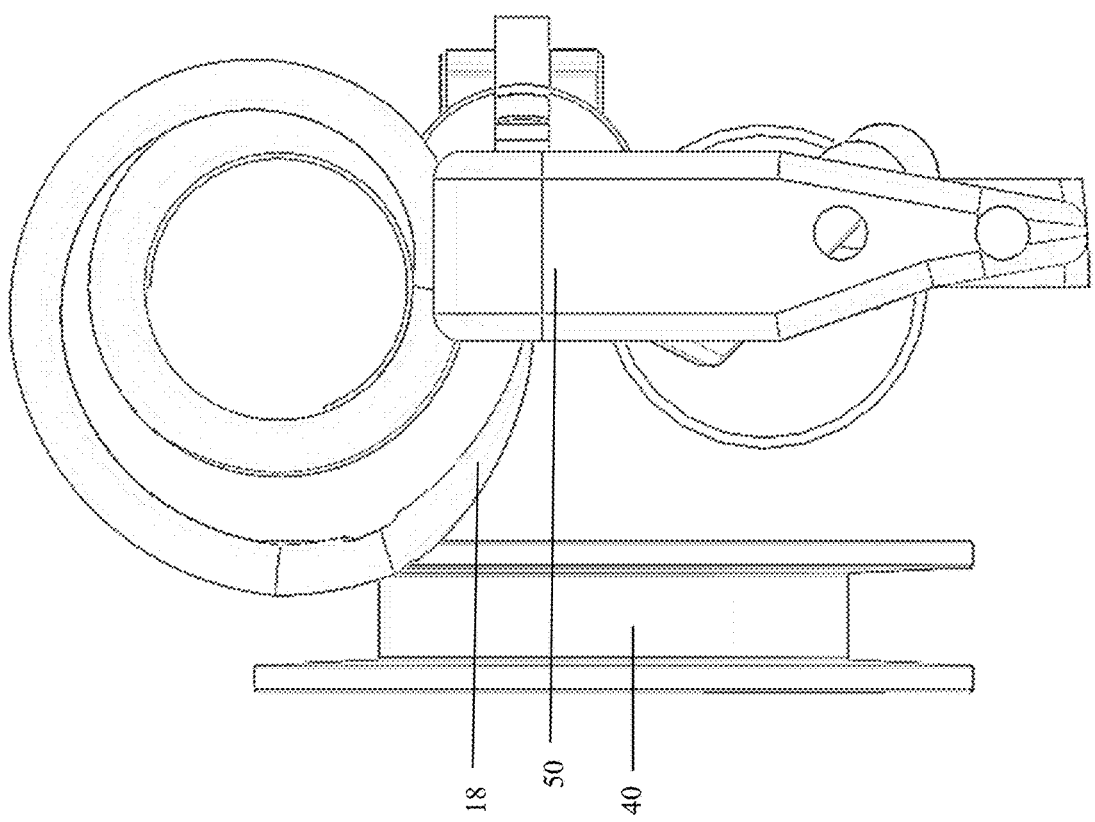

FIG. 15G shows a perspective view diagram of the complete head portion in a position of operation for completing a stitch in suturing by the machine of the present invention.

Figure 15H:
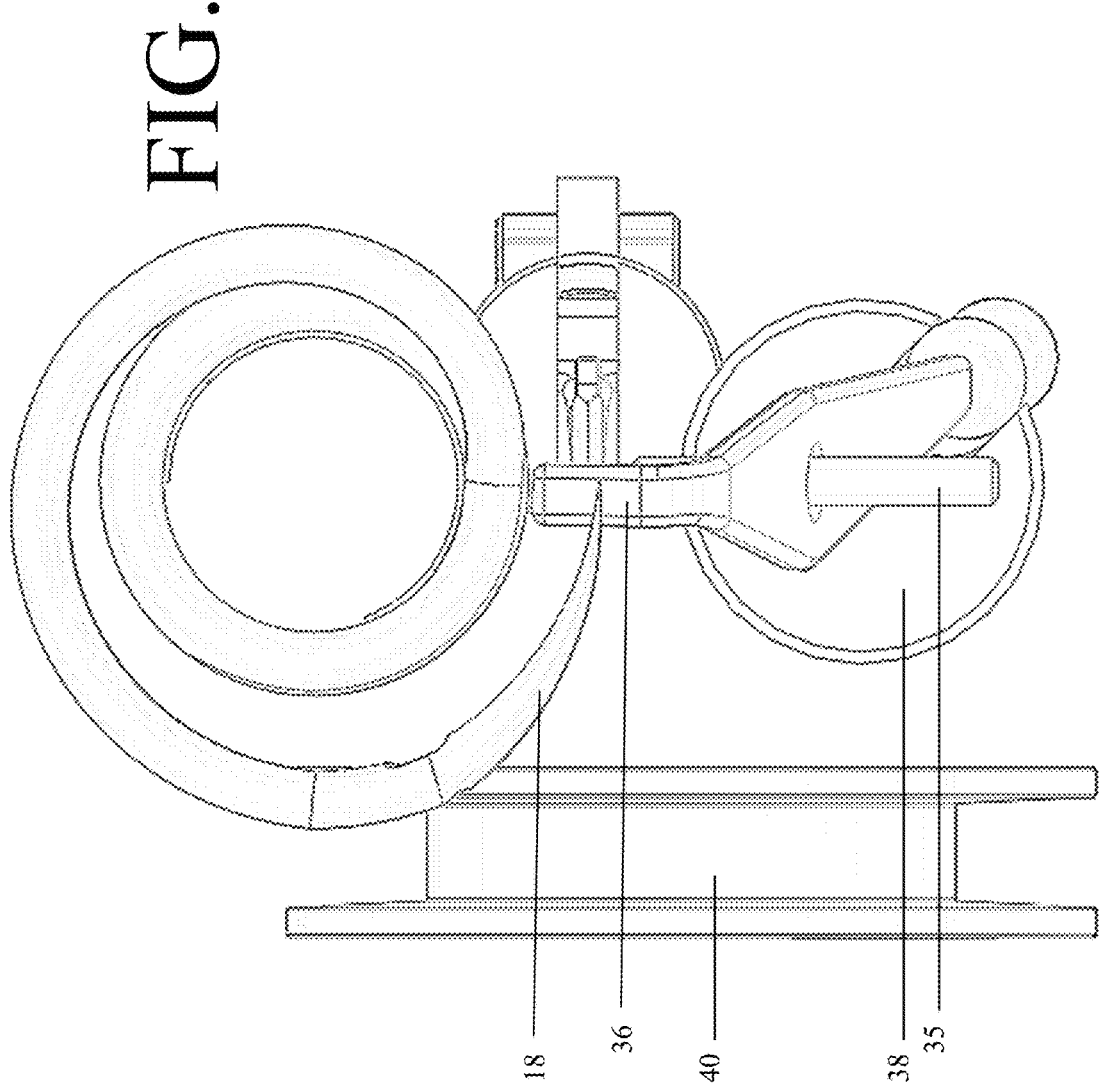

FIG. 15H shows a perspective view diagram of the complete head portion in a position of operation for completing a stitch in suturing by the machine of the present invention.

Figure 15I:
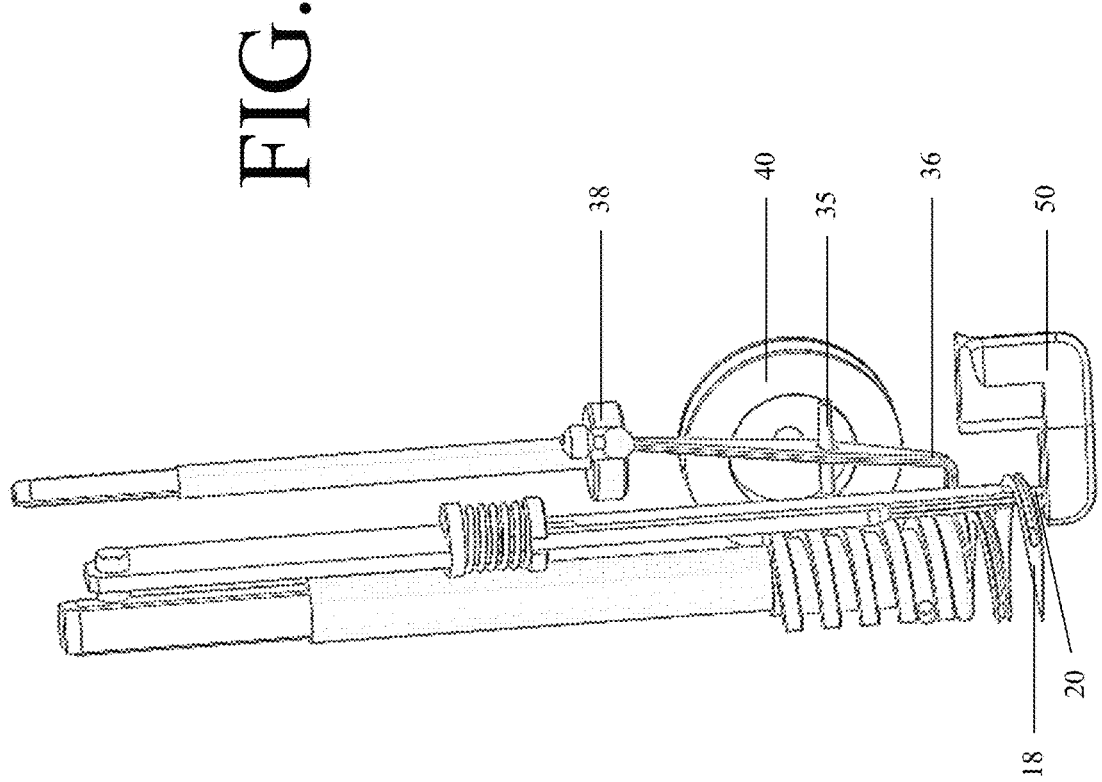

FIG. 15I shows a perspective view diagram of the complete head portion in a position of operation for completing a stitch in suturing by the machine of the present invention.

FIG. 15J shows a perspective view diagram of the complete head portion in a position of operation for completing a stitch in suturing by the machine of the present invention.

Figure 15K:
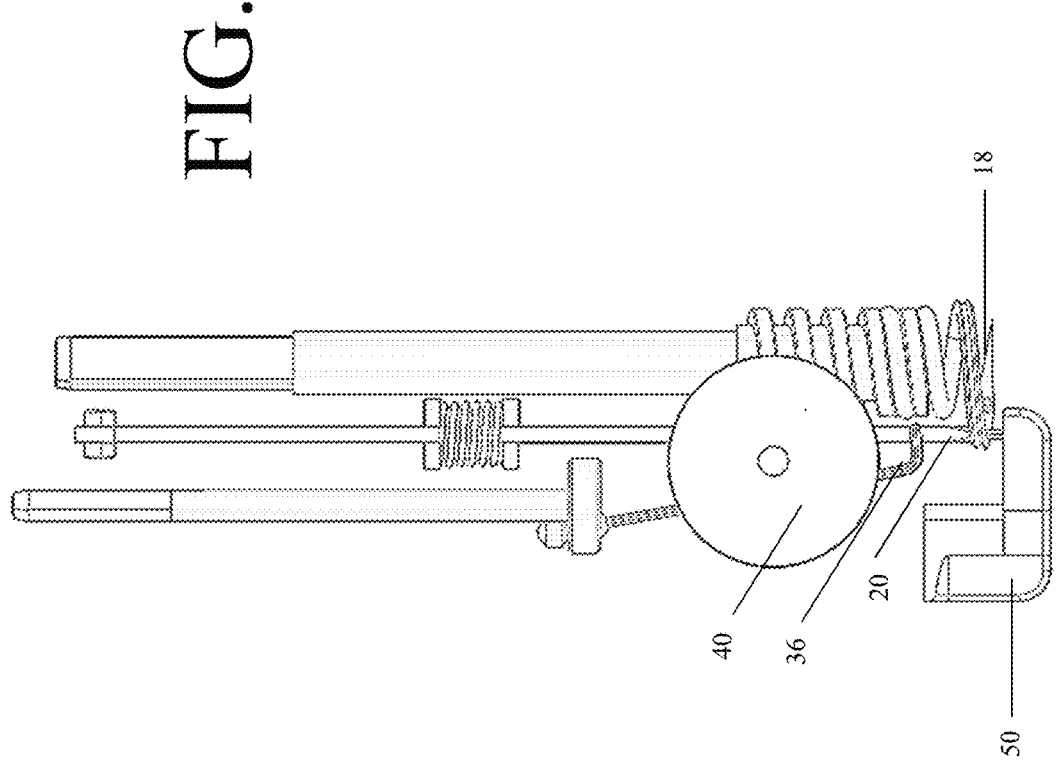

FIG. 15K shows a perspective view diagram of the complete head portion in a position of operation for completing a stitch in suturing by the machine of the present invention.

Figure 15L:
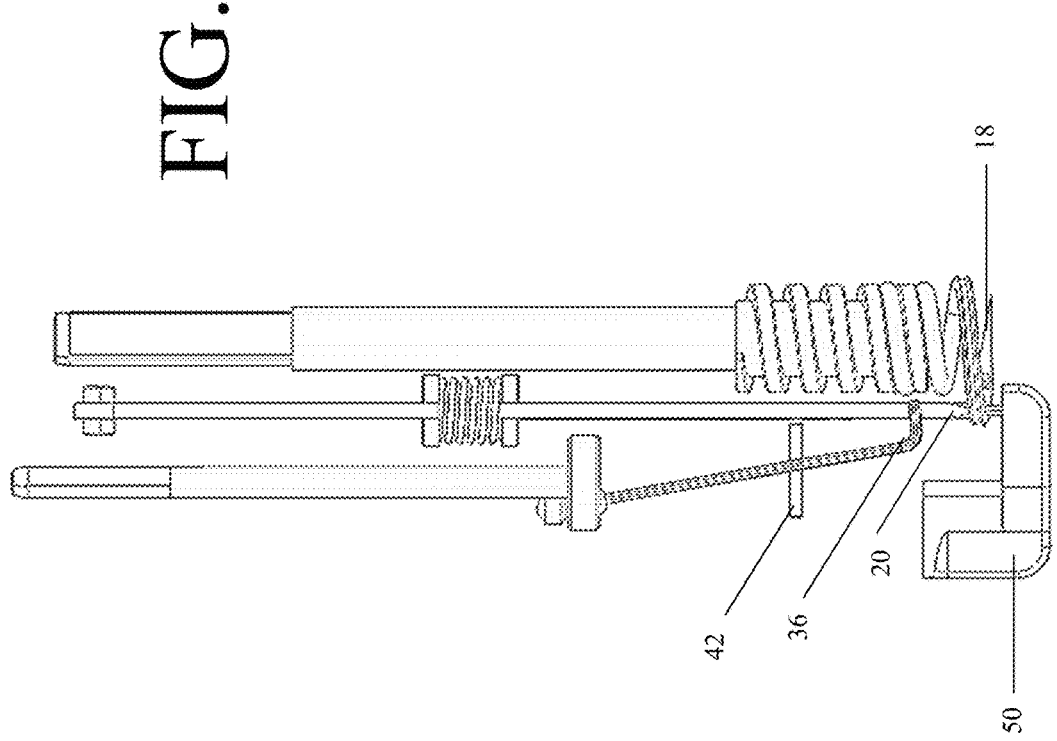
Figure 150:
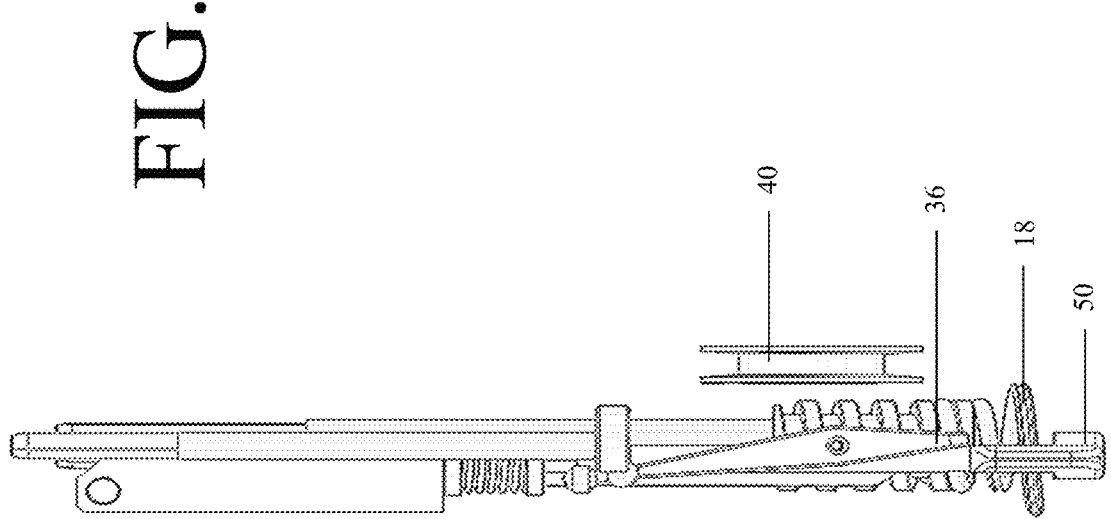

FIG. 15L shows a perspective view diagram of the complete head portion in a position of operation for completing a stitch in suturing by the machine of the present invention.

FIG. 15M shows a perspective view diagram of the complete head portion in a position of operation for completing a stitch in suturing by the machine of the present invention.

FIG. 15N shows a perspective view diagram of the complete head portion in a position of operation for completing a stitch in suturing by the machine of the present invention.

FIG. 15O shows a perspective view diagram of the complete head portion in a position of operation for completing a stitch in suturing by the machine of the present invention.

Figure 15P:
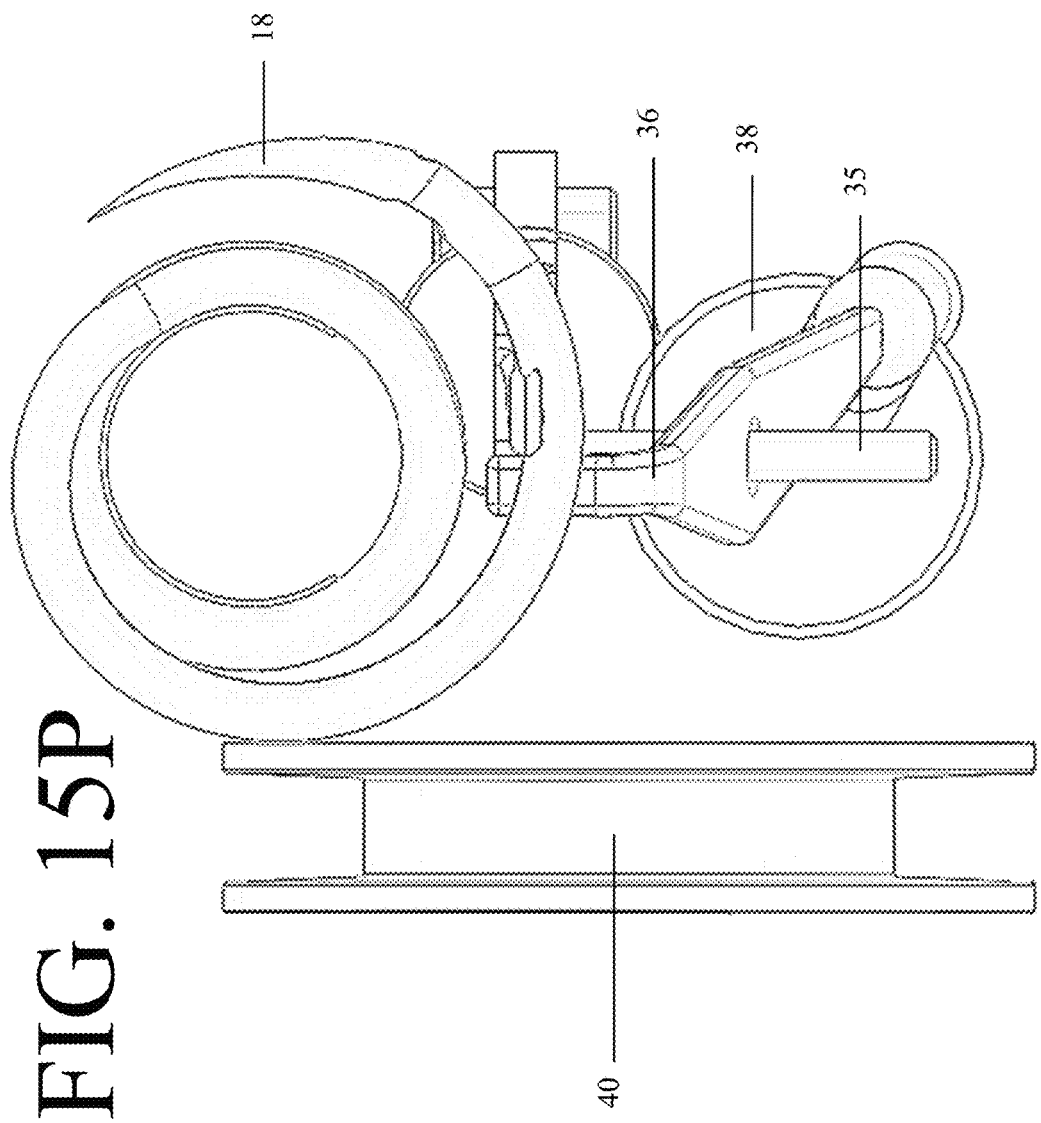

FIG. 15P shows a perspective view diagram of the complete head portion in a position of operation for completing a stitch in suturing by the machine of the present invention.

Figure 15Q:
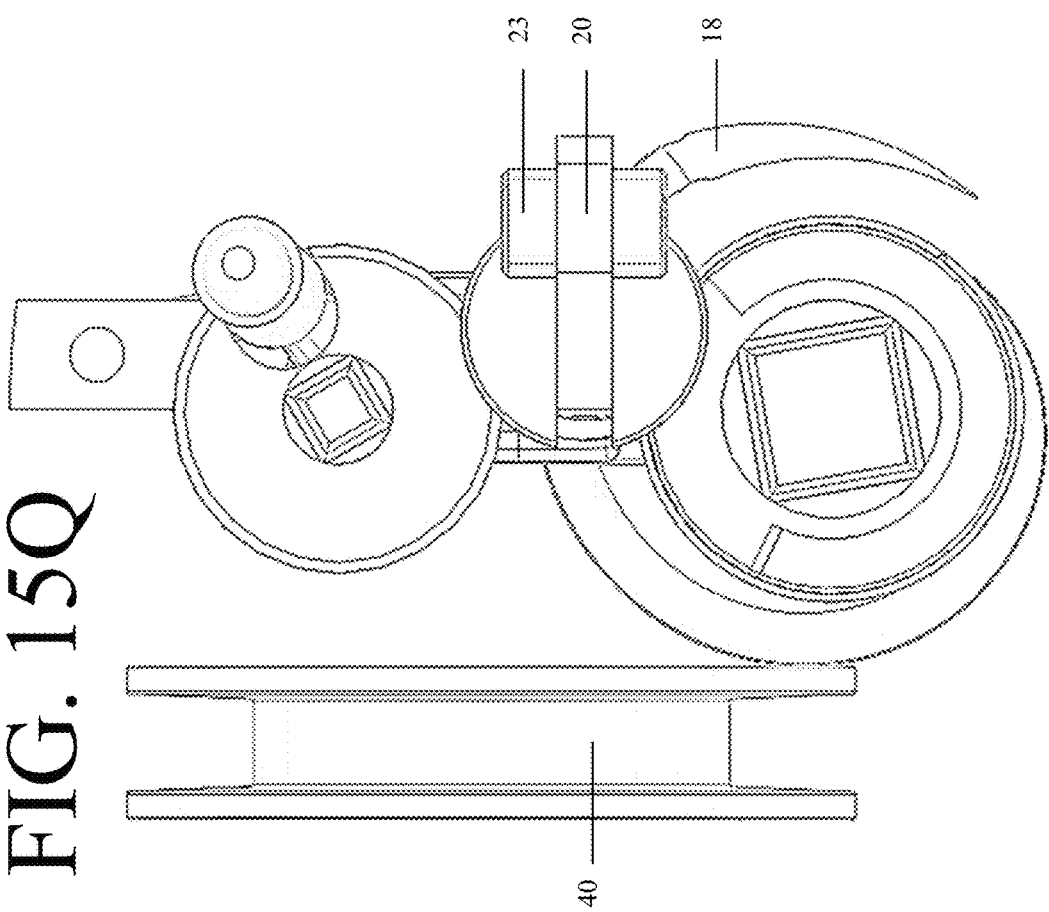

FIG. 15Q shows a perspective view diagram of the complete head portion in a position of operation for completing a stitch in suturing by the machine of the present invention.

FIG. 15R shows a perspective view diagram of the complete head portion in a position of operation for completing a stitch in suturing by the machine of the present invention.

Figure 15S:
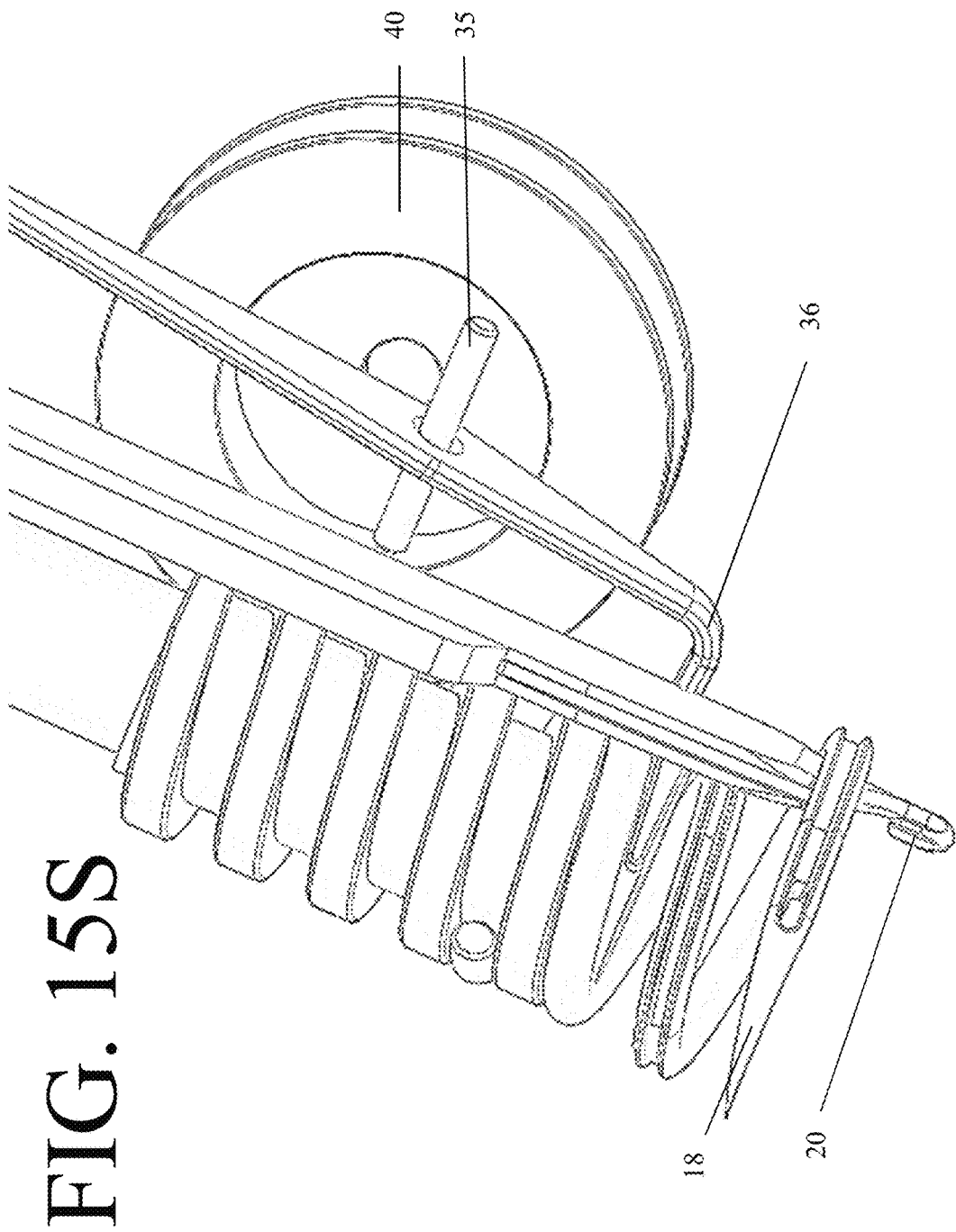

FIG. 15S shows a perspective view diagram of the complete head portion in a position of operation for completing a stitch in suturing by the machine of the present invention.

Figure 15T:
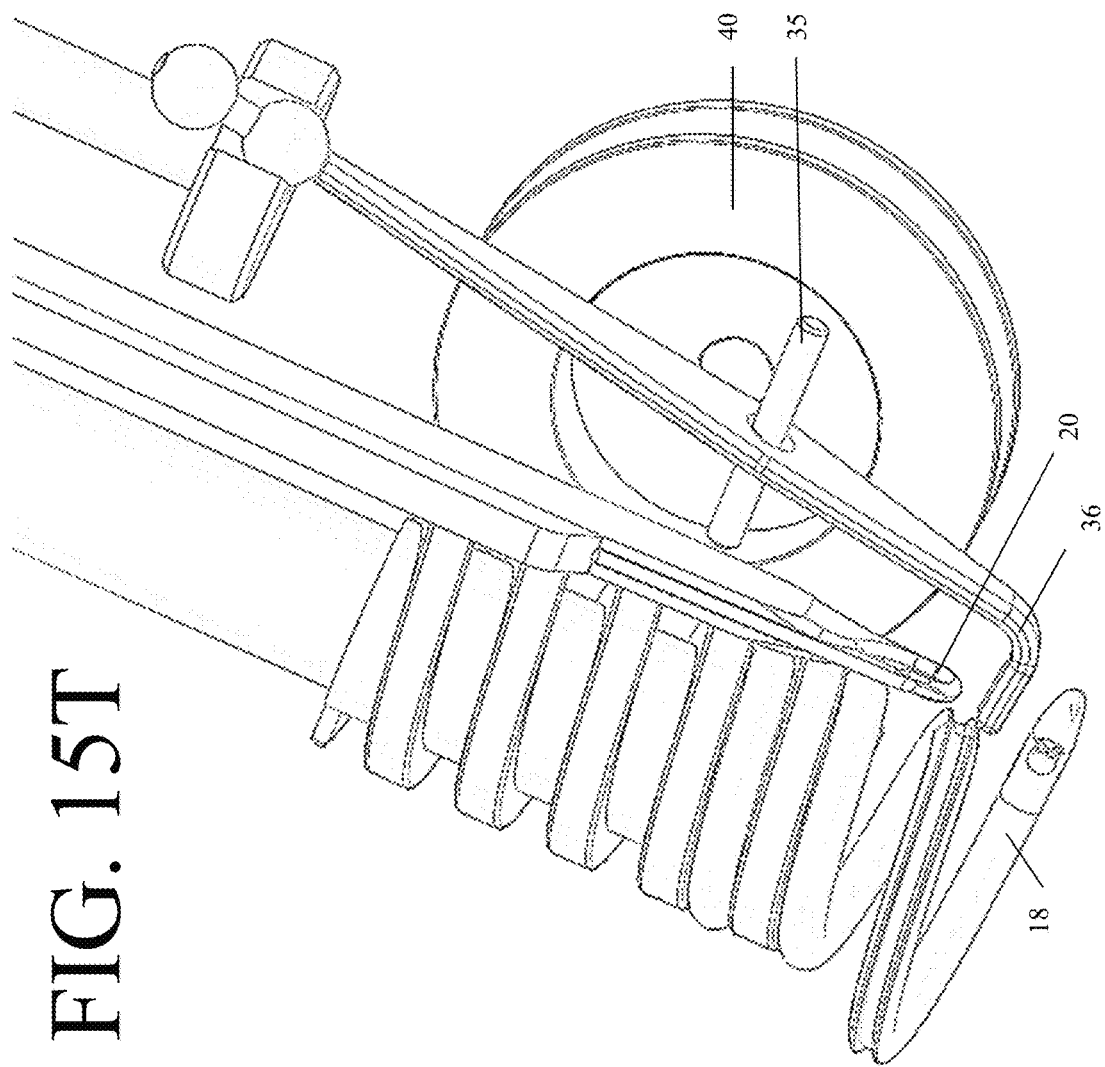

FIG. 15T shows a perspective view diagram of the complete head portion in a position of operation for completing a stitch in suturing by the machine of the present invention.

Figure 16A:
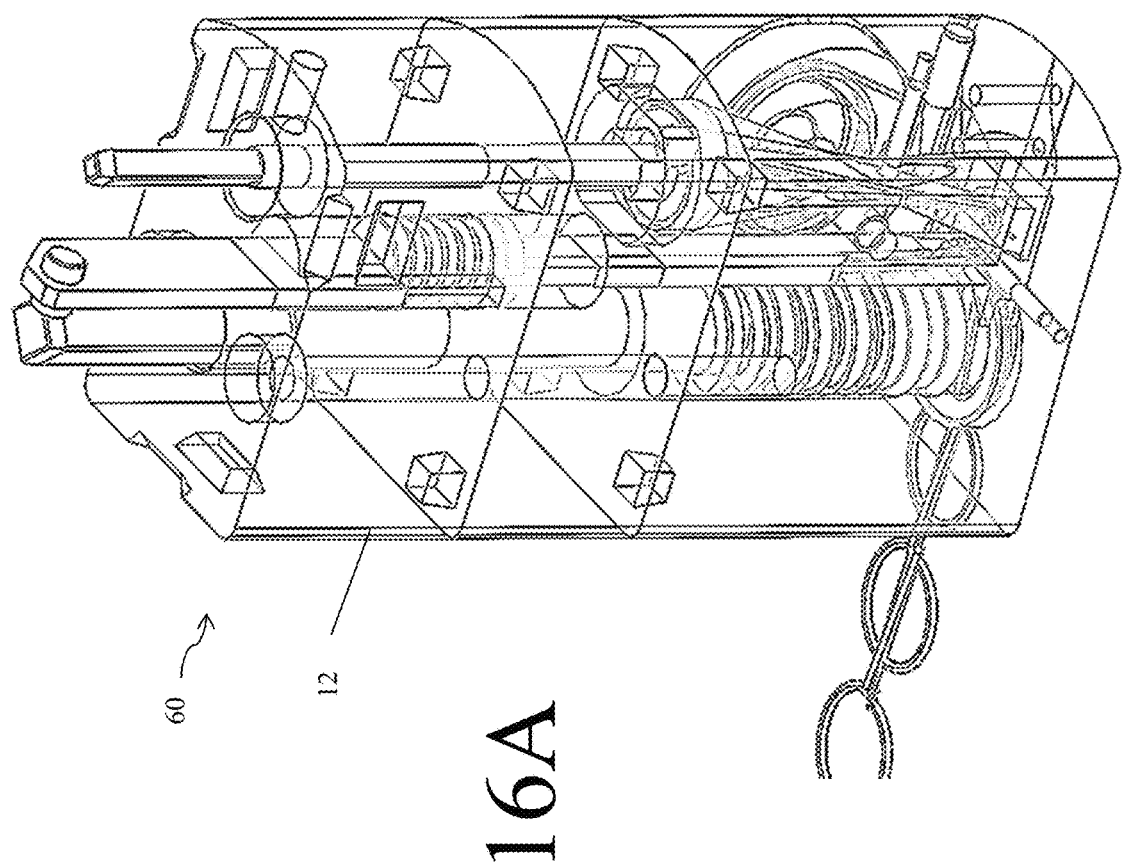

FIG. 16A shows a preferred embodiment of the complete suturing module assembly encased within a general housing of the present invention.

Figure 16B:
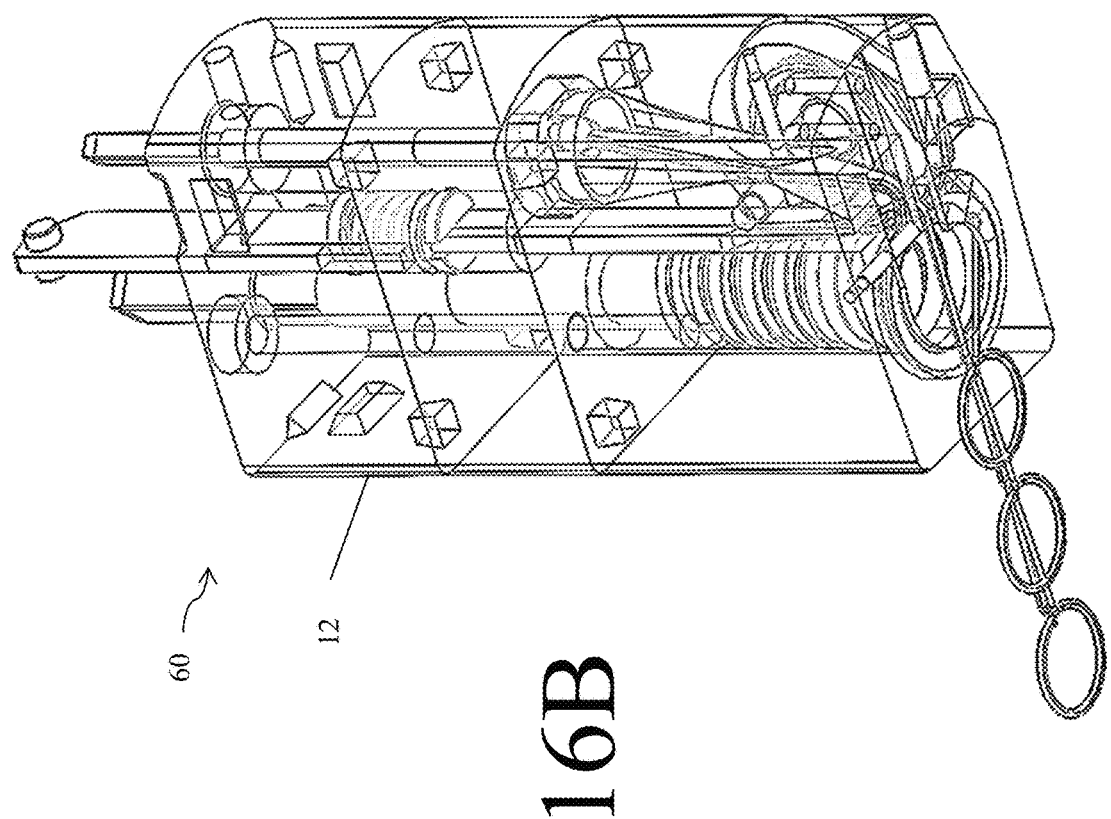

FIG. 16B shows a preferred embodiment of the complete suturing module assembly encased within a general housing of the present invention.

Figure 17A:
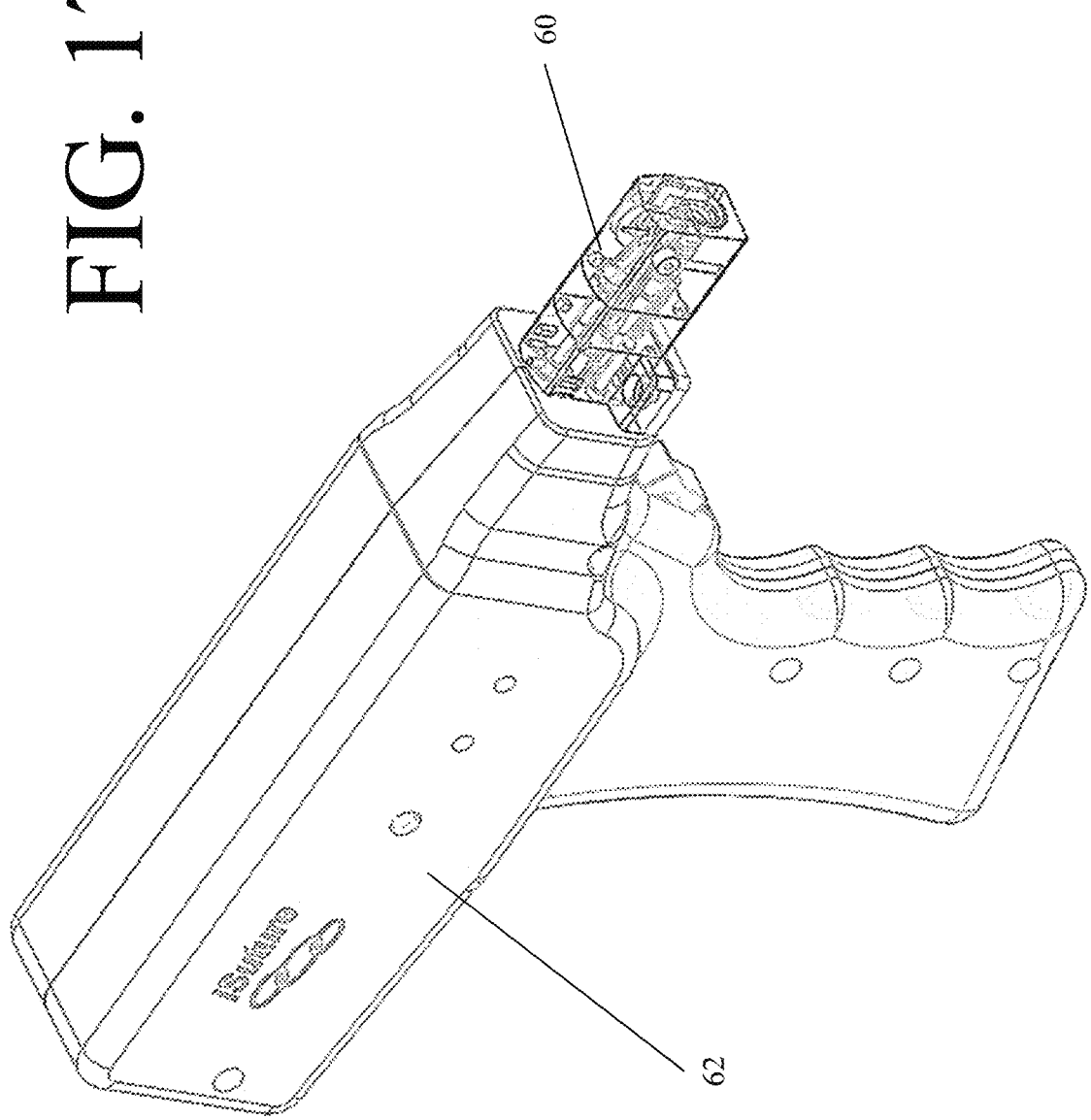

FIG. 17A shows a complete handle and suturing module assembly of the present invention.

FIG. 17B shows a complete handle and suturing module assembly of the present invention.

Figure 18A:
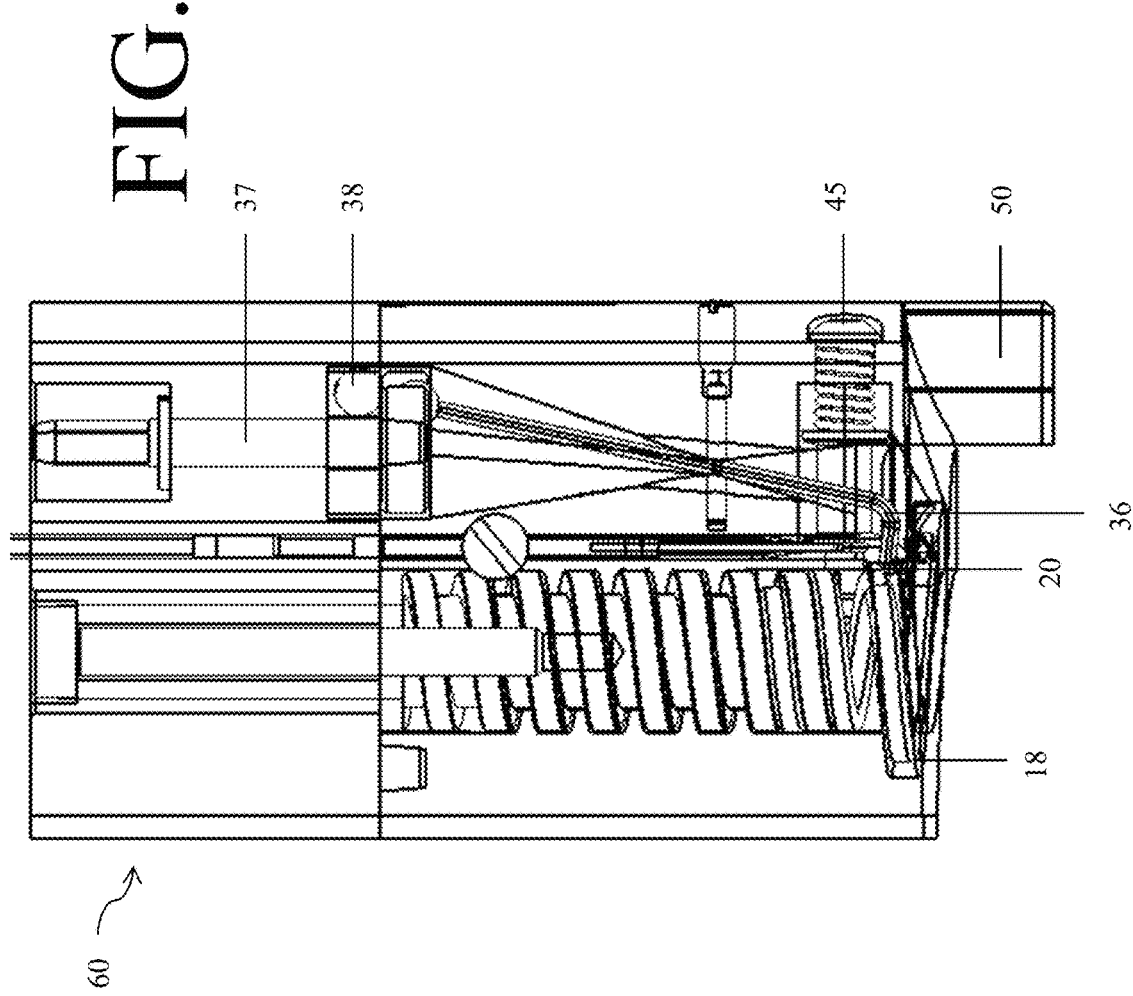

FIG. 18A shows an alternative embodiment incorporating a suture thread supply connected to a tensioner of the present invention.

Figure 18B:
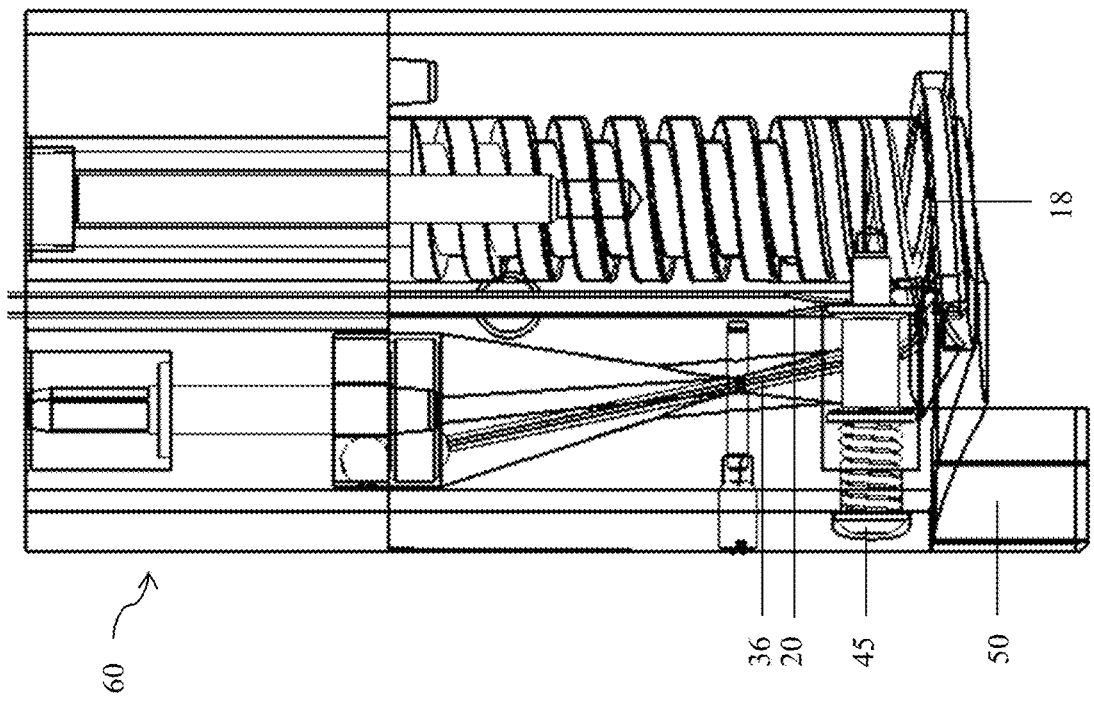

FIG. 18B shows an alternative embodiment incorporating a suture thread supply connected to a tensioner of the present invention.

Figure 18C:
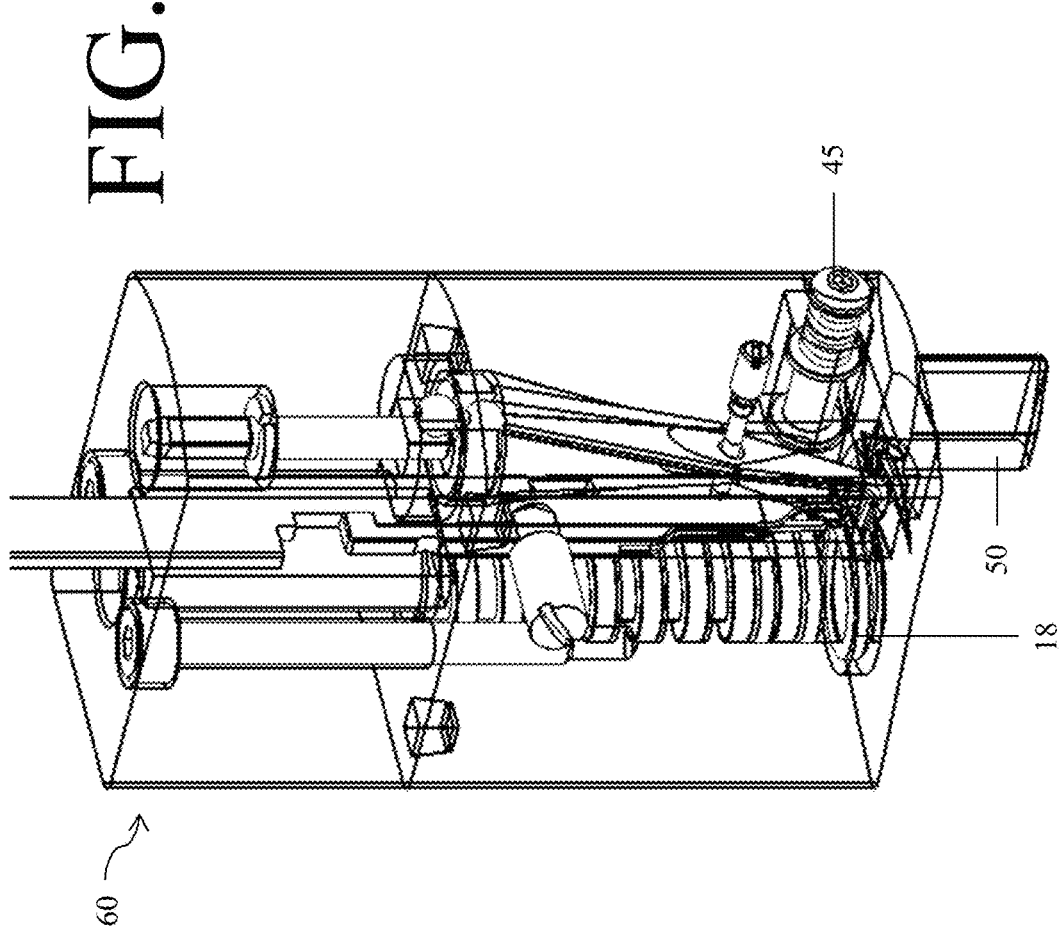

FIG. 18C shows an alternative embodiment incorporating a suture thread supply connected to a tensioner of the present invention.

Figure 19:
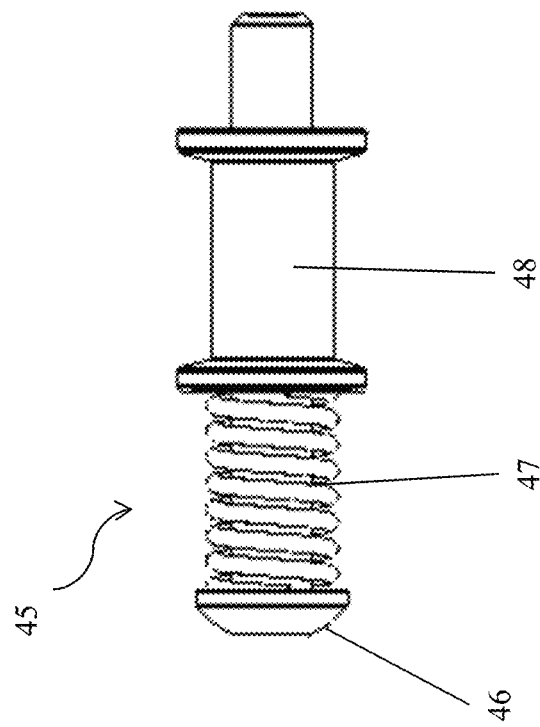

FIG. 19 shows a suture tensioner according to the present invention.

Figure 20A:
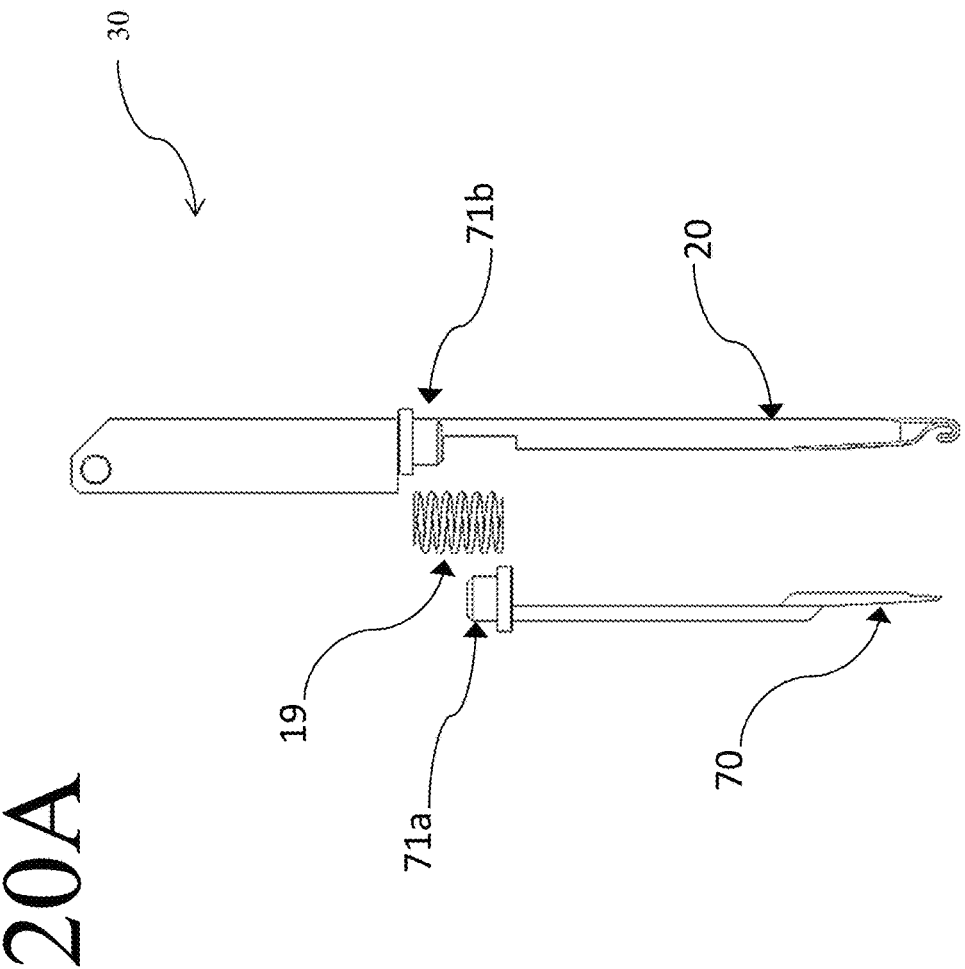

FIG. 20A shows a compound needle with a hook and closing element.

FIG. 20B shows a compound needle with a hook and closing element.

FIG. 20C shows a compound needle with a hook and closing element.

FIG. 20D shows a compound needle with a hook and closing element.

FIG. 20E shows a compound needle with a hook and closing element.

Figure 21A:
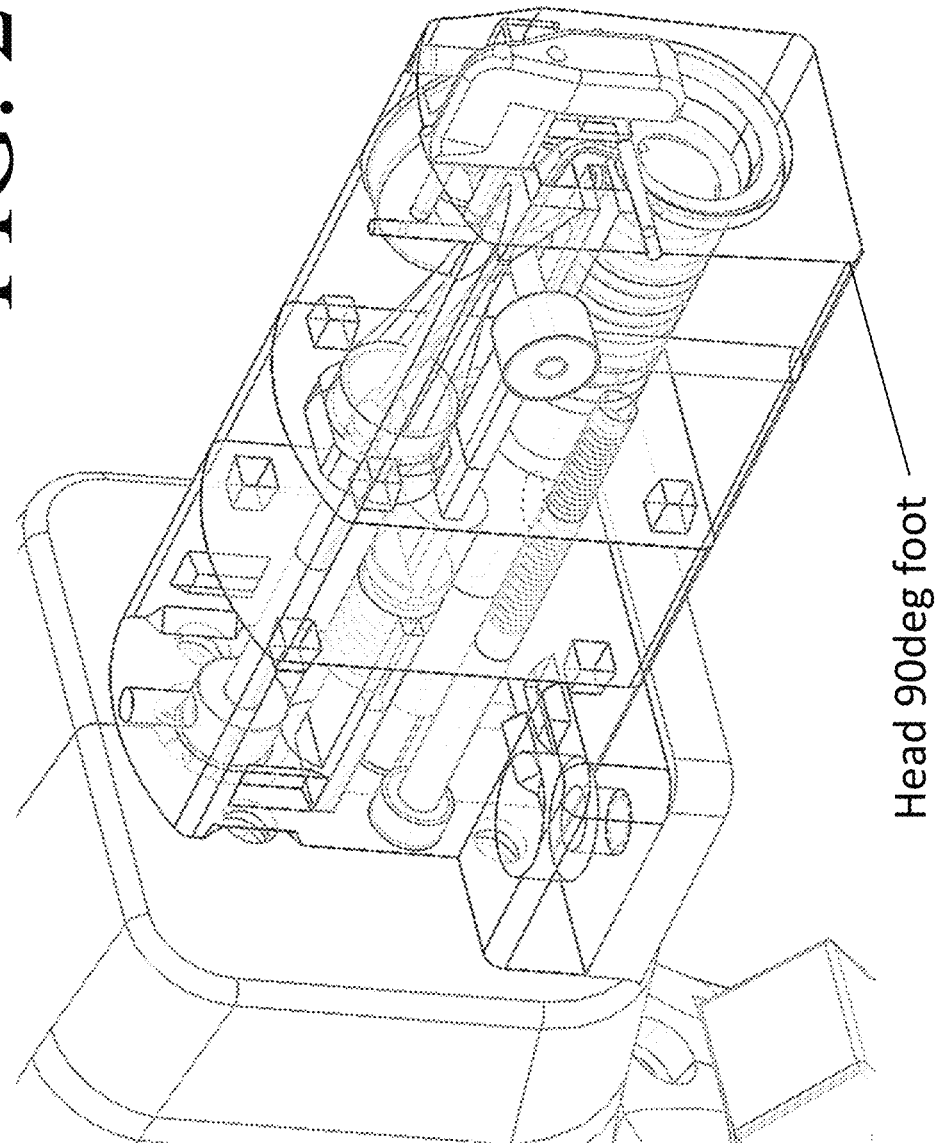

FIG. 21A shows a suturing module assembly with a 90 degree footing.

Figure 21B:
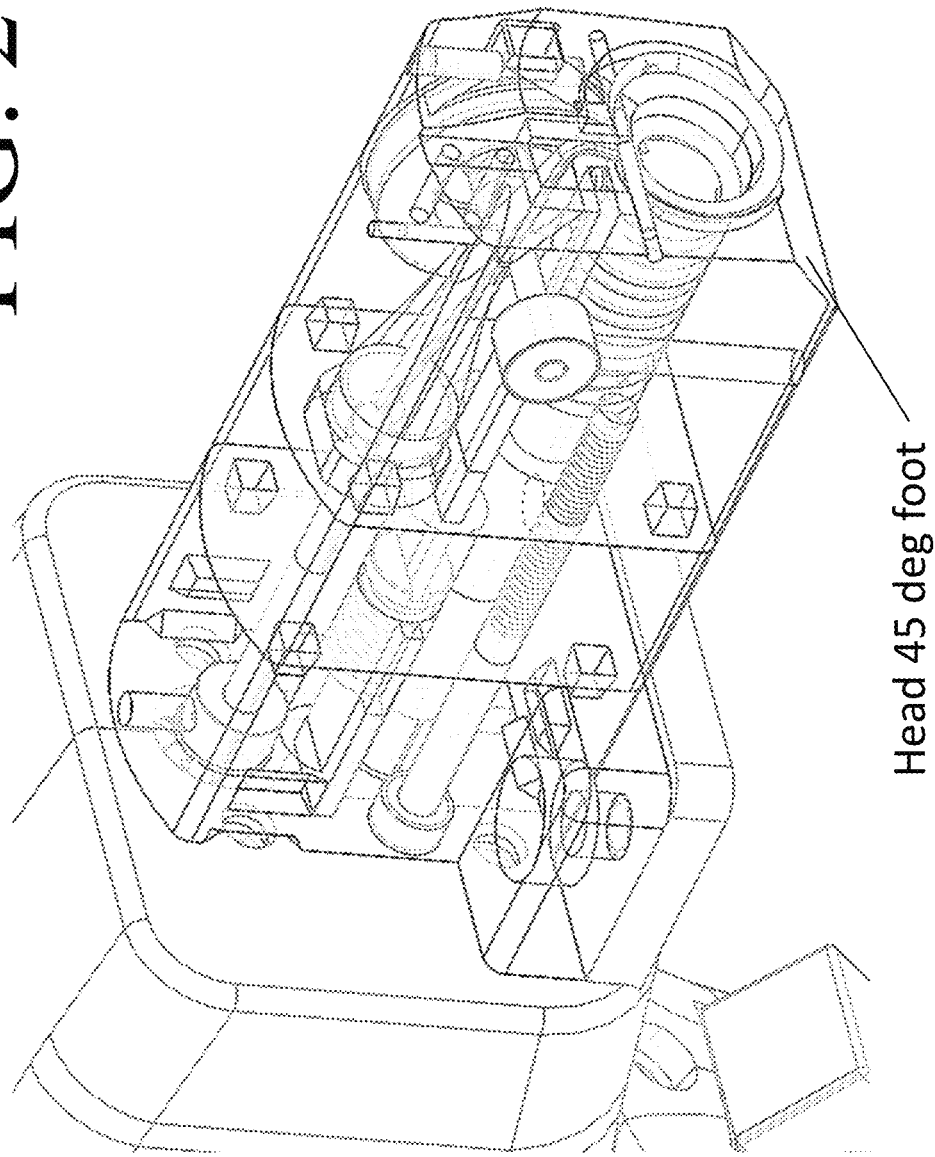

FIG. 21B displays a suturing module assembly with a 45 degree angled footing.

LIST OF INDICIA 10 machine
11 head portion
12 housing
14 suture needle plane
15 helical axis of suture needle
16 needle eyelet
17 needle shaft
18 suture needle (hollow or solid)
19 hook spring
20 hook
21 hook rod
22 retracted hook position.
23 extended hook position
24 hook shank
25 hook point
26 hook gape (gap)
27 hook bend
30 compound needle
31 push arm
33 holding arm head length
34 loop
35 holding arm spindle
36 holding arm or pusher
37 holding arm rotary shaft
38 holding arm rotary shaft wheel
39 holding arm shaft
40 thread supply
41 thread supply post
42 thread guide
43 suture, suture thread
44 catch arm
45 tensioner
46 bolt (tensioner)
47 spring (tensioner)
48 suture bobbin
49 holding arm head
50 edge separator
51 helix pitch
52 higher side of cut
53 lower side of cut
54 flat surface of footing
55 edge offset distance
60 complete suturing module assembly
62 complete handle
70 tongue
71 spring seat

DETAILED DESCRIPTION

The present invention provides a device constructed and configured for automatic suturing for reduced or minimized scarring, reducing suturing time and methods for using a machine operable for automatic suturing. Additionally, the present invention provides a variety of suture needles, designed and constructed for suturing to minimize or eliminate scarring, reducing suturing time and more particularly for use in combination with hooks for making a continuous suture stitch with a machine operable for automatic suturing for reduced or minimized scarring, reducing suturing time.

As set forth herein, the present invention provides machines, methods and suture needle designs for automatic suturing with minimum scarring and reducing suturing time. Referring now to the drawings in general, the illustrations are for the purpose of describing a preferred embodiment of the invention and are not intended to limit the invention thereto.

FIG. 1 is a perspective view diagram of the main components of the head of a device for suturing showing skin subcuticular suturing embodiment of the invention.

Figure 2:
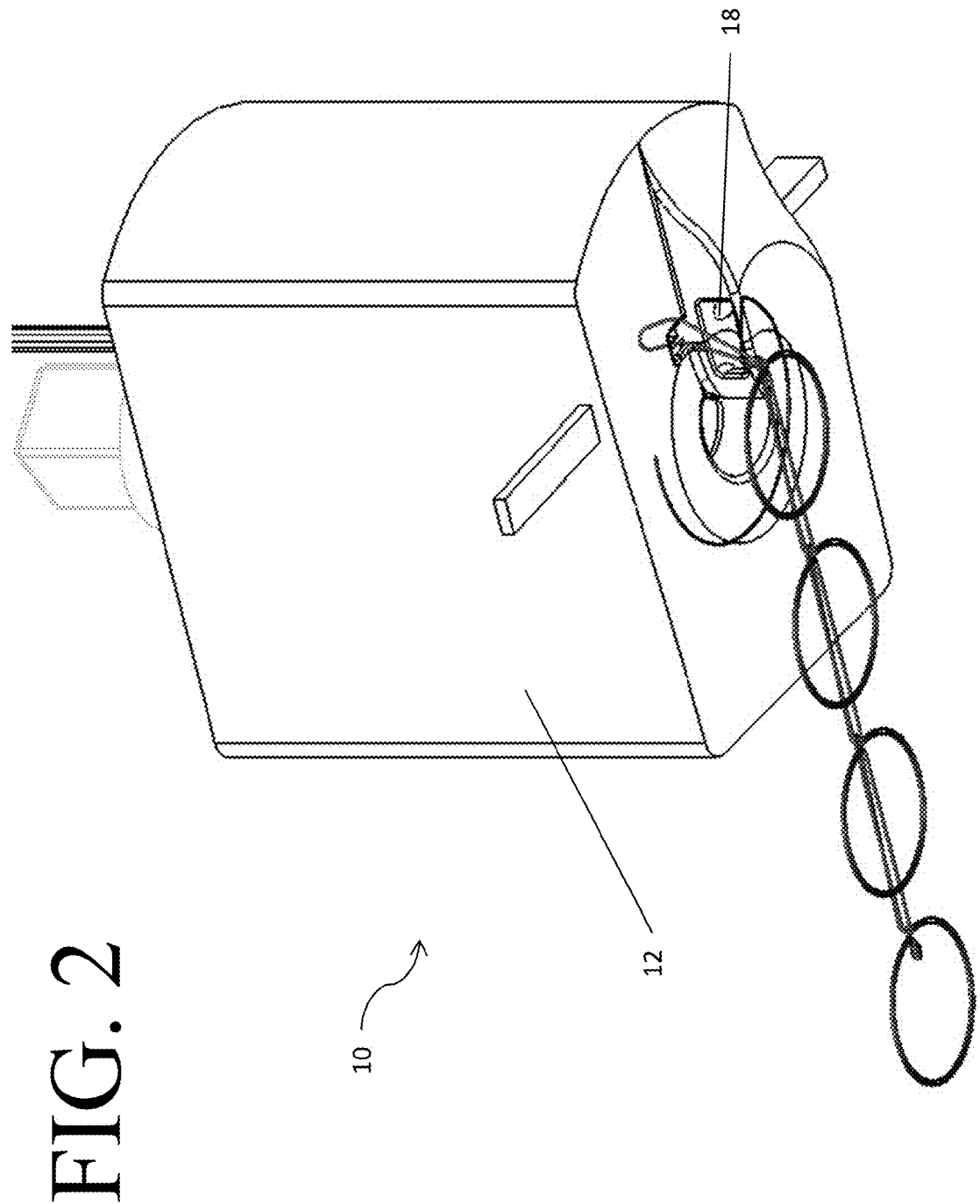
FIG. 2 is a perspective view diagram illustrating the head of a device for suturing according to one embodiment of the invention.

FIG. 2 is a perspective view diagram illustrating the main components of the head of a device for suturing according to one embodiment of the invention. FIG. 3 shows a perspective view diagram illustrating a portion of the main components of the head of a device for suturing from FIG. 2 focused on the hook and suture needle interaction for forming continuous suture stitches according to one embodiment of the invention. The suture machine is generally referenced 10, and includes at least the following components constructed and configured in operable connection for automatically producing a stitch: a support base or housing 12, a suture thread supply (not shown) having a first end and a second end, removably (movable) mounted on the support base via a connecting cylindrical post (not shown), a substantially spiral-shaped hollow suture needle 18 movable rotationally between a first (home position) and second position for forming a stitch, and a hook 20 (FIG. 3) movable between a retracted position 22 and an extended position (23, FIG. 3D, closer toward the suture needle tip than the retracted position, 22) by an automated gear device (not shown). The machine for making suture stitches automatically according to the present invention preferably includes a machine body or base for supporting or otherwise connectable to a suture thread supply, a suture needle constructed and configured for receiving and manipulating a first end of the suture thread supply, wherein the suture needle is rotationally movable so that a suture needle tip advances between a first and second position for adjoining at least two edges for continuously stitching them together in a substantially edge-to-edge interface without overlapping the edges, aided by a wound separator mounted on or part of the machine body or housing 12 ahead of the suture line (the wound separator is not shown) thereby providing an automated device for making suture stitches that produce minimal scarring on tissue, organs, or skin. The wound separator is to prevent wound overlapping.

In an automated machine for suturing according to an alternative embodiment of the present invention from FIG. 2, note that the hook device mechanism may be constructed and configured to be in an angled position; preferably, the hook device mechanism is adjustable, but in any position, the hook is always configured to be in parallel to the spiral suture needle. However, overall components and functionality are substantially similar to the foregoing description, but the angled positioning of these components is preferred for forming a "sideways" suture using a helical suture needle. The angle of the spiral suture needle axis in relation to the surface of the tissue to be sutured is preferably adjustable between about 10 degrees and about 90 degrees, wherein 90 degrees angle is perpendicular to the wound or tissue surface where the suturing is made (i.e., the suturing zone), preferably between about 25 and about 90 degrees, and more preferably between about 45 and about 90 degrees. The application and type of suture are factors affecting the angle. The angles provide for creating hidden sutures and in the use of suturing fascia, muscles, or hollow organs, such as the intestines, wherein the skin adjoined by the sutures is substantially or perfectly flat, and without overlap, thereby minimizing scarring.

FIG. 2 is a perspective view diagram illustrating the head of a device for suturing according to one embodiment of the invention.

FIG. 3 shows a perspective view diagram illustrating a portion of an automated machine for suturing from FIG. 2 focused on the hook and suture needle interaction for forming continuous suture stitches according to one embodiment of the invention.

FIG. 3 views A, B, C, D, E, F, G, H, I, and J illustrate a perspective view diagram of the portion of the automated machine of FIG. 3 shown in various positions of operation for a single cycle completing a stitch in suturing automated by the machine of the present invention.

FIG. 3 shows a perspective view diagram illustrating a portion of an automated machine for suturing according to one embodiment of the invention. Furthermore, FIG. 3 views A, B, C, D, E, F, G, H, I, and J illustrate a perspective view diagram of the portion of the automated machine of FIG. 3 shown in various positions of operation for a single cycle completing a stitch in suturing automated by the machine of the present invention. By moving through this cycle automatically, a hook 20 is moved by a rotating gear (not shown) between a first retracted position (FIG. 3A) after catching a loop 34 made with the suture thread that is picked up next by a holding arm comprising a push arm 31 and a catch arm 44. The push arm 31 and catch arm 44 coordinate movements as shown in positions B, C, D, and E to allow the hook to move into a second extended position to release the loop and then move to catch the next loop (if any, depending on the length of the chain of stitches) illustrated in F and G positions. In this method, the suture stitch is formed of a series of interconnected loops (single stitch unit cycle is illustrated in FIG. 6; continuous series illustrated in FIGS. 7A, 7B, 7C) by the cooperation, coordination and synchronization of the suture needle and hook components to effectively knit the suture stitches into a connected chain that is continuous and substantially planar.

Methods for making suture stitches automatically according to the present invention include the steps of: providing a machine having a suture thread supply, a suture needle constructed and configured for receiving and manipulating a first end of the suture thread supply, rotationally moving the suture needle and thread to create a suture stitch by advancing the suture needle position, and adjoining at least two edges for continuously stitching them together in a substantially edge-to-edge interface, thereby making suture stitches that produce minimal scarring on tissue, organs, or skin and reducing suturing time.

In preferred methods, the step of moving the suture needle rotationally to create a suture stitch is automatically made, by activating the machine to move the suture needle to create a first rotational part of the stitch, introducing a hook in a retracted position to catch the stitch at the end of the rotational movement, reversing the direction of rotation of the suture needle, moving the hook to a second extended position and releasing the stitch, and extracting the suture needle to complete the stitch. After the suture needle and hook form a single stitch, or a series of connected stitches, depending upon the size of the suture area, preferably the suture thread will be cut, by scissors, or other sharp utensil. Additional cutting mechanism (not shown) can be added to the body of the machine such as a vertical blade retracted in a groove in the body of the machine. Such blade has a distal sharp flat end and blunt proximal end. The distal end is close to the stitch loop when such loop is pulled up by the hook in a retracted position inside the body of the machine. The proximal end is connected to a spring loaded button that is operated manually by the surgeon. At the end of the suture line, the surgeon can go back and forth with continuous suturing to ensure the security of the suture end. Then the surgeon pushes the button, which in return pushes the rod down to let the distal sharp flat end cut the suture material and to end the continuous line of suturing.

FIG. 6 shows a top view diagram illustrating a stitching pattern for a single unit cycle for making continuous suturing made by an automated machine for suturing according to one embodiment of the invention.

FIGS. 7 A, B, and C illustrate in perspective views three alternatives for continuous suture stitching forming chains of single unit cycles illustrated from FIG. 6.

A suture stitch single unit cycle formed from the method described hereinabove is illustrated in FIG. 6, and in FIGS. 7A, 7B, and 7C, it is shown in one continuous suture stitch chain embodiment formed from a series of interconnected stitches by repeating the foregoing steps: FIG. 7A shows 5 units repeated and in a spaced apart manner so that the circular portion of the stitch unit cycle does not directly touch or is not directly juxtaposed another stitch unit cycle; FIG. 7B shows 7 units repeated that are directly touching, i.e., the circular portion of the stitch unit cycle is formed and positioned so that it is directly or approximately directly juxtaposed the next stitch unit cycle; FIG. 7C shows 5 stitch unit cycles wherein the circular portion of each unit cycle is overlapping with an adjacent stitch unit circular portion. The method of forming the stitch includes rotational movement of the suture needle via rotation of a shaft along its axis. Then parallel to the suture needle shaft (shown in FIG. 3), a hook catches the loop formed by the suture thread from the rotational suture needle movement (before or just after the suture needle reverses direction) and the hook pulls the loop out of the plane, as illustrated in FIG. 3 and FIG. 3 views, for forming a chain or continuous connection of a series of loops formed by the suture needle movement of the suture thread (single stitch unit cycle illustrated in FIG. 6; continuous suture stitching embodiments illustrated in FIGS. 7A, 7B, and 7C).

FIG. 8 shows three perspective views 8A, 8B, and 8C each illustrating a solid suture needle in alternative embodiments for use in suturing according to the present invention.

FIG. 9 shows three perspective views 9A (spiral suture needle), 9B (helico-spiral suture needle), and 9C (helical suture needle) each illustrating a hollow suture needle in alternative embodiments for use in suturing according to the present invention.

For a spiral suture needle as in FIG. 8A or FIG. 9A, or for the helico-spiral suture needle FIG. 8B or 9B, the hook is positioned preferably at 90 degree angle to the suture needle. For a helical suture needle, as illustrated in FIGS. 8C, 9C, the hook is preferably positioned at an angle with respect to the suture needle. For using a latch hook as in FIG. 10A, the process is not entirely dissimilar from knitting methods for creating a continuous chain of loops; however, an alternative embodiment for the machine is required (completely different from knitting machines and methods, requiring an additional catcher mechanism) when using a non-latch hook as illustrated in FIGS. 10B and 10C; in preferred embodiments, the shorter hook of FIG. 10B is used.

As illustrated in the figures, the present invention and machine and methods of using same further include a spiral-shaped suture needle for making suture stitches wherein the suture needle includes a continuously hollow suture needle body having a first end positioned a spaced apart distance from a second pointed, sharp end, wherein the suture needle body forms a spiral having at least two complete turns around a center point, wherein the second end is positioned at the outermost spiral. As shown FIG. 9 provides three perspective views 9A, 9B, and 9C each illustrating a suture needle in alternative embodiments for use in suturing and for use with an automated machine for suturing of the present invention. The suture needle body is an elongated metal cylinder that is formed and configured to be spiraled for forming the stitch for suturing in an edge-to-edge manner without substantial overlapping of the tissue, skin or organ. The important dimensions for the suture needle are the diameter; the height is a secondary dimension consideration. For a hollow suture needle, the suture needle tube outer diameter is preferably between about 1 mm and about 3 mm; more preferably between about 1 mm to about 2 mm. The suture needle spiral dimension is between about 5 mm to about 25 mm; more preferably between about 5 mm and about 15 mm. For the solid suture needle, the same outer diameter and the suture needle spiral dimension apply. The dimensions for the suture needle depend upon the type and size of suture thread, type and nature of tissue being connected with the suture (e.g., facial skin would require a finer suture needle with smaller dimensions), and other factors, including whether it is an open wound or inside the body, the size and dimensions of the device or machine, and the like. Also, the length of the suture needle is dependent upon the number of coils in the spiral, which is a function of the application, or the type of suture thread, type of tissue being connected with the suture, etc.

By way of example, typically used for the skin, 5/0 monocryl suture, the suture needle will have outer diameter of 0.36 mm and curvature of 11 mm. For fascia, muscles, and internal organs, such as intestines, larger size sutures from 4/0 up to about #2 would require much larger suture needle and curvature. Smaller sizes would be used for microsurgery, and eye surgery.

FIG. 11 from Ethicon shows commercial suture materials and prior art suture needle references.

FIG. 12 from Johnson & Johnson shows commercial suture needle information references.

In one embodiment, preferably the second pointed sharp end is angled to form an ovular opening in the suture needle body. Such opening is preferred to have smooth rounded edges to allow the suture material to slide easily with minimal friction especially if used with the hollow helico-spiral suture needle. Preferably the suture needle further includes an opening spaced apart from the second pointed sharp end of the suture needle for forming the suture stitch and to allow the suture thread to exit at the side or edge of the tissue.

A latch needle or spring needle or hybrid of both may be used with machines of the present invention. Steps for methods of using these knitting needles with or without the machines of the present invention include: inserting the suture needle at the point or location for the first suture stitch; catching the suture stitch with the hook; pulling out the suture needle by reversing its rotation; the hook releasing the loop; holding the loop by the catcher, hooking the next loop by the hook and pulling it through the previous suture stitch loop (illustrated by the positions of machine components in FIG. 3A-G) to form a substantially parallel series of continuous loops along the suture tissue line. In a significant difference from knitting known in the prior art, the stitching of loops for forming the sutures of the present invention are formed in a single flat line and only connected on a single side of the loop of the stitches, as illustrated in FIG. 6.

FIG. 6 illustrates a view showing single side loops that are connected.

The bottom loop goes through the opposing side loop for interconnecting and closing the wound from both sides. These illustrations in the figures provide step by step methods for making the suture according to the present invention, and also show the device and/or machine component positioning and configuration at each step. Depending upon where the next stitch entry is made determines the pattern and closure for the suture stitch; three embodiments of suture stitch chains are illustrated, from spaced apart non-interlacing or overlapping loops; to another view showing adjacent loops that are juxtaposed but not overlapping; and a third view showing overlapping or interlacing loops or stitches. In each example embodiment, a perspective view is shown.

In preferred embodiments, it is better to stretch the stitch longer, i.e., to make the circular loops stretched (each loop circle is stretched longer); it is helpful for the purposes of this detailed description of the invention to consider each loop as a unit cell. Depending on a link from each end of the unit cell, determines how tightly each unit cell is positioned. Each entry into the skin/tissue/organ is more distantly spaced apart.

FIGS. 8C, 9C show a perspective views for one of the suture needle configurations, although it is not preferred, since there are too many coils, which makes more friction for the suture inside. It would be preferred to place the suture outside that needle when it is used.

FIGS. 8A, 9A show another compact view of a suture needle embodiment of the present invention; however, it is likewise not the preferred embodiment, because when the suture needle starts to rotate, there is still a need to squeeze the wound to press together the wound edges to be stitched. Position of hook would be straight for A, which is acceptable, but not preferred.

FIGS. 8B, 9B are preferred suture needle types (solid more preferred than hollow) and illustrate a hybrid between the A and C configurations, where part of the spiral shape is helical; Thus, the needle is not completely conical; it instead progresses from spiral to helical, and is the preferred needle embodiment—the helical-spiral (or helico-spiral) hybrid suture needle. A conic spiral (not shown) is another possible configuration for the suture needle.

A compact device embodiment is preferred, wherein the last circle of the suture needle component is spiral, with two helical and last one on bottom is spiraled out wider; the latch needle is positioned to be operable in a vertical up and down movement. In methods preferred and illustrated in this figure, steps are included to catch the loop from both sides so that a catch makes a loop of the suture on both sides; on one cycle there is a catching mechanism to catch from left side; then a step to pull the latch mechanism up; then a step to retract the spiral needle; then the catcher and the latch needle (hook) work together to catch the loop on the other side, so it goes through first loop and pulls through the second loop, and each time comes from one side of the wound. One time it is at an acute angle; one time straight.

By way of preferred embodiment for an example or prototype of the present invention, a solid suture needle is provided with helical-spiral shape. While a hollow suture needle is possible, at the time of the invention example, it is practically easier to make a device according to the present invention with a solid suture needle. One reason is that it is easier to pull out the suture to make the wound tighter; another is that it is also easier to use a solid suture needle in combination with a spring-based or lever-based tensioner or tension-providing mechanism. A commercial reason for preferring a solid suture needle instead of a hollow suture needle configuration is that the hollow suture needle is more expensive to produce. Also, there is some difficulty threading it, and in operation, there is additional friction and tension in the suture needle since the suture thread passes through and contacts the needle's internal surfaces in this hollow suture needle configuration. For these reasons, in the preferred embodiments at the time of the present invention, non-hollow suture needle components are used in prototype experimentation.

Note that in FIG. 3 and the various FIGS. 3A-3J, all illustrations show the continuous suture stitch beginning with a knot. Now regarding the illustrations of FIG. 3 and FIGS. 3A-3J, starting from position zero in the formation of a single suture stitch unit cycle the steps are as follows:

Position zero. The hook is positioned up; the catcher has a multiplicity of positions, preferably with 3 positions: home, catch, and push positions that are illustrated in the various figures. The catcher hooks the loop when the catcher is positioned in a second position, and it is also hooked on the loop at that time. Two alternatives are considered in prototype versions of the embodiments of the present invention that use a vertical latch needle: 1) go through the loop exactly; and/or 2) go through the loop & past it. If the first alternative is used, then the methods for making sutures according to and with the device and machine according to the present invention provide for the following steps: pushing the suture to that position to make a space for the hook to go exactly through the loop. In this step, it is very important for safety that there be adequate space for the hook to move exactly through the loop, otherwise it is possible to lose at least one stitch in the next or following step(s).

The suture goes through the hole in the helical spiral hybrid suture needle and through the tube (in the case of a hollow suture needle embodiment) up to the spool. In a prototype version according to one embodiment of the present invention, the suture goes through the suture needle and through the body on the right side for pulling the suture with an additional mechanism. Again, for commercial application, the solid or non-hollow suture needle is preferred over use of application of hollow suture needle configuration since the hollow suture needle is expensive to produce, there is some difficulty threading it, and there is additional friction and tension in the suture needle during its use in methods of the present invention, since the suture thread passes through and contacts the needle's internal surfaces in this hollow suture needle configuration. Also, a hollow needle may "core" the tissue, creating even more friction inside the needle. For these reasons, in the preferred embodiments at the time of the present invention, non-hollow suture needle components are used in prototype experimentation.

Again, referring to the method steps illustrated in FIG. 3 and FIGS. 3A-3J. Once the final position zero is returned to, a single unit cell or unit cycle is completed.

Position 1. For the next bite or next step in forming a continuous suture stitch chain as illustrate in the Figures: shift the entire mechanism forward. The way the mechanism shifts and how the suture goes from the helico-spiral suture needle and pulls the loop held by the hook. If additional tension or pull is provided on the loop, it makes the wound tighter.

Position 2. First bite or suture needle entry into the wound. Hole in suture needle near tip or sharp end to show how the suture thread or suture material exits the suture needle and goes to tensioning device.

Position 3. Rotation is 45 degrees from p1 to p2. This is now 360 degrees rotation. Radius of suture needle is smaller than the first rotation from the tip of the suture needle b/c spiral.

One suture all the way up; 2d goes through the wound.

The figures also show stitched loops with reference to left side of wound; right side of wound.

Next the final position of the helico-spiral suture needle before catching the suture is shown.

Catcher pushes the loop from the hook. The vertical needle hook is lower; catcher pushes the loop & holds it in a position. At that point the hook starts moving down exactly through the loop because it's held in 2 directions horizontal and vertical to assure that one loop goes through another; this is critical in the methods of the present invention.

After that hook goes through the lower position, close to the helico-spiral suture needle to ensure that the hook passes through the space between the suture and the helico-spiral suture needle to be ready to catch the loop.

At the bite, it is from the front side of the loop. When the suture needle rotates, diagram 3D, the suture needle is positioned below the loop. The helico-spiral suture needle rotates backwards 45 degrees and the hook captures the next suture, and then pulls out the next loop. The prior loop is inside of the helico-spiral suture needle.

The new loop is pulled through the prior loop. Next the hook is positioned up; pusher retracts. Before retracting catcher to right, the hook is pulled up. Then retract the catcher. The chain is now made forming the circular portion for the continuous suture stitch. Next the catcher moves or is pushed to catch the next loop (the new loop).

Then go to or return to position zero (0).

The method steps are focused on one bite at a time for these steps in the exploded partial views of the FIGS. 3, 3A-3J.

FIGS. 13A-13K are perspective view diagrams of the complete head portion in various positions of operation for a single cycle completing a stitch in suturing automated by the machine of the present invention. This view displays the complete components of the head portion, and the drawings in order will provide an embodiment of the device's functional process and features. The suture machine is generally referenced 10, and incldes at least the following components constructed and configured in operable connection for automatically producing a stitch: a suture thread supply (not shown) having a first end and a second end, removably (movable) mounted on the support base via a connecting cylindrical post (not shown), a substantially spiral-shaped hollow suture needle 18 movable rotationally between a first (home position) and second position for forming a stitch, a holding arm 36 for pushing the suture thread 43, and a hook 20 movable between a retracted position 22 (FIGS. 13A, 13B, 13F-13K) and an extended position 23 (FIGS. 13C-13E) by an automated gear device (not shown). The suture needle 18 is connected to a suture needle shaft 17. The holding arm 36 revolves around a spindle 35 and is attached to and moved by the holding arm rotary shaft 37 and rotary shaft wheel 38. The hook is connected to a spring 19 that is connected to and completely surrounds the hook rod 21.

Referring to the method steps illustrated in FIGS. 13, 13A-13K. The home position for the major components: suture needle 18, hook 20, and holding arm 36 (FIG. 13A). The suture needle shaft 17 takes a bite by rotating down and in helical direction of suture needle 465 degrees forming a circular loop (FIG. 13B). The hook 20 moves to extended position 23, moving through and past the loop of the previous stitch held by the holding arm 36 and below the plane of the suture needle 18 (FIG. 13C). The suture needle 18 rotates backward 30 degrees against helical direction to an intermediate position to form a loop suture (not shown) for current cycle (FIG. 13D). The hook 20 is locked picking up loop of current cycle (FIG. 13E). The hook 20 moves to intermediate retracted position holding suture thread loop out of plane of suture needle 18 (FIG. 13F). The holding arm or pusher 36 grabs suture thread and is rotated to push loop of previous stitch away from hook 20 and to hold loop in this position (FIG. 13G). The hook 20 moves to fully retracted position pulling suture thread 43 exactly through extended chain loop of previous stitch and tightening loop (FIG. 13H). The suture needle 18 rotates back to home position; the holding arm 36 releases loop of previous stitch to close current circular stitch (FIG. 13I). The hook 20 moves to home position and suture machine is forwardly repositioned to meet desired suture chain configurations (FIG. 13J). The holding arm or pusher 36 returns to home position pulling previous chain loop aside in preparation for next cycle (FIG. 13K).

FIGS. 14A-14K is a perspective view diagram from an inferior angle of the head portion of operation for a single cycle completing a stitch in suturing automated by the machine of the present invention. This view displays a focus of the head portion, and the drawings in order will provide an embodiment of the device's functional process and features. The head portion is generally referenced 11, and includes at least the following components constructed and configured in operable connection for automatically producing a stitch: a suture thread supply 41, thread guide 42, hook 20, suture needle 18, and holding arm 36.

Referring to the method steps illustrated in FIGS. 14, 14A-14K. The component position in these figures corresponds to the component position of FIGS. 13A-13K. The home positions for the major components—suture needle 18, hook 20, and holding arm 36—and the suture needle eyelet 16 are shown (FIG. 14A). The suture needle shaft 17 takes a bite by rotating down and in helical direction of suture needle 465 degrees forming a circular loop; the helical axis of suture needle 15 and circular plane of suture needle 14 are displayed (FIG. 14B). The hook 20 moves to extended position 23, moving through and past the loop of the previous stitch held by the holding arm 36 and below the plane of the suture needle 18; the hook point 25, hook bend 27, and hook gape (or gap) 26 are displayed (FIG. 14C). The suture needle 18 rotates backward 30 degrees against helical direction to an intermediate position to form a loop suture (not shown) for current cycle; the hook shank 24 is displayed (FIG. 14D). The hook 20 is locked picking up loop of current cycle (FIG. 14E). The hook 20 moves to intermediate retracted position holding suture thread loop out of plane of suture needle 18 (FIG. 14F). The holding arm or pusher 36 grabs suture thread and is rotated forward pushing loop of previous stitch away from hook 20 and holding loop in position (FIG. 14G). The hook 20 moves to fully retracted position pulling suture thread exactly through extended chain loop of previous stitch and tightening the loop; the holding arm head 49 and holding arm shaft 39 are displayed (FIG. 14H). The suture needle 18 rotates back to home position, and the holding arm 36 releases loop of previous stitch to close current circular stitch; the holding arm head length 33 is shown (FIG. 14I). The hook 20 moves to home position and suture machine is forwardly repositioned to meet desired suture chain configurations (FIG. 14J). The holding arm or pusher 36 returns to home position pulling previous chain loop aside in preparation for next cycle (FIG. 14K).

FIGS. 15A-15T are multiple perspective view diagrams from of the complete head portion of the suture machine. The head portion includes at least the following components: a cylindrical post for thread supply 40, thread guide 42, hook rod 21, suture needle shaft 17, holding arm rotary shaft 37, rotary shaft wheel 38, hook 20, suture needle 18, and holding arm 36.

Referring to the perspective views in FIGS. 15, 15A-15T, FIG. 15A shows a left sagittal perspective view of complete head portion in home position, including hook rod 21, suture needle shaft 17, holding arm rotary shaft 37, rotary shaft wheel 38, hook 20, suture needle 18, holding arm 36, and cylindrical post for thread supply 40. FIG. 15B shows a left sagittal perspective view of complete head portion in home position without cylindrical post for thread supply. FIG. 15C shows a right sagittal perspective view of complete head portion in home position without cylindrical post for thread supply 40; the thread guide 42 is shown. FIG. 15D shows a right sagittal perspective view of complete head portion in home position with cylindrical post for thread supply 40 and thread guide 42. FIG. 15E shows an anterior perspective view of complete head portion in home position. FIG. 15F shows a posterior perspective view of complete head portion in home position. FIG. 15G shows an inferior perspective view of complete head portion in home position with edge separator 50 in foreground. FIG. 15H shows an inferior perspective view of complete head portion in home position without edge separator allowing view of holding arm 36, holding arm rotary shaft wheel 38, and hook 20. FIG. 15I shows a right sagittal-anterior perspective view of complete head portion with suture needle 18 in first bite position rotated 465 degrees and hook 20 in extended position 23. FIG. 15J shows a right sagittal-anterior perspective view of complete head portion with suture needle 18 rotated backward 30 degrees and hook 20 retracted to lock position to catch thread loop (not shown). FIG. 15K shows a left sagittal perspective view of complete head portion with suture needle 18 in first bite position rotated 465 degrees, hook 20 in extended position 23, and cylindrical post for thread supply 40. FIG. 15L shows a left sagittal perspective view of complete head portion without cylindrical post for thread supply 40 and with suture needle 18 in first bite position rotated 465 degrees and hook 20 in extended position 23. FIG. 15M shows a right sagittal perspective view of complete head portion with suture needle 18 in first bite position rotated 465 degrees and hook 20 in extended position 23. FIG. 15N shows a posterior perspective view of complete head portion with suture needle 18 in first bite position rotated 465 degrees and hook 20 in extended position 23. FIG. 15O shows an anterior perspective view of complete head portion with suture needle 18 in first bite position rotated 465 degrees and hook 20 in extended position 23. FIG. 15P shows a inferior perspective view of complete head portion with suture needle 18 in first bite position rotated 465 degrees, hook (not shown) in extended position (not shown), and holding arm 36 in home position. FIG. 15Q shows a inferior perspective view of complete head portion with suture needle 18 in first bite position rotated 465 degrees, hook 20 in extended position 23, and holding arm (not shown) in home position. FIG. 15R shows a right sagittal-anterior-inferior perspective view with focus on major components of head portion; the suture needle 18 is in first bite position with hook 20 extended. FIG. 15S shows a right sagittal-anterior-inferior perspective view with focus on major components of head portion with edge separator 50 removed to provide complete view of extended hook 20. FIG. 15T shows a right sagittal-anterior-inferior perspective view with expanded focus on major components of head portion to include holding arm rotating shaft wheel 38; the suture needle 18 is rotated back 30 degrees, and hook 20 is in locked position to catch loop.

FIGS. 16A, 16B refer to a preferred embodiment of the complete suturing module assembly 60 encased within a general housing 12. FIG. 16A is a right sagittal-anterior-superior perspective view of complete suture machine with general housing 12. FIG. 16B is a right sagittal-anterior-inferior perspective view of complete suture machine with general housing 12. The general housing is removably, attachably mounted to a handle (not shown), which contains the automated gear devices. The complete handle 62 and suturing module assembly 60 are displayed in FIG. 17. In a preferred embodiment, the handle 62 is resterilizable separately from the suture module assembly 60. The suture module assembly is preferably disposable.

A difference between the embodiments of FIGS. 13-16 and FIGS. 1-5 is the mechanical actuating means for moving the stitch of the previous loop away from the hook 20. FIGS. 1-5 use a catcher comprising a push and a catch arm, which move independently but function cooperatively, whereas FIGS. 13-16 use a holding arm, which is a single L-shaped element controlled by the rotation of a rotary shaft and rotary shaft wheel. More specifically, the holding arm comprises a shaft and head. The head holds the loop of the previous stitch against the hook shank so the hook can move through the loop. After the hook has moved through the loop of the previous stitch to grab the loop of the current stitch, the holding arm head moves away from the hook shank toward the hook point at least the length of the hook gape; this movement pushes the loop of the previous stitch away from the hook so the hook can retract to above the holding arm head without grabbing the loop of the previous stitch. Following hook retraction, the holding arm head releases the loop of the previous stitch and returns to its home position by completing a circular path through the hook path, where the head pulls the loop of the current stitch to the home position next to the hook shank.

FIG. 17A refers to a complete handle 62 and suturing module assembly 60. FIG. 17B displays an open assembly with interior handle components connected to suturing module assembly components, such as the holding arm rotary shaft 37, suture needle 18, tensioner 45, edge separator 50, the holding arm 36, holding arm wheel 38, holding arm spindle 35, suture needle 18, suture needle shaft 17, compound needle 30, hook 20, and hook spring 19.

An alternative embodiment incorporates a suture thread supply connected to a tensioner 45 that extends through the housing to be externally manipulated and is displayed in FIGS. 18A-18D. FIG. 18A shows a right sagittal perspective view of the suturing module assembly 60 including the tensioner 45. FIG. 18B shows a left sagittal perspective view of the suturing module assembly 60 including the tensioner 45. FIG. 18C shows a right sagittal-anterior perspective view of the suturing module assembly 60 including the tensioner 45. FIG. 19 shows the tensioner 45. The tensioner comprises a bolt 46 and spring 47, that compress the suture bobbin 48 when tightened. The tensioner may be manipulated external to the general housing; by turning the tensioner to increase the drag, stitches that compress the tissue edges more tightly are created.

FIG. 20 illustrates a compound needle, generally described as 30, including a hook and a closing element or tongue. FIG. 20A displays the compound needle components: hook 20; tongue 70; spring seat 71; and spring 19. FIG. 20B displays all the components in the compound needle closed position; the tongue is extended to close hook access. FIG. 20C is a detailed view of the closed compound needle. FIG. 20D displays all the components in the compound needle open position; the tongue is retracted to open hook access. FIG. 20E is a detailed view of the open compound needle.

Note that these diagrams are all indicated as being oriented to the wound without angle. It could be vertical for skin. If muscles or other organs, it may be 45 degree angle. The footer may also be angled to facilitate suturing. For example, FIG. 21A displays a suturing module assembly 60 with the edge separator and a 90 degree footing. FIG. 21B displays the same suturing module assembly 60 with the edge separator removed and a 45 degree angled footing, which allows the suture needle to stitch at an angle for potentially more optimal internal suturing. In the skin, you take bites parallel to skin. For muscles, fascia or internal organs it may be preferable to angle the entire the machine, or change the angle of the base of the machine body in a way to serve the function of suturing the target tissue. As will be appreciated there are a variety of different suture materials may be used; these may range from 10/0 smallest to #2. Refer to the tables 1 and 2 for suture material and for suture needles used commercially. Regarding preferred size of suture needle, it depends on tissue type. Regarding size of the device, overall width is preferably less than one inch, which is about the size of a basic suture width. Commercial device would be preferably about ½ inch. Note that the most important dimension relating to the present invention is the diameter of the helico-spiral suture needle spiral.

In other embodiments of the machines of the present invention, the machines are preloaded with a suture thread that is knotted at its first end so that at the first stitch, the knot catches inside the tissue to be stitched. Overall dimensions of the machine for automated suturing, particularly for disposable machines intended for single use application provide for a machine height less than about one inch. A quick connect is preferred to attach the machine housing and functional components to a handle and motor shaft. Advantageously, the methods of the present invention provide for better cooptation of the wound; and this reduces the chance of infection. If used for hollow organs, intestines, it will minimize leakage. Also note that it facilitates surgical suturing and minimizes the time of suturing. Speed is very important. The methods of the present invention are at least about twice as fast as manual suturing methods.

In other embodiments of the present invention, preferably a guard is provided to maintain the tissue to be sutured in a substantially edge-abutting position equal on both sides of the suture needle and hook region of the machine; also preferably a separator at the front of the stitching area is provided, such as by way of example and not limitation, a separator comprising a vertical plunger device or mechanism.

Certain modifications and improvements will occur to those skilled in the art upon a reading of the foregoing description. The above-mentioned and following examples are provided to serve the purpose of clarifying the aspects of the invention and it will be apparent to one skilled in the art that they do not serve to limit the scope of the invention. Other example applications include devices and methods to close skin, muscles, fascia, and hollow organs like intestines, bladder, etc. The device can be modified with an extended shaft such that it can be used through a laparoscope in laparoscopic and robotic surgery. Note also that the machine may be programmed by microprocessor, program, controlled by circuit board, timing controls and set of gears and micro servos to coordinate all the motions to be fully automated and programmable.

Also, a footing mechanism with roller can be added to the base of the device where it comes in contact with the sutured tissue so as to advance the machine in synchronized motion with the helico-spiral suture needle. The roller mechanism can advance the device in relation to the sutured tissue at predetermined speed.

The base (footing) of the body of the machine (device) can be modified to allow the device to perform subcuticular skin suturing (inserting the suture beneath the outer layer of the skin, parallel to the skin surface). This is a standard surgical technique that is done, prior to this art, manually by the surgeon to achieve cosmetic healing with minimal scarring. It is a tedious process and time consuming. This invention makes this process speedy and consistently accurate.

To achieve the above-mentioned objectives, the footing (not shown) of the device that comes in contact with the skin surface is offset. Thus, the skin surfaces of the cut are offset, FIG. 4; with one side 52 higher than the other, lower side 53. Distance 55 in FIG. 4 represents this offset, which is equal to pitch of the helico-spiral suture needle, that is, the distance 51 (the distance between the coils of the helico-spiral suture needle).

As a result of the offsetting of the foot of the device, the skin surface is also offset with equal distance as the device-footing offset. In an example embodiment, this distance is about 2 mm, which is the average thickness of the outer layer of the skin below which it is desirable to insert the subcuticular skin sutures to achieve cosmetic result with minimal scarring. When the helico-spiral suture needle starts its turn stitch cycle, it first enters the subcutis on the edge of a first side 52 (FIG. 4) on the side of the wound that is higher, sideways tangential (parallel) with the skin surface and preferably perpendicular to the wound edge. In cases where the edge is not planar, the surgeon can make the appropriate entry such that the stitch will bring the tissue edges in proper apposition. The suture needle continues its rotation beyond the 180 degrees, going lower while rotating until it exits the first side 52 and enters the skin edge on the lower side 53 of the wound FIG. 5.

The suture needle completes a 360 degree rotation, exiting the left edge of the wound about 1 mm below the depth of the entry point, and continues turning about 45 degrees to allow the hook 20 FIG. 5 to pick the suture loop up. The helico-spiral suture needle then reverses direction 405 degrees backwards to return to its home base in the device housing, thus completing one stitch cycle. Thus, the helico-spiral suture needle rotates at least about one and one-eighth turns. The whole device advances forward to start another stitch cycle, the skin edges that have been sutured come together in apposition with edge to edge adaptation and surface to surface configuration that provides for cosmetically acceptable scarring as healing can occur without skin edges overlapping and the cutis is not disturbed by sutures. Thus device thus makes subsurface appositional sutures.

To further clarify the orientation of the device in relation to the wound, we consider the front of the wound, that area of the skin that has not been sutured yet in front of the advancing device and the back of the wound is that area of the skin that has been sutured.

The footing of the device is flat (on the same plane) on both sides behind the area where the slanted surface ends and meets the flat surface 54 FIG. 5. Thus the skin surface that has already been sutured and underneath this back part of the device housing, is on the same plane without any offsetting, hence without skin edge overlap.

Another advantage of the subcuticular suturing technique is that the suture material is hidden underneath the skin, thus leaving no skin marks, compared to the standard skin stapling technique or other methods of suturing whereas the suture material is exposed outside the skin. The subcuticular suture material that is proposed to be used by the device is absorbable by the body in few weeks (see Ethicon suture table 1) thus there is no need to remove the suture later on. An example of such suture material is the mono-filament suture called Monocryl 5/0 (Ethicon trademark).

Also, keeping the suture material underneath the skin does minimize the chances of wound infection and it also eliminates the pain associated with removing the suture 7-10 days later on (such is the case when using the standard method of skin suturing). The patient also feels much less pain associated with subcuticular suturing compared with the standard exposed sutures.

Note that the present invention provides for continuous suturing; however, the device does not move at constant speed when in use; so then preferred methods of the present invention provide for a visual indication showing when to move the device, and/or in automated versions for a machine, the machine is preferably programmed to move only when the suture needle is out of the tissue.

By way of example and not limitation, it is considered within the scope of the present invention that the machines, methods, and needles may be adapted for stitching non-biologic material, or for non-medical purposes, such as stitching leather, artificial leather, etc. Thus, the device of the present invention can use different types of suturing materials to meet different needs. Also, possible use of the device in different industries, such as by way of example and not limitation, veterinary medicine, textiles, automotive, industrial, and other markets. All modifications and improvements have been deleted herein for the sake of conciseness and readability but are properly within the scope of the present invention.

What is claimed is:
1. A module comprising:
a needle with a needle shaft; a supply of thread; a thread guide; a hook with a hook shank, a holding arm mechanism with a holding arm shaft; and a housing;

the needle rotationally movable between a first position and a second position and configured to introduce the thread into a first edge of a tissue at a first point and a second edge of the tissue at a second point;

the thread guide operable to supply the thread to the needle;

the hook operable for hooking and lifting the thread in coordination with the needle; and the holding arm mechanism operable for pushing and catching the thread in automatic coordination with the hook; the needle, the hook, and the holding arm mechanism held in position by the housing; and the housing operable to attach to a power supply that provides power to the module;

thereby providing a module for automatically creating a stitch.

2. The module of claim 1, wherein the housing includes a footer angled between about 0 degrees and about 90 degrees to the rotational axis of the needle.

3. The module of claim 1, further including a footing mechanism with a roller operable to advance the module in synchronized motion with the needle.

4. The module of claim 1, wherein the housing includes a footer and the needle is helical with a pitch and the footer is offset anteriorly to match the pitch.

5. The module of claim 1, wherein the needle is spiral, circular, helical, or helical-spiral.

6. The module of claim 1, wherein the hook is a compound needle comprising the hook with a spring seat, a tongue with a spring seat, and a spring; and wherein the tongue is operable to reversibly lock the thread in the hook.

7. The module of claim 1, wherein the needle is hollow or solid.

8. The module of claim 1, wherein the needle is operable to rotate between about 360 degrees and about 405 degrees.

9. The module of claim 1, further including a guard configured to hold a tissue to be sutured in a substantially edge-abutting position equal on both sides of the needle and hook region of the module.

10. The module of claim 1, further including a visual indication showing when to move the module.

11. The module of claim 1, further including an extended needle shank, extended holding arm shaft and extended hook shaft such that the module can be used through a laparoscope in laparoscopic and robotic surgery.

12. The module of claim 1, further including an edge separator configured to separate the edges of a tissue.

13. The module of claim 12, wherein the edge separator comprises a vertical plunger mechanism.

14. The module of claim 1, further including a tensioner.

15. The module of claim 14, wherein the supply of thread is on a bobbin, and the tensioner includes a bolt and a spring adjustable to increase drag on the bobbin.

16. A module comprising:

a needle; a supply of thread; a thread guide; a hook, a holding arm mechanism; and a housing;

the needle movable between a first position and a second position and operable for introducing the thread into a first edge at a first point and a second edge at a second point;

the thread guide operable to supply the thread to the needle;

the hook operable for hooking and lifting the thread in coordination with the needle; and the holding arm mechanism operable for pushing and catching the thread in coordination with the hook;

the needle, the hook, and the holding arm mechanism held in position by the housing; and the housing operable to attach to a power source that provides power to the module.

17. The module of claim 16, further comprising a compound needle including a hook and a tongue, wherein the needle, the compound needle and the holding arm configured in the module housing to create a series of subsurface stitches.

18. The module of claim 16, wherein the needle shape is helical, circular, helico-spiral or spiral.

19. A module comprising:

a needle, a compound needle including a hook and a tongue, a holding arm, a material threaded in the needle, and a housing;

the needle, the compound needle, and the holding arm held in position by the housing;

the needle, the compound needle, and the holding arm configured in the housing to create a series of continuous subsurface stitches;

the module removably connected to a power source.

20. The module of claim 19, wherein the needle is rotationally movable between a first position and a second position and configured to introduce the material into a first edge of a tissue at a first point and a second edge of the tissue at a second point.

* * * * *